United States Patent
Kimes et al.

(10) Patent No.: US 11,369,644 B2
(45) Date of Patent: Jun. 28, 2022

(54) MICROBIAL CONSORTIA

(71) Applicants: Siolta Therapeutics, Inc., San Carlos, CA (US); The Regents of the University of California, Oakland, CA (US)

(72) Inventors: Nikole Kimes, San Francisco, CA (US); Ricardo Valladares, Brookhaven, GA (US); Benjamin Fiebiger, San Francisco, CA (US); Susan V. Lynch, Piedmont, CA (US)

(73) Assignees: SIOLTA THERAPEUTICS, INC., San Francisco, CA (US); THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 17/067,354

(22) Filed: Oct. 9, 2020

(65) Prior Publication Data

US 2021/0077541 A1    Mar. 18, 2021

Related U.S. Application Data

(63) Continuation of application No. PCT/US2019/026674, filed on Apr. 9, 2019.

(60) Provisional application No. 62/655,562, filed on Apr. 10, 2018.

(51) Int. Cl.
*A61K 35/74* (2015.01)
*A61P 29/00* (2006.01)
*A61K 9/00* (2006.01)

(52) U.S. Cl.
CPC .............. *A61K 35/74* (2013.01); *A61P 29/00* (2018.01); *A61K 9/0053* (2013.01)

(58) Field of Classification Search
None
See application file for complete search history.

(56) References Cited

U.S. PATENT DOCUMENTS

| | | | |
|---|---|---|---|
| 7,488,804 B2 | 2/2009 | Saxon et al. |
| 9,011,834 B1 | 4/2015 | McKenzie et al. |
| 9,028,841 B2 | 5/2015 | Henn et al. |
| 9,173,910 B2 | 11/2015 | Kaplan et al. |
| 9,415,079 B2 | 8/2016 | Honda et al. |
| 9,421,230 B2 | 8/2016 | Honda et al. |
| 9,433,652 B2 | 9/2016 | Honda et al. |
| 9,439,953 B2 | 9/2016 | De Simone |
| 9,486,487 B2 | 11/2016 | Cutcliffe et al. |
| 9,603,876 B2 | 3/2017 | Blaser et al. |
| 9,642,882 B2 | 5/2017 | Honda et al. |
| 9,662,381 B2 | 5/2017 | Honda et al. |
| 9,801,933 B2 | 10/2017 | Honda et al. |
| 9,808,519 B2 | 11/2017 | Honda et al. |
| 9,827,276 B2 | 11/2017 | Honda et al. |
| 9,833,483 B2 | 12/2017 | Honda et al. |
| 10,058,576 B2 | 8/2018 | Bushman et al. |
| 10,092,603 B2 | 10/2018 | Honda et al. |
| 10,149,867 B2 | 12/2018 | Kaplan et al. |
| 10,149,870 B2 | 12/2018 | Kaplan et al. |
| 10,322,150 B2 | 6/2019 | Honda et al. |
| 10,328,108 B2 | 6/2019 | Honda et al. |
| 10,537,597 B2 | 1/2020 | O'Mahony et al. |
| 10,555,978 B2 | 2/2020 | Honda et al. |
| 10,668,116 B2 | 6/2020 | Cutcliffe et al. |
| 10,668,118 B2 | 6/2020 | Lynch et al. |
| 10,675,312 B2 | 6/2020 | Cutcliffe et al. |
| 10,842,830 B2 | 11/2020 | Cutcliffe et al. |
| 10,842,831 B2 | 11/2020 | Cutcliffe et al. |
| 11,033,588 B2 | 6/2021 | Lynch et al. |
| 2003/0161826 A1 | 8/2003 | Arnason et al. |
| 2004/0133356 A1 | 7/2004 | Jardetzky et al. |
| 2008/0166331 A1 | 7/2008 | Su et al. |
| 2008/0193373 A1 | 8/2008 | Stritzker et al. |
| 2010/0172874 A1 | 7/2010 | Turnbaugh et al. |
| 2010/0196340 A1 | 8/2010 | Graf et al. |
| 2011/0189220 A1 | 8/2011 | Yang et al. |
| 2012/0027736 A1 | 2/2012 | Morita et al. |
| 2012/0219551 A1 | 8/2012 | Johnson et al. |
| 2014/0147425 A1 | 5/2014 | Henn et al. |
| 2014/0363397 A1 | 12/2014 | Allen-Vercoe et al. |
| 2015/0004161 A1 | 1/2015 | Zhu |
| 2015/0095241 A1 | 4/2015 | Edwards |
| 2015/0110834 A1 | 4/2015 | Underhill et al. |
| 2015/0218258 A1 | 8/2015 | Francis et al. |

(Continued)

FOREIGN PATENT DOCUMENTS

| CA | 2938790 A1 | 8/2015 |
| CN | 102132788 B | 11/2012 |

(Continued)

OTHER PUBLICATIONS

Khan et al (PLOS One 9(5):e96097, pp. 1-7, 2014).*
Co-pending U.S. Application No. 202117475228, inventors Kimes; Nikole et al., filed on Sep. 14, 2021.
Aichbhaumik, N. et al. (Nov. 2008, e-published Aug. 11, 2008). "Prenatal exposure to household pets influences fetal immunoglobulin E production," Clin Exp Allergy 38(11):1787-1794.
Arrieta, et al. A humanized microbiota mousemodel of ovalbumin-induced lung inflammation. Gut Microbes. 2016;7(4):342-352. doi:10.1080/19490976.2016.1182293.
Arrieta, et al. Early infancy microbial and metabolic alterations affect risk of childhood asthma. Sci Transl Med. 2015;7(307):307ra152-307ra152. doi:10.1126/scitranslmed.aab2271.

(Continued)

*Primary Examiner* — Brian Gangle
(74) *Attorney, Agent, or Firm* — Wilson Sonsini Goodrich & Rosati

(57) ABSTRACT

Provided herein are microbial strains isolated de novo. In some instances, the bacterial strains include genera, species, and/or strains of *Lactobacillus johnsonii, Lactobacillus crispatus, Faecalibacterium prausnitzii, Akkermansia muciniphila, Bifidobacterium longum*, and/or *Bifidobacterium longum infantis* strains. These bacterial strains can be used in the treatment of dysbiosis, inflammation, and other disorders.

26 Claims, 22 Drawing Sheets

(56) References Cited

U.S. PATENT DOCUMENTS

| | | |
|---|---|---|
| 2015/0246081 A1 | 9/2015 | Morris |
| 2015/0306152 A1 | 10/2015 | Cani et al. |
| 2016/0022592 A1 | 1/2016 | Kabadi et al. |
| 2016/0030494 A1 | 2/2016 | Henn et al. |
| 2016/0068890 A1 | 3/2016 | Pichaud et al. |
| 2016/0108105 A1 | 4/2016 | Yang et al. |
| 2016/0113971 A1 | 4/2016 | Kaplan et al. |
| 2016/0143961 A1 | 5/2016 | Berry et al. |
| 2016/0143962 A1 | 5/2016 | Berry et al. |
| 2016/0199424 A1 | 7/2016 | Berry et al. |
| 2016/0228476 A1 | 8/2016 | Cutcliffe et al. |
| 2016/0235792 A1 | 8/2016 | Berry et al. |
| 2016/0243172 A1 | 8/2016 | Cook et al. |
| 2016/0256383 A1 | 9/2016 | Allio et al. |
| 2016/0271188 A1 | 9/2016 | Berry et al. |
| 2016/0271189 A1 | 9/2016 | Cutcliffe et al. |
| 2016/0317653 A1 | 11/2016 | Cook et al. |
| 2017/0020932 A1 | 1/2017 | Cutcliffe et al. |
| 2017/0027996 A1 | 2/2017 | Cutcliffe et al. |
| 2017/0151291 A1 | 6/2017 | Henn et al. |
| 2017/0173086 A1 | 6/2017 | Boyle et al. |
| 2017/0224745 A1 | 8/2017 | Dart |
| 2017/0235902 A1 | 8/2017 | Almonacid et al. |
| 2017/0296596 A1 | 10/2017 | Allen-Vercoe et al. |
| 2017/0368108 A1 | 12/2017 | Kaplan et al. |
| 2018/0028576 A1 | 2/2018 | Blaser et al. |
| 2018/0250347 A1 | 9/2018 | Cani et al. |
| 2018/0353554 A1 | 12/2018 | Henn et al. |
| 2019/0030095 A1 | 1/2019 | Cutcliffe et al. |
| 2019/0030096 A1 | 1/2019 | Cutcliffe et al. |
| 2019/0046590 A1 | 2/2019 | Kaplan et al. |
| 2019/0070225 A1 | 3/2019 | Strandwitz et al. |
| 2019/0070227 A1 | 3/2019 | Cutcliffe et al. |
| 2019/0070228 A1 | 3/2019 | Cutcliffe et al. |
| 2019/0105359 A1 | 4/2019 | Bushman et al. |
| 2019/0160118 A1 | 5/2019 | Scheiman et al. |
| 2019/0183941 A1 | 6/2019 | De Vos et al. |
| 2019/0216861 A1 | 7/2019 | Kashyap et al. |
| 2019/0262407 A1 | 8/2019 | Dutta |
| 2019/0282630 A1 | 9/2019 | Cani et al. |
| 2019/0282634 A1 | 9/2019 | Honda et al. |
| 2019/0282638 A1 | 9/2019 | Sokol et al. |
| 2020/0054697 A1 | 2/2020 | De Paiva et al. |
| 2020/0121738 A1 | 4/2020 | Cutcliffe et al. |
| 2020/0121742 A1 | 4/2020 | Lynch et al. |
| 2020/0197451 A1 | 6/2020 | Kuspa et al. |

FOREIGN PATENT DOCUMENTS

| | | |
|---|---|---|
| CN | 104726596 A | 6/2015 |
| CN | 104955466 A | 9/2015 |
| EP | 0322834 B1 | 10/1993 |
| EP | 1177794 A2 | 2/2002 |
| EP | 2369016 A1 | 9/2011 |
| EP | 2836224 A2 | 2/2015 |
| EP | 3539548 A1 | 9/2019 |
| JP | 2008169198 A | 7/2008 |
| JP | 2017137332 A | 8/2017 |
| JP | 6551944 B2 | 7/2019 |
| WO | WO-2007138011 A1 | 12/2007 |
| WO | WO-2011094579 A2 | 8/2011 |
| WO | WO-2012039615 A2 | 3/2012 |
| WO | WO-2013107913 A1 | 7/2013 |
| WO | WO-2013130773 A2 | 9/2013 |
| WO | WO-2014075745 A1 | 5/2014 |
| WO | WO-2014076246 A1 | 5/2014 |
| WO | WO-2014082050 A1 | 5/2014 |
| WO | WO-2014121302 A2 | 8/2014 |
| WO | WO-2015095241 A2 | 6/2015 |
| WO | WO-2017053544 A1 | 3/2017 |
| WO | WO-2017060698 A1 | 4/2017 |
| WO | WO-2017079450 A1 | 5/2017 |
| WO | WO-2017134240 A1 | 8/2017 |
| WO | WO-2017152137 A2 | 9/2017 |
| WO | WO-2017180987 A1 | 10/2017 |
| WO | WO-2017184601 A1 | 10/2017 |
| WO | WO-2018187272 A1 | 10/2018 |
| WO | WO-2018194889 A1 | 10/2018 |
| WO | WO-2019032572 A1 | 2/2019 |
| WO | WO-2019032573 A1 | 2/2019 |
| WO | WO-2019032575 A1 | 2/2019 |
| WO | WO-2019035089 A2 | 2/2019 |
| WO | WO-2019043051 A1 | 3/2019 |
| WO | WO-2019046646 A1 | 3/2019 |
| WO | WO-2019118515 A2 | 6/2019 |
| WO | WO-2019136269 A1 | 7/2019 |
| WO | WO-2019166533 A1 | 9/2019 |
| WO | WO-2019168990 A1 | 9/2019 |
| WO | WO-2019199895 | 10/2019 |
| WO | WO-2020172473 A1 | 8/2020 |
| WO | WO-2021071864 A1 | 4/2021 |

OTHER PUBLICATIONS

Asher et al. Worldwide time trends in the prevalence of symptoms of asthma, allergic rhinoconjunctivitis, and eczema in childhood: ISAAC Phases One and Three repeat multicountry cross-sectional surveys. Lancet 368:733-743 (2006).

Atarashi et al. Induction of colonic regulatory T cells by indigenous Clostridium species. Science 331(6015):337-341 (2011).EpubDec. 23, 2010.

Backhed, et al. Dynamics and Stabilization of the Human Gut Microbiome during the First Year of Life. Cell Host & Microbe. 2015;17(5):690-703. doi:10.1016/j.chom.2015.04.004.

Bamias G. et al. (May 2011). "Cytokines in the pathogenesis of ulcerative colitis," Discov Med 11(60):459-467.

Brown, B. Akkermansia: new discoveries from the microbiome. Functional Medicine—Masterclass, Sep. 30, 2014. Retrieved from the Internet: URL:http://www.timeforwellness.org/files/akkermansia.pdf [retrieved on Dec. 7, 2016].

Chehoud C. et al. (Aug. 2015). "A Fungal Signature in the Gut Microbiota of Pediatric Patients With Inflammatory Bowel Disease," Inflamm Bowel Dis 21(8):1948-1956.

Chelakkot, et al. Akkermansia muciniphila-derived extracellular vesicles influence gut permeability through the regulation of tight junctions. Exp Mol Med. Feb. 23, 2018;50(2):e450. doi: 10.1038/emm.2017.282.

Couturier-Maillard, et al. NOD2-mediated dysbiosis predisposes mice to transmissible colitis and colorectal cancer. J Clin Invest. Feb. 1, 2013; 123(2): 700-711.

Dello S.A. et al. (2013). "Systematic review of ophthalmate as a novel bio-marker of hepatic glutathione depletion," Clin Nutr 32(3):325-330.

Depommier, et al. Supplementation with Akkermansia muciniphila in overweight and obese human volunteers: a proof-of-concept exploratory study. Nat Med. Jul. 2019;25(7):1096-1103. doi: 10.1038/s41591-019-0495-2. Epub Jul. 1, 2019.

Devereux, G. The increase in the prevalence of asthma and allergy: food for thought. Nat Rev Immunol. 2006;6(11):869-874. doi:10.1038/nri1958.

Durack, et al. Delayed gut microbiota development in high-risk for asthma infants is temporarily modifiable by Lactobacillus supplementation. Nat Commun. 2018;9(1):733. doi:10.1038/s41467-018-03157-4.

EP17760954.2 The Extended European Search Report dated Oct. 14, 2019.

Everard, et al. (2013). Cross-talk between Akkermansia muciniphila and intestinal epithelium controls diet-induced obesity. Proc. Natl. Acad. Sci. U.S.A. 110, 9066-9071. doi: 10.1073/pnas.1219451110.

Frank, D.N. et al. (Jan. 2011, e-published Sep. 13, 2010). "Disease phenotype and genotype are associated with shifts in intestinal-associated microbiota in inflammatory bowel diseases," Inflamm Bowel Dis 17(1):179-184.

Fujimura, et al. House dust exposure mediates gut microbiome Lactobacillus enrichment and airway immune defense against allergens and virus infection. Proc Natl Acad Sci USA. 2014;111(2):805-810. doi:10.1073/pnas.1310750111.

(56) References Cited

OTHER PUBLICATIONS

Fujimura, et al. Neonatal gut microbiota associates with childhood multisensitized atopy and T cell differentiation. Nat Med. 2016;22(10):1187-1191. doi:10.1038/nm.4176.
Furuta, et al. The National Biome Initiative: An allergy perspective. J Allergy Clin Immunol. Apr. 2017;139(4):1131-1134. doi: 10.1016/j.jaci.2017.02.008. Epub Feb. 28, 2017.
Garber, K. Drugging the gut microbiome. Nat Biotechnol. Mar. 2015;33(3):228-31.
Gevers D, Kugathasan S, Denson LA et al. The treatment-naive microbiome in new-onset crohn's disease. Cell Host Microbe 2014;15:382-92. doi:10.1016/j.chom.2014.02.005.
Gibson, et al. Inulin and oligofructose: New scientific developments. Nutrition Today 43.2 (2008): 54-59.
Graham-Rowe D. Lifestyle: When allergies go west. Nature. 2011;479:S2-S4.
Hansen, et al., Early life treatment with vancomycin propagates Akkermansia muciniphila and reduces diabetes incidence in the NOD mouse, Diabetologia (2012), 55:2285-2294.
Henricks, P.A et al. (Jan. 1991). "9- and 13-hydroxy-linoleic acid possess chemotactic activity for bovine and human polymorphonuclear leukocytes," Prostaglandins 41(1):21-27.
Herbst et al. Dysregulation of Allergic Airway Inflammation in the Absence of Microbial Colonization. Am J Respir Crit Care Med. 184(2):198-205 (2011).
Hijazi, et al. Intestinal permeability is increased in bronchial asthma. Archives of disease in childhood 89.3 (2004): 227-229.
Hilty, et al. Disordered Microbial Communities in Asthmatic Airways. PLoS One. 2010; 5(1): e8578.
Hoffmann, C. et al. (2013). "Archaea and fungi of the human gut microbiome: correlations with diet and bacterial residents," PLoS One 8(6):e66019.
Hogan, D.A. et al. (Dec. 2004). "A Pseudomonas aeruginosa quorum-sensing molecule influences Candida albicans morphology," Mol Microbiol 54(5):1212-1223.
Hou, Y.C. et al. (Apr. 2013, e-published Jul. 31, 2012). Effects of alanyl-glutamine dipeptide on the expression of colon-inflammatory mediators during the recovery phase of colitis induced by dextran sulfate sodium, Eur J Nutr 52(3):1089-1098.
International Search Report dated Jun. 9, 2017, for PCT Application No. PCT/US2017/020809, filed Mar. 3, 2017, 5 pages.
Jeffery, et al. Allergic rhinitis and asthma: inflammation in a oneairway condition. BMC Pulm Med. 2006;6 Suppl 1(Suppl 1):S5. doi:10.1186/1471-2466-6-S1-S5.
Jensen, S.S. et al. (Jul. 27, 2010). "Differential induction of inflammatory cytokines by dendritic cells treated with novel TLR-agonist and cytokine based cocktails: targeting dendritic cells in autoimmunity," J Inflamm 7:37.
Juyal G. et al. (Jan. 31, 2011). "An investigation of genome-wide studies reported susceptibility loci for ulcerative colitis shows limited replication in north Indians," PLoS One 6:e16565.
Kumar, et al. Pharmaceutical suspensions: patient compliance oral dosage forms.World Journal of Pharmacy and Pharmaceutical Sciences 7.12 (2016): 1471-1537.
Levy, M. et al. (Dec. 3, 2015). "Microbiota-Modulated Metabolites Shape the Intestinal Microenvironment by Regulating NLRP6 Inflammasome Signaling," Cell 163(6):1428-1443.
Lewis J.D. et al. (Oct. 14, 2015). "Inflammation, Antibiotics, and Diet as Environmental Stressors of the Gut Microbiome in Pediatric Crohn's Disease," Cell Host Microbe 18(4):489-500.
Li Q. et al. (Jul. 2014). "Dysbiosis of gut fungal microbiota is associated with mucosal inflammation in Crohn's disease," J Clin Gastroenterol 48(6):513-523.
Liao, J. et al. (Feb. 2007, e-published Sep. 14, 2006). "Inhibition of chronic ulcerative colitis associated adenocarcinoma development in mice by inositol compounds," Carcinogenesis 28(2):446-454.
Mar, J.S. et al. (Aug. 16, 2016). "Disease Severity and Immune Activity Relate to Distinct Interkingdom Gut Microbiome States in Ethnically Distinct Ulcerative Colitis Patients," mBio 7(4):e01072-16, pp. 1-11.

Mistry, D. et al. (Aug. 2010). "Gamma-glutamyl transferase: the silent partner?" COPD 7(4):285-290.
Morgan, X.C. et al. (Apr. 16, 2012). "Dysfunction of the intestinal microbiome in inflammatory bowel disease and treatment," Genome Biol 13(9):R79.
Munoz, et al. Interleukin (IL)-23 mediates Toxoplasma gondii-induced immunopathology in the gut via matrixmetalloproteinase-2 and IL-22 but independent of IL-17. J Exp Med. Dec. 21, 2009; 206(13): 3047-3059.
Nagalingam, N.A. et al. (May 2012, e-published Sep. 20, 2011). "Role of the microbiota in inflammatory bowel diseases," Inflamm Bowel Dis 18(5):968-984.
Nascimento N.R. et al (Jan. 3, 2006, Dec. 22, 2005). "Inositols prevent and reverse endothelial dysfunction in diabetic rat and rabbit vasculature metabolically and by scavenging superoxide," PNAS USA 103(1):218-223.
Neuman M.G. et al. (Jul. 2012, e-published Sep. 24, 2011). "Inflammatory bowel disease: role of diet, microbiota, life style," Transl Res 160(1):29-44.
Noverr. M.C. et al. (Sep. 2004). "Role of antibiotics and fungal microbiota in driving pulmonary allergic responses," Infect Immun 72(9):4996-5003.
Ohkusa, T. et al. (May 2009). "Commensal bacteria can enter colonic epithelial cells and induce proinflammatory cytokine secretion: a possible pathogenic mechanism of ulcerative colitis," J Med Microbiol 58(Pt 5):535-545.
Pamer, E. G. "Fecal microbiota transplantation: effectiveness, complexities, and lingering concerns." Mucosal immunology 7.2 (2014): 210-214.
Park, J. et al. (Jan. 2015, e-published Jun. 11, 2014). "Short-chain fatty acids induce both effector and regulatory T cells by suppression of histone deacetylases and regulation of the mTOR-S6K pathway," Mucosal Immunol 8(1):80-93.
Park, S.K. et al. (Apr. 2012, e-published May 13, 2011). "*Blautia stercoris* sp. nov., isolated from human faeces," Int J Syst Evol Microbiol 62(Pt 4):776-779.
Pascal, et al. Microbiome and allergic diseases.Frontiers in immunology 9 (2018): 1584.
Patel, K.P. et al. (Jun. 2012, e-published Apr. 5, 2012). "The production of p-cresol sulfate and indoxyl sulfate in vegetarians versus omnivores," Clin J Am Soc Nephrol 7(6):982-928.
PCT/US2019/26674 International Search Report dated Aug. 27, 2019.
Plovier, et al. A purified membrane protein from Akkermansia muciniphila or the pasteurized bacterium improves metabolism in obese and diabetic mice. Nature Medicine, Jan. 2017, 23(1):107-16.
Prindiville, T.P. et al. (Mar.-Apr. 2000). "Bacteroides fragilis enterotoxin gene sequences in patients with inflammatory bowel disease," Emerg Infect Dis 6(2):171-174.
Punchard, et al. The Journal of Inflammation. Journal of Inflammation. 1(1): 1-4 (2004).
Qin, X. et al. (May-Jun. 2014, e-published May 2, 2014). "Lysophosphatidylcholine perpetuates macrophage polarization toward classically activated phenotype in inflammation," Cell Immunol 289(1-2):185-190.
Rath, H.C. et al. (Jun. 1999). "Differential induction of colitis and gastritis in HLA-B27 transgenic rats selectively colonized with Bacteroides vulgatus or *Escherichia coli*," Infect Immun 67(6):2969-2974.
Remely, et al. Increased gut microbiota diversity and abundance of Faecalibacterium prausnitzii and Akkermansia after fasting: a pilot study.Wiener klinische Wochenschrift 127.9-10 (2015): 394-398.
Riedel, C.U. et al. (Jun. 21, 2006). "Anti-inflammatory effects of bifidobacteria by inhibition of LPS-induced NF-kappaB activation," World J Gastroenterol 12(23):3729-3735.
Rolin, J. et al. (Jun. 2013, e-published Oct. 26, 2012). "Oxidized lipids and lysophosphatidylcholine induce the chemotaxis and intracellular calcium influx in natural killer cells," Immunobiology218(6):875-883.
Rowe, et al (Eds). Handbook of Pharmaceutical Excipients. Pharmaceutical Press. 2009. Sixth Edition; p. 283-286.
Sakanaka, A. et al. (Aug. 28, 2015, e-published Jun. 17, 2015). "Arginine-Ornithine Antiporter ArcD Controls Arginine Metabo-

(56) References Cited

OTHER PUBLICATIONS lism and Interspecies Biofilm Development of *Streptococcus gordonii*," J Biol Chem 290(35):21185-21198.

Santee, et al. Nasopharyngeal microbiota composition of children is related to the frequency of upper respiratory infection and acute sinusitis. Microbiome. 2016; 4: 34. Published online Jul. 1, 2016. doi: 10.1186/s40168-016-0179-9.

Schepers, E. et al. (Feb. 2007, e-published Oct. 13, 2006). "P-cresylsulphate, the main in vivo metabolite of p-cresol, activates leucocyte free radical production," Nephrol Dial Transplant 22(2):592-596.

Shenker, B.J. et al. (Dec. 1991). "Immunosuppressive effects of Prevotella intermedia on in vitro human lymphocyte activation," Infect Immun 59(12):4583-4589.

Shin, et al. An increase in the *Akkermansia* spp. population induced by metformin treatment improves glucose homeostasis in diet-induced obese mice. Gut. May 2014;63(5):727-35. doi: 10.1136/gutjnl-2012-303839. Epub Jun. 26, 2013.

Simpson, A. et al. (Jun. 1, 2010, e-published Feb. 18, 2010). "Beyond atopy: multiple patterns of sensitization in relation to asthma in a birth cohort study," Am J Respir Crit Care Med 181(11):1200-1206.

Sokol et al. 'Faecalibacterium prausnitzii is ananti-inflammatory commensal bacterium identified by gut microbiota analysis ofCrohn disease patients.' Proceedings of the National Academy of Sciences. 2008,vol. 105, No. 43, pp. 6731-16736. Epub Oct. 20, 2008.

Stenman, et al. (Feb. 2016, e-published Nov. 13, 2015). "Establishing a causal link between gut microbes, body weight gain and glucose metabolism in humans—towards treatment with probiotics," Benef Microbes 7(1):11-22.

Stokholm, et al., Maturation of the gut microbiome and risk of asthma in childhood. Nature Communications, 2018; 9(141): 1-10.

Thomsen, S.F. Epidemiology and natural history of atopic diseases. European Clinical Respiratory Journal. 2015;2(1):24642. doi:10.3402/ecrj.v2.24642.

Totani, Y. et al. (Jan. 2000). "Leukotoxin and its diol induce neutrophil chemotaxis through signal transduction different from that of fMLP," Eur Respir J15(1):75-79.

Trompette, et al. Gut microbiota metabolism of dietary fiber influences allergic airway disease and hematopoiesis. Nat Med. 2014;20(2):159-166. doi:10.1038/nm.3444.

U.S. Appl. No. 15/946,031 Notice of Allowance dated Mar. 12, 2020.

U.S. Appl. No. 15/946,031 Office Action dated Dec. 17, 2018.
U.S. Appl. No. 15/946,031 Office Action dated Jun. 18, 2019.
U.S. Appl. No. 15/946,031 Office Action dated Nov. 22, 2019.
U.S. Appl. No. 16/551,478 Office Action dated Jun. 18, 2020.
U.S. Appl. No. 16/551,478 Office Action dated Feb. 4, 2020.

Vutcovivi, et al. Inflammatory bowel disease and airway diseases. World journal of gastroenterology 22.34 (2016): 7735-7741.

Walmsley, R.S. et al. (Jul. 1998). "A simple clinical colitis activity index," 43(1):29-32.

Walters, J.D. et al. (May 1995). "Polyamines found in gingival fluid enhance the secretory and oxidative function of human polymorphonuclear leukocytes in vitro," J Periodontal Res 30(3):167-171.

Weingarden, A.R. et al. (Feb. 15, 2014, e-published Nov. 27, 2013). "Microbiota transplantation restores normal fecal bile acid composition in recurrent Clostridium difficile infection," Am J Physiol Gastrointest Liver Physiol 306(4):G310-G319.

Wenzel, S.E., Asthma phenotypes: the evolution from clinical to molecular approaches, Nature medicine, May 2012; 18(5):716-725.

Wopereis, et al. The first thousand days—intestinal microbiology of early life: establishing a symbiosis. Pediatr Allergy Immunol. 2014;25(5):428-438. doi:10.1111/pai.12232.

Written Opinion dated Jun. 9, 2017, for PCT Application No. PCT/US2017/020809, filed Mar. 3, 2017, 11 pages.

Yatsunenko, T. et al. (May 9, 2012). "Human gut microbiome viewed across age and geography," Nature 486(7402):222-227.

Young, D. et al. (Feb. 2012, e-published Dec. 21, 2011). "Soy-derived di- and tripeptides alleviate colon and ileum inflammation in pigs with dextran sodium sulfate-induced colitis," J Nutr 142(2):363-368.

Zhang, W. et al. (Dec. 2013). "Soluble epoxide hydrolase deficiency inhibits dextran sulfate sodium-induced colitis and carcinogenesis in mice," 33(12):5261-5271.

Zheng, et al. The atopic march: progression from atopic dermatitis to allergic rhinitis and asthma. Allergy Asthma Immunol Res. 2011;3(2):67-73. doi:10.4168/aair.2011.3.2.67.

Zwolinska-Wcislo et al. (Mar. 2009). "Effect of Candida colonization on human ulcerative colitis and the healing of inflammatory changes of the colon in the experimental model of colitis ulcerosa," J Physiol Pharmacol 60(1):107-118.

Yang, et al. Treatment of allergic rhinitis with probiotics: an alternative approach. North American journal of medical sciences 5.8 (2013): 465-468.

Cemerski et al. Suppression of mast cell degranulation through a dual-targeting tandem IgE-IgG Fc domain biologic engineered to bind with high affinity to FcγRIIb. Immunology letters vol. 143,1 (2012): 34-43. doi:10.1016/j.imlet.2012.01.008.

Co-pending U.S. Application No. 202117233194, inventors Lynch; Susan V. et al., filed on Apr. 16, 2021.

PCT International Search Report and Written Opinion, PCT Application No. PCT/US2020/019124, dated Jul. 29, 2020, 21 pages.

PCT/US2020/054444 International Search Report dated Feb. 1, 2021.

U.S. Appl. No. 16/551,478 Notice of Allowance dated Mar. 10, 2021.

Extended European Search Report in EP Application No. 19785325.2 dated Oct. 21, 2021.

Koh, A. et al., "From Dietary Fiber to Host Physiology: Short-Chain Fatty Acids as Key Bacterial Metabolites", Cell, Jun. 2, 2016, vol. 165, No. 6, pp. 1332-1345.

U.S. Appl. No. 17/475,228 Office Action dated Dec. 6, 2021.

\* cited by examiner

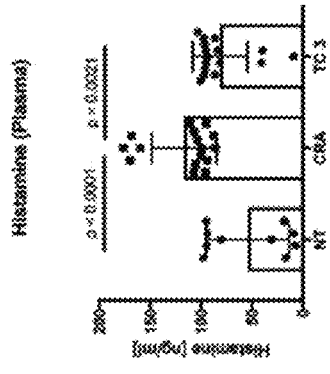
FIG. 1A
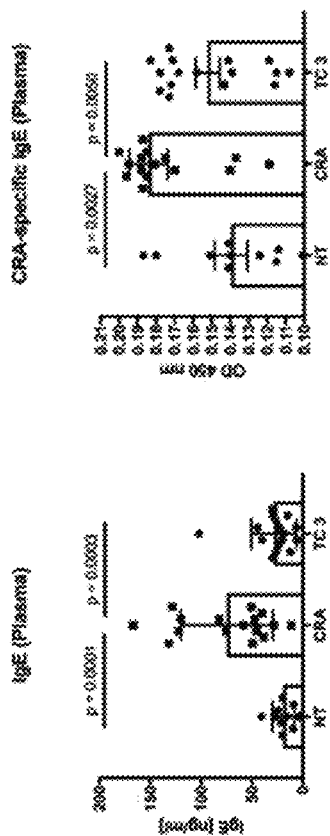
FIG. 1D
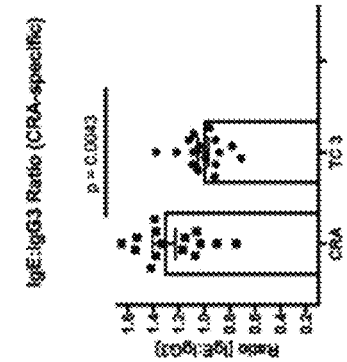
FIG. 1B
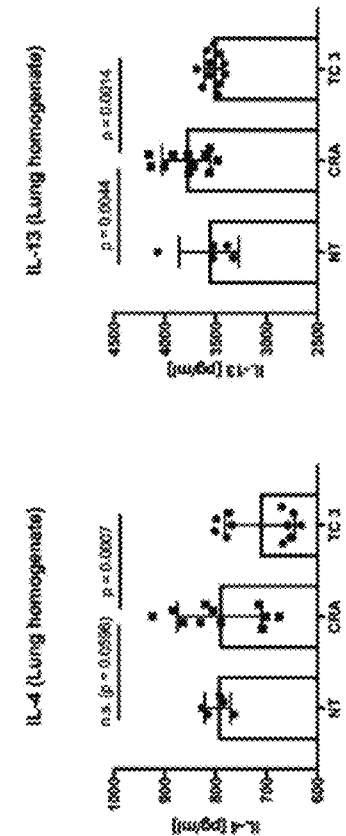
FIG. 1E
FIG. 1C
FIG. 1F

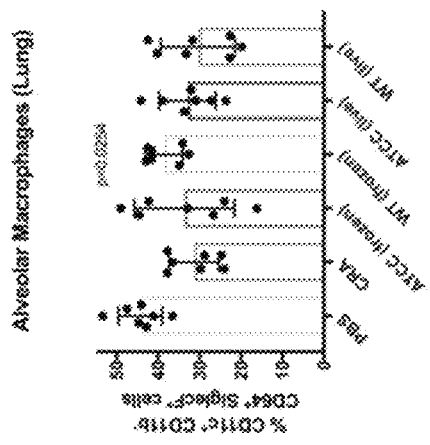
FIG. 2E
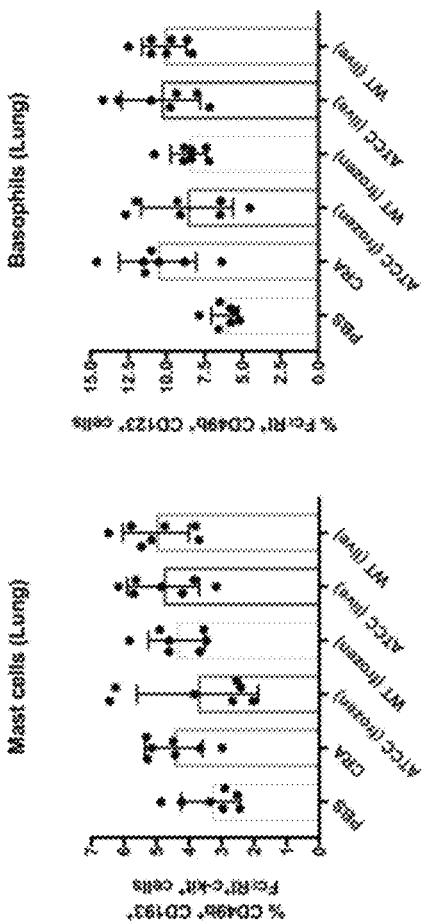
FIG. 2B
FIG. 2A
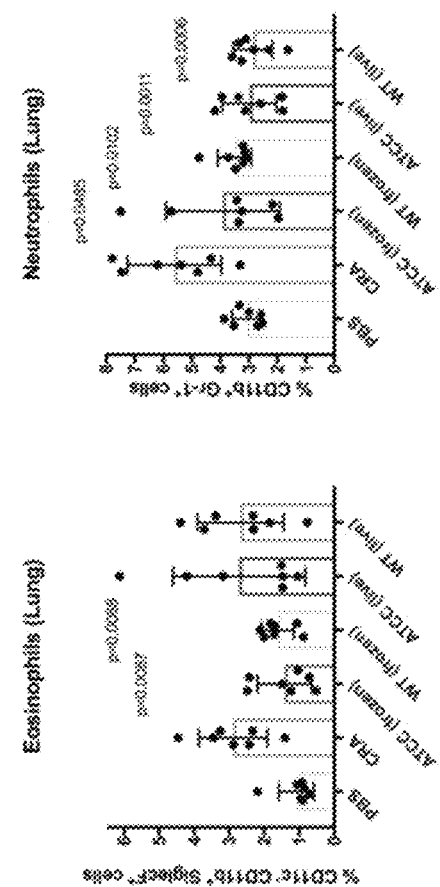
FIG. 2D
FIG. 2C

FIG. 6

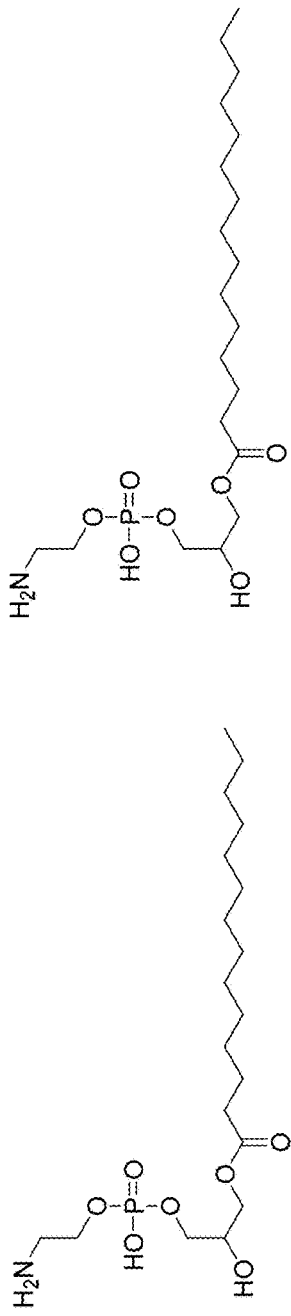
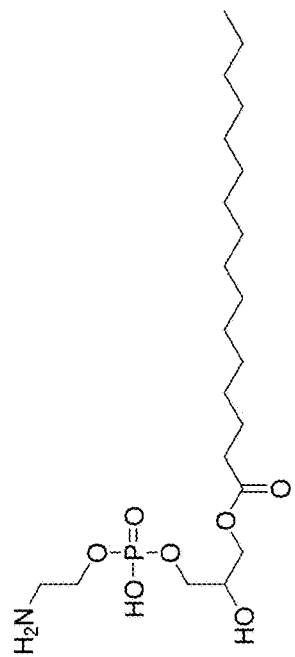
FIG. 13

| Antibiotic Tested (Class) | MIC Interpretive criteria* | *L. crispatus* ST100 MIC (μg/ml) | *A. muciniphila* ST7 MIC (μg/ml) | *F. prausnitzii* ST38 MIC (μg/ml) |
|---|---|---|---|---|
| Amikacin (aminoglycoside) | Sensitive (≤ 16 μg/ml) ; Intermediate (32 μg/ml); Resistant (≥ 64 μg/ml) | >64 Resistant | >64 Resistant | 32 Intermediate |
| Amoxycillin/Clavulinic acid (beta-lactam with beta-lactamase inhibitor) | Sensitive (≤ 8/4 μg/ml) ; Intermediate (16/8 μg/ml); Resistant (≥ 32/16 μg/ml) | >32 Resistant | >32 Resistant | >32 Resistant |
| Ampicillin (beta-lactam) | Sensitive (≤ 8 μg/ml) ; Intermediate (16 μg/ml); Resistant (≥ 32 μg/ml) | 2 Sensitive | >32 Resistant | >32 Resistant |
| Azithromycin (macrolide) | Sensitive (≤ 2 μg/ml); Intermediate (4 μg/ml); Resistant (≥ 8 μg/ml) | 0.5 Sensitive | 0.125 Sensitive | <0.125 Sensitive |
| Bacitracin (cyclic polypeptides) | No Information on CLSI | 8 | >64 | 4 |
| Ceftriaxone (cephalosporin) | Sensitive (≤ 1 μg/ml) ; Intermediate (2 μg/ml); Resistant (≥ 4 μg/ml) | 4 Resistant | > 4 Resistant | >4 Resistant |
| Clindamycin (lincosamide) | Sensitive (≤ 0.5μg/ml) ; Intermediate (1-2 μg/ml); Resistant (≥ 4 μg/ml) | < 0.125 μg/ml Sensitive | 1 μg/ml Intermediate | < 0.125 μg/ml Sensitive |
| Levofloxacin (floroquinolone) | Sensitive (≤ 2 μg/ml) ; Intermediate (4 μg/ml); Resistant (≥ 8 μg/ml) | > 8 Resistant | > 8 Resistant | > 8 Resistant |
| Tetracycline (protein synthesis inhibitor) | Sensitive (≤ 4 μg/ml) ; Intermediate (8 μg/ml); Resistant (≥ 16 μg/ml) | 2 Sensitive | 1 Sensitive | <0.25 Sensitive |
| Vancomycin (non-ribosomal peptide) | Sensitive (≤ 2 μg/ml) ; Intermediate (4-8 μg/ml); Resistant (≥ 16 μg/ml) | 1 Sensitive | >16 Resistant | 1 Sensitive |

MICROBIAL CONSORTIA

CROSS-REFERENCE TO RELATED APPLICATION

This application is a continuation application of PCT application serial number PCT/US2019/026674, filed Apr. 9, 2019, which claims the benefit of U.S. Provisional Application No. 62/655,562, filed Apr. 10, 2018, which are hereby incorporated by reference in their entireties and for all purposes.

BACKGROUND

Recent developments in the areas of microbiome and genome research provide evidence that the microbial composition of the human gut fundamentally influences human health, disease onset and progression. However, much remains unknown with regards to the microbiome-host relationships, functional and metabolic changes in host due to the microbiome composition, as well as the potential development of microbial compositions for therapeutic applications.

SUMMARY

The present disclosure provides compositions, methods and kits comprising one or more bacterial strains useful for the prevention and/or treatment of a disease or condition in a subject (e.g., a rodent or a human). In some cases, a composition comprising the at least one bacterial strain can be administered orally, and can be administered in combination with one or more pharmaceutically acceptable excipients. In some cases, a therapeutic bacterial consortium (e.g., comprising an *Akkermansia muciniphila* strain, *Faecalibacterium prausnitzii* strain, *Lactobacillus crispatus* strain) of the present disclosure can be administered to a subject in combination with one or more other therapeutic agents (e.g., small molecule drug, therapeutic peptides or proteins, etc.).

In various aspects, the present disclosure provides a method of treating inflammation or an inflammatory disease in a subject in need thereof, comprising administering to the subject an effective amount of a bacterial population comprising one or more bacterial strains of Table 1. In some cases, the one or more bacterial strains of Table 1 comprise one or more bacterial strains associated with isolate numbers 1-4. In some cases, the one or more bacterial strains of Table 1 comprise one or more bacterial strains associated with isolate numbers 5-40. In some cases, the one or more bacterial strains of Table 1 comprise one or more bacterial strains associated with isolate numbers 184-199. In some cases, the one or more bacterial strains of Table 1 comprise one or more bacterial strains associated with isolate numbers 214-216. In some cases, the one or more bacterial strains of Table 1 comprise one or more bacterial strains associated with isolate numbers 223-226. In some cases, the one or more bacterial strains of Table 1 comprise one or more bacterial strains associated with isolate numbers 111-115. In some cases, the inflammatory disease is an allergy, atopy, asthma, an autoimmune disease, an autoinflammatory disease, a hypersensitivity, pediatric allergic asthma, allergic asthma, inflammatory bowel disease, Celiac disease, Crohn's disease, colitis, ulcerative colitis, collagenous colitis, lymphocytic colitis, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behcet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, or atopic dermatitis. In some cases, the subject is less than about 24 months old. In some cases, the subject is a neonate.

In various aspects, the present disclosure provides a method of treating dysbiosis in a subject in need thereof, comprising administering to the subject an effective amount of a bacterial population comprising one or more bacterial strains of Table 1. In some cases, the one or more bacterial strains of Table 1 comprise one or more bacterial strains associated with isolate numbers 1-4. In some cases, the one or more bacterial strains of Table 1 comprise one or more bacterial strains associated with isolate numbers 5-40. In some cases, the one or more bacterial strains of Table 1 comprise one or more bacterial strains associated with isolate numbers 184-199. In some cases, the one or more bacterial strains of Table 1 comprise one or more bacterial strains associated with isolate numbers 214-216. In some cases, the one or more bacterial strains of Table 1 comprise one or more bacterial strains associated with isolate numbers 223-226. In some cases, the one or more bacterial strains of Table 1 comprise one or more bacterial strains associated with isolate numbers 111-115. In some cases, the subject is less than about 24 months old. In some cases, the subject is a neonate.

In various aspects, the present disclosure provides s method of treating a viral respiratory infection in a subject in need thereof, comprising administering to the subject an effective amount of a bacterial population comprising one or more bacterial strains of Table 1. In some cases, the one or more bacterial strains of Table 1 comprise one or more bacterial strains associated with isolate numbers 1-4. In some cases, the one or more bacterial strains of Table 1 comprise one or more bacterial strains associated with isolate numbers 5-40. In some cases, the one or more bacterial strains of Table 1 comprise one or more bacterial strains associated with isolate numbers 184-199. In some cases, the one or more bacterial strains of Table 1 comprise one or more bacterial strains associated with isolate numbers 214-216. In some cases, the one or more bacterial strains of Table 1 comprise one or more bacterial strains associated with isolate numbers 223-226. In some cases, the one or more bacterial strains of Table 1 comprise one or more bacterial strains associated with isolate numbers 111-115. In some cases, the subject is less than about 24 months old. In some cases, the subject is a neonate. In some cases, the bacterial population is formulated as an oral dosage form. In some cases, said oral dosage form further comprises an excipient. In some cases, said excipient comprises an excipient that consumes oxygen. In some cases, said oral dosage form is in the form of a drop, a liquid, a frozen liquid, a suspension, an emulsion or a powder. In some cases, the bacterial population produces one or more biologically active compounds. In some cases, the one or more biologically active compounds comprise one or more fatty acids, one or more lipids, one or more phospholipids, a derivative of any of the above, or any combination thereof. In some cases, the one or more fatty acids comprise short-chain fatty acids. In some cases, the one or more phospholipids comprise one or more phosphatidylcholines, or one or more derivatives thereof.

In various aspects, the present disclosure provides a composition comprising one or more bacterial strains of Table 1. In some cases, such composition can further comprise at least about $10^7$ cells of said one or more bacterial strains of Table 1. In some cases, the composition can further comprise from about $10^7$ to about $10^{11}$ cells, or from about $10^8$ cells to about $10^9$ cells of said one or more bacterial strains of Table 1. In some cases, the composition comprises three or more bacterial strains of Table 1. In some cases, said three or more bacterial strains of Table 1 act synergistically. In some cases, said composition comprises four or more bacterial strains of Table 1. In some cases, said four or more bacterial strains of Table 1 act synergistically. In some cases, said composition comprises five or more bacterial strains of Table 1. In some cases, said five or more bacterial strains of Table 1 act synergistically. In some cases, said three or more bacterial strains of Table 1 are substantially pure. In some cases, the composition comprises at least one strain of *Lactobacillus johnsonii* or *Lactobacillus crispatus*, at least one strain of *Faecalibacterium prausnitzii*, and at least one strain of *Akkermansia muciniphila*, and optionally at least one strain of a *Bifidobacterium*. In some cases, the composition comprises two or more distinct strains of *Lactobacillus crispatus*. In some cases, the composition comprises two or more distinct strains of *Faecalibacterium prausnitzii*. In some cases, the composition comprises two or more distinct strains of *Akkermansia muciniphila*. In some cases, the composition comprises two or more distinct strains of a *Bifidobacterium*.

In various aspects, the present disclosure provides a composition comprising three or more bacterial species of Table 1, wherein said composition comprises three or more bacterial strains of Table 1.

In various aspects, the present disclosure provides a composition comprising four or more bacterial species of Table 1, wherein said composition comprises four or more bacterial strains of Table 1.

In various aspects, the present disclosure provides a composition comprising one or more strains of *Lactobacillus* sp., *Faecalibacterium* sp., or *Akkermansia* sp., which one or more strains are from Table 1. In some cases, said composition comprises strains of two or more of *Lactobacillus* sp., *Faecalibacterium* sp., and *Akkermansia* sp., which strains are from Table 1. In some cases, said composition comprises strains of *Lactobacillus* sp., *Faecalibacterium* sp., and *Akkermansia* sp., which strains are from Table 1. In some cases, said composition comprises any one of the strains *Akkermansia muciniphila* ST7, *Faecalibacterium prausnitzii* ST38, and *Lactobacillus crispatus* ST100, or any combination thereof. In some cases, said composition comprises the strains *Akkermansia muciniphila* ST7, *Faecalibacterium prausnitzii* ST38, and *Lactobacillus crispatus* ST100. In some cases, the composition produces one or more biologically active compounds. In some cases, the one or more biologically active compounds comprise one or more fatty acids, one or more lipids, one or more phospholipids, a derivative of any of the above, or any combination thereof. In some cases, the one or more fatty acids comprise short-chain fatty acids. In some cases, the one or more phospholipids comprise one or more phosphatidylcholines, or one or more derivatives thereof. In some cases, said composition is formulated as an oral dosage form. In some cases, said oral dosage form further comprises an excipient. In some cases, said excipient comprises an excipient that consumes oxygen. In some cases, said oral dosage form is in the form of a drop, a liquid, a frozen liquid, a suspension, an emulsion or a powder.

In various aspects, the present disclosure provides a container comprising a composition comprising one or more bacterial strains of Table 1. In some cases, such container comprises a composition comprising one or more of any one of the strains shown in Table 1. In some cases, said composition is formulated in an aerosol, vapor, spray, or mist.

In various aspects, the present disclosure provides a kit comprising (1) a container comprising a composition comprising one or more bacterial strains of Table 1, and (2) instructions directing a user to use said composition. In some cases, the kit comprises a container as described herein. In some cases, such container can be used for treating inflammation or an inflammatory disease in a subject in need thereof.

Additional aspects and advantages of the present disclosure will become readily apparent to those skilled in this art from the following detailed description, wherein only illustrative embodiments of the present disclosure are shown and described. As will be realized, the present disclosure is capable of other and different embodiments, and its several details are capable of modifications in various obvious respects, all without departing from the disclosure. Accordingly, the drawings and description are to be regarded as illustrative in nature, and not as restrictive.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

FIG. 1A shows IgE concentration values (in ng/mL) in mouse plasma obtained from three independent studies using the cockroach allergen (CRA) murine model. Non-treated (NT) mice, cockroach allergen (CRA) treated mice, and mice treated with CRA and an oral supplementation containing the microbial consortium (e.g., the therapeutic consortium abbreviated as "TC3") consisting of *Lactobacillus johnsonii, Faecalibacterium prausnitzii*, and *Akkermansia muciniphila* were used, in accordance with the present disclosure.

FIG. 1B shows CRA-specific IgE concentration values (determined by measuring the optical density at 450 nm) in mouse plasma obtained from three independent studies in NT mice, CRA treated mice, and mice treated with CRA and an oral TC3 supplementation, in accordance with the present disclosure.

FIG. 1C shows histamine concentration values (in ng/mL) in mouse plasma obtained from three independent studies in NT mice, CRA treated mice, and mice treated with CRA and an oral TC3 supplementation, in accordance with the present disclosure.

FIG. 1D shows IL-4 concentration values (in pg/mL) in mouse lung homogenate obtained from three independent studies in NT mice, CRA treated mice, and mice treated with CRA and an oral TC3 supplementation, in accordance with the present disclosure.

FIG. 1E shows IL-13 concentration values (in pg/mL) in mouse lung homogenate obtained from three independent studies in NT mice, CRA treated mice, and mice treated with CRA and an oral TC3 supplementation, in accordance with the present disclosure.

FIG. 1F shows plasma concentration ratios of CRA-specific IgE to CRA-specific IgG3 obtained from three independent studies in NT mice, CRA treated mice, and mice treated with CRA and an oral TC3 supplementation, in accordance with the present disclosure.

FIG. 2A shows the relative percentage of mast cells ($CD49b^+$, $CD193^+$, $Fc\epsilon RI^+$, $c-kit^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.

FIG. 2B shows the relative percentage of basophils ($CD49b^+$, $CD123^+$, $Fc\epsilon RI^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.

FIG. 2C shows the relative percentage of eosinophils ($CD11c^-$, $CD11b^+$, $SiglecF^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.

FIG. 2D shows the relative percentage of neutrophils ($CD11b^+$, $Gr-1^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.

FIG. 2E shows the relative percentage of alveolar macrophages ($CD11c^+$, $CD11b^-$, $CD64^+$, $SiglecF^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.

FIG. 6 shows a table summarizing comparative SNP data between various *A. muciniphila* strains.

FIG. 13 shows proposed structures of phosphatidylcholine precursor or phosphatidylcholine-like compounds 1-3.

FIG. 14 shows a summary table of antibiotic resistance results of the three strains *A. muciniphila* ST7, *Faecalibacterium prausnitzii* ST38, and *Lactobacillus crispatus* ST100 (* denotes values as recommended by the Clinical and Laboratory Standards Institute). Antibiotic resistance was determined using the broth solution method.

DETAILED DESCRIPTION

Figures 1G, 1H:
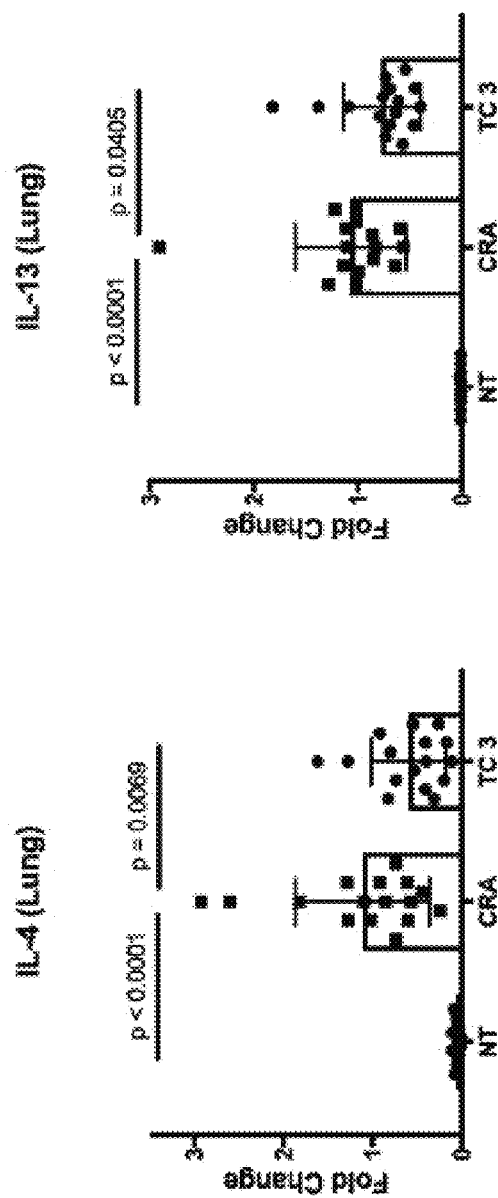
FIG. 1G shows the fold change of IL-4 concentration in lung tissue determined via qPCR and obtained from three independent studies in NT mice, CRA treated mice, and mice treated with CRA and an oral TC3 supplementation, in accordance with the present disclosure.
FIG. 1H shows the fold change of IL-13 concentration in lung tissue determined via qPCR and obtained from three independent studies in NT mice, CRA treated mice, and mice treated with CRA and an oral TC3 supplementation, in accordance with the present disclosure.
Figure 1I:
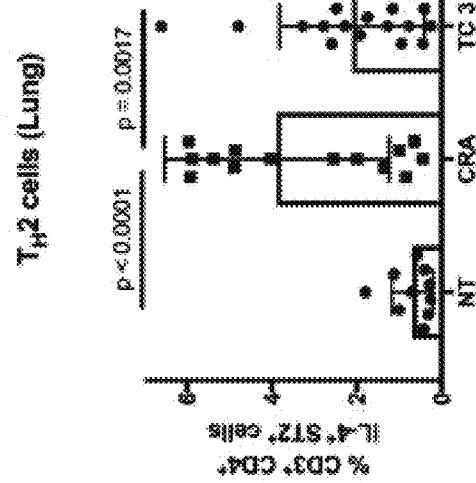
FIG. 1I shows the relative percentage of regulatory T ($T_{reg}$) cells ($CD4^+$, $CD127^-$, $CD25^+$, $Foxp3^+$ cells) in lung tissue obtained from three independent studies in NT mice, CRA treated mice, and mice treated with CRA and an oral TC3 supplementation, in accordance with the present disclosure.
Figure 1J:
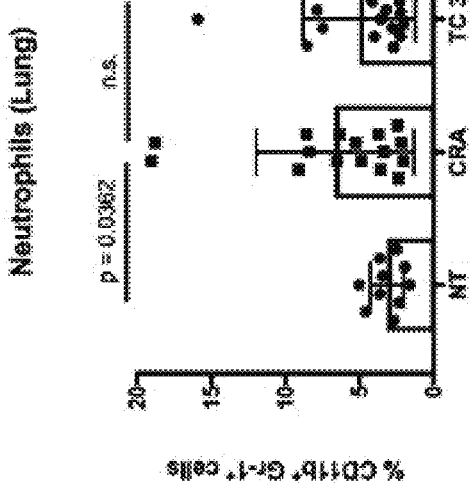
FIG. 1J shows the relative percentage of type 2 T helper ($T_H2$) cells ($CD3^+$, $CD4^+$, $IL-4^+$, $ST2^+$ cells) in lung tissue obtained from three independent studies in NT mice, CRA treated mice, and mice treated with CRA and an oral TC3 supplementation, in accordance with the present disclosure.
Figure 1K:
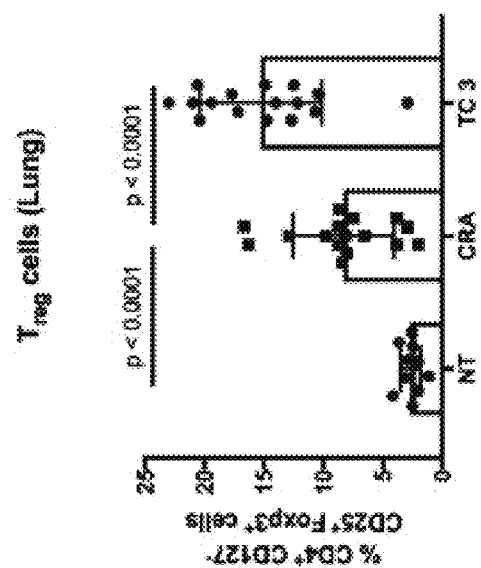
FIG. 1K shows the relative percentage of eosinophils ($CD11c^-$, $CD11b^+$, $SiglecF^+$ cells) in lung tissue obtained from three independent studies in NT mice, CRA treated mice, and mice treated with CRA and an oral supplementation containing TC3, in accordance with the present disclosure.
Figure 1L:
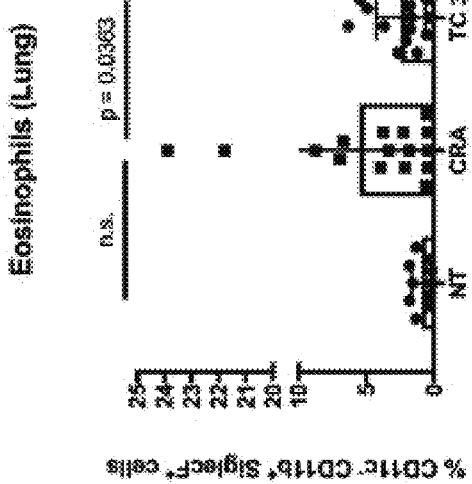
FIG. 1L shows the relative percentage of neutrophils ($CD11b^+$, $Gr-1^+$ cells) in lung tissue obtained from three independent studies in NT mice, CRA treated mice, and mice treated with CRA and an oral TC3 supplementation, in accordance with the present disclosure.

While various embodiments of the invention have been shown and described herein, it will be obvious to those skilled in the art that such embodiments are provided by way of example only. Numerous variations, changes, and substitutions may occur to those skilled in the art without departing from the invention. It should be understood that various alternatives to the embodiments of the invention described herein may be employed.

The present disclosure provides methods and compositions comprising microbial compositions, such as therapeutic microbial consortia. The microbial compositions described herein can comprise one or more different bacterial species (e.g., *Akkermansia* sp., *Faecalibacterium* sp., *Lactobacillus* sp., and/or those listed in Table 1) and/or one or more different bacterial strains (e.g., any one or more of those listed in Table 1 (strains listed as isolated numbers) and/or Table 2 (strains listed as isolated numbers and strain numbers)). Such microbial compositions can have beneficial and/or therapeutic properties and hence can be used to prevent and/or treat a broad spectrum of diseases or disorders in a subject (e.g., a rodent or a human) upon administration to said subject. The microbial compositions described herein can be administered using various administration routes, including administration as an oral dosage form (e.g., a capsule, a tablet, an emulsion, suspension, etc.).

A microbial composition described herein can comprise any one or more of the bacterial species *Akkermansia* sp., *Faecalibacterium* sp., *Lactobacillus* sp., or any combination thereof. A microbial composition can comprise strains *A. muciniphila* ST7, *F. prausnitzii* ST38, or *L. crispatus* ST100, or any combination thereof. A microbial composition can be a synergistic bacterial consortium. Synergistic effects of such a consortium can include increased therapeutic efficacy in a subject and/or beneficial long-term health effects (e.g., prevention of diseases or conditions) for said subject. A microbial composition of the present disclosure can comprise one or more bacterial species and/or strains that can produce one or more beneficial and/or therapeutically effective compounds. Such compounds can have anti-inflammatory effects. The compositions and methods described herein can comprise one or more bacterial cells of one or more bacterial species or strains that produce beneficial fatty acids including short-chain fatty acids (SCFAs), saturated and unsaturated fatty acids such as omega-3 and/or omega-6 fatty acids (e.g., linolenic acid), and/or effect or alter a metabolism of such fatty acids. The compositions and methods described herein can comprise one or more bacterial cell of one or more bacterial species or strains that produce and/or affect or alter the metabolism of phospholipids and/or derivatives thereof. Such phospholipid and/or derivative thereof can be a phosphatidylcholine and/or a derivative thereof. The present disclosure provides one or more species or strains of *Akkermansia* sp. that can produce one or more phospholipids (e.g., phosphatidylcholine(s) and/or derivative(s) thereof) and/or derivatives thereof. The *Akkermansia* strain that produces one or more phospholipids can be *A. muciniphila* ST7. At least one of the phospholipids that can be produced by *A. muciniphila* ST7 can be a phosphatidylcholine and/or a derivative thereof. Such compounds can have structural similarity with compounds 1-3 shown in FIG. 14.

The therapeutic consortia described herein can be used to treat and/or prevent diseases and conditions such as dysbiosis, inflammation (e.g., chronic and/or allergic inflammation), autoimmune disorders, infections, and/or cancer.

Whenever the term "at least," "greater than," or "greater than or equal to" precedes the first numerical value in a series of two or more numerical values, the term "at least," "greater than" or "greater than or equal to" applies to each of the numerical values in that series of numerical values. For example, greater than or equal to 1, 2, or 3 is equivalent to greater than or equal to 1, greater than or equal to 2, or greater than or equal to 3.

Whenever the term "no more than," "less than," or "less than or equal to" precedes the first numerical value in a series of two or more numerical values, the term "no more than," "less than," or "less than or equal to" applies to each of the numerical values in that series of numerical values. For example, less than or equal to 3, 2, or 1 is equivalent to less than or equal to 3, less than or equal to 2, or less than or equal to 1.

As used herein, a substance is "pure" or "substantially pure" if it is substantially free of other components. The terms "purify," "purifying" and "purified", when applied to a bacterium, can refer to a bacterium that has been separated from at least some of the components with which it was associated either when initially produced or generated (e.g., whether in nature or in an experimental setting), or during any time after its initial production. A bacterium or a bacterial population may be considered purified if it is isolated at or after production, such as from a material or environment containing the bacterium or bacterial population, or by passage through culture, and a purified bacterium or bacterial population may contain other materials up to at least about 10%, about 20%, about 30%, about 40%, about 50%, about 60%, about 70%, about 80%, about 90%, or above about 90% and still be considered "isolated." Purified bacteria and bacterial populations can be more than at least about 80%, about 85%, about 90%, about 91%, about 92%, about 93%, about 94%, about 95%, about 96%, about 97%, about 98%, about 99%, or more than at least about 99% pure by weight (w/w). In the instance of microbial compositions provided herein, the one or more bacterial types (species or strains) present in the composition can be independently purified from one or more other bacteria produced and/or present in the material or environment containing the bacterial type. Microbial compositions and the bacterial components thereof are generally purified from residual habitat products.

An isolated bacterium may have been (1) separated from at least some of the components with which it was associated when initially obtained (whether in nature or in an experimental setting), and/or (2) produced, prepared, purified, and/or manufactured by the hand of man, e.g. using artificial culture conditions such as (but not limited to) culturing on a plate and/or in a fermenter. Isolated bacteria can include those bacteria that are cultured, even if such cultures are not monocultures. Isolated bacteria can be separated from at least about 10%, about 20%, about 30%, about 40%, about 50%, about 60%, about 70%, about 80%, about 90%, or more of the other components with which they were initially associated. Isolated bacteria can be more than about 80%, about 85%, about 90%, about 91%, about 92%, about 93%, about 94%, about 95%, about 96%, about 97%, about 98%, about 99%, or more than about 99% pure. A bacterial population of a biological sample provided herein can comprise one or more bacteria, which may then be isolated from such sample. Isolated bacteria may be provided in a form that is not naturally occurring.

As used herein, the terms "effective amount" and "effective dosage" can be used interchangeably, and generally refer to an amount necessary to produce a desired physiologic response (e.g., reduction of inflammation, infection, or dysbiosis). Effective amounts and schedules for administering a therapeutic consortium may be determined empirically. The dosage ranges for administration can be large enough to produce the desired effect in which one or more symptoms of the disease or disorder are affected (e.g., reduced or delayed). The dosage may not be so large as to cause substantial adverse side effects, such as cross-reactions, anaphylactic reactions, and the like. Generally, the dosage will vary with the age, condition, sex, type of disease, the extent of the disease or disorder, route of administration, or whether other drugs are included in the regimen, and can be determined. The dosage can be adjusted in the event of any contraindications. Dosages can vary and can be administered in one or more dose administrations daily, for one or several days. For example, for the given parameter, an effective amount will show an increase or decrease of at least about 5%, 10%, 15%, 20%, 25%, 40%, 50%, 60%, 75%, 80%, 90%, or at least 100%. Efficacy can also be expressed as "-fold" increase or decrease. For example, a therapeutically effective amount can have at least about a 1.2-fold, 1.5-fold, 2-fold, 5-fold, or more effect over a control. For prophylactic use, a therapeutically effective amount of the microbial compositions described herein are administered to a subject prior to or during early onset (e.g., upon initial signs and symptoms of an autoimmune disease).

As used herein, the terms "subject," "patient," "individual," etc. can be generally interchanged. In addition, an individual described as a "patient" may not have a given disease, but may be merely seeking medical advice As used herein, "treating" or treatment of a condition, disease or disorder or symptoms associated with a condition, disease or disorder refers to an approach for obtaining beneficial results, including clinical results. Beneficial clinical results can include, but are not limited to, alleviation or amelioration of one or more symptoms or conditions, diminishment of extent of condition, disorder or disease, stabilization of the state of condition, disorder or disease, prevention of development of condition, disorder or disease, prevention of spread of condition, disorder or disease, delay or slowing of condition, disorder or disease progression, delay or slowing of condition, disorder or disease onset, amelioration or palliation of the condition, disorder or disease state, and remission, whether partial or total. "Treating" can also mean prolonging survival of a subject beyond that expected in the absence of treatment. "Treating" can also mean inhibiting the progression of the condition, disorder or disease, slowing the progression of the condition, disorder or disease temporarily, although in some instances, it can involve halting the progression of the condition, disorder or disease permanently. As used herein the terms treatment, treat, or treating refers to a method of reducing the effects of one or more symptoms of a disease or condition characterized by expression of the protease or symptom of the disease or condition characterized by expression of the protease. Thus, the herein disclosed methods or treatments can refer to at least about a 10%, 20%, 30%, 40%, 50%, 60%, 70%, 80%, 90%, or 100% reduction in the severity of an established disease, condition, or symptom of the disease or condition (e.g., inflammation, infection, or dysbiosis). For example, a method for treating a disease is considered to be a treatment if there is a 10% reduction in one or more symptoms of the disease in a subject as compared to a control. Thus, the reduction can be at least about 10%, 20%, 30%, 40%, 50%, 60%, 70%, 80%, 90%, 100%, or any percent reduction in between about 10% and about 100% as compared to native or control levels. Further, as used herein, references to decreasing, reducing, or inhibiting include a change of at least about 10%, 20%, 30%, 40%, 50%, 60%, 70%, 80%, 90% or greater as compared to a control level and such terms can include but do not necessarily include complete elimination. Compositions comprising a defined microbial compositions can be administered to the gastrointestinal tract of a subject by nasoduodenal catheter, by enema, or by endoscopy, enteroscopy, or colonoscopy or orally in a consumable capsule, pill, solution, suspension, etc. A therapeutic microbial composition can be diluted in a suitable excipient (e.g., comprising saline solution, buffer, etc.).

As described herein, the terms "disease" and "condition" can be used interchangeably herein and generally refer to a state of being or health status of a patient or subject capable of being diagnosed and/or treated with a kit, method and/or composition disclosed herein. A disease can be an inflammatory disease, an infectious disease, or an autoimmune disease. A disease can be or can be associated with a microbiome of a subject, such as an intestinal microbiome. A disease can be a dysbiosis, such as gut dysbiosis.

As described herein, the term "dysbiosis" can mean a difference in the gastrointestinal microbiota compared to a healthy or general population. Dysbiosis can comprise a difference in gastrointestinal microbiota commensal species diversity compared to a healthy or general population. Dysbiosis can also comprise a decrease of beneficial microorganisms and/or increase of pathobionts (pathogenic or potentially pathogenic microorganisms) and/or decrease of overall microbiota species diversity. Many factors can harm the beneficial members of the intestinal microbiota leading to dysbiosis, including (but not limited to) antibiotic use, psychological and physical stress, radiation, and dietary changes. Dysbiosis can comprise and/or promote the overgrowth of a bacterial opportunistic pathogen such as *Enterococcus faecalis*, *Enterococcus faecium*, or *Clostridium difficile*. A dysbiosis can comprise a reduced amount (absolute number or proportion of the total microbial population) of bacterial or fungal cells of a species or genus (e.g., at least about 5%, 10%, 15%, 20%, 25%, 30%, 35%, 40%, 45%, 50%, 55%, 60%, 65%, 70%, 75%, 80%, 85%, 90%, 95% or more lower) compared to a healthy subject (e.g., a corresponding subject who does not have an inflammatory disease, an infection, and who has not been administered an antibiotic within about 1, 2, 3, 4, 5, or 6 months, and/or compared to a healthy or general population). The dysbiosis comprises an increased amount (absolute number or proportion of the total microbial population) of bacterial or fungal cells within a species or genus (e.g., at least about 5%, 10%, 15%, 20%, 25%, 30%, 35%, 40%, 45%, 50%, 55%, 60%, 65%, 70%, 75%, 80%, 85%, 90%, 95% or more higher) compared to a healthy subject (e.g., a corresponding subject who does not have an inflammatory disease, an infection, and who has not been administered an antibiotic within about 1, 2, 3, 4, 5, or 6 months, and/or compared to a healthy or general population). A subject who comprises a gastrointestinal infection, gastrointestinal inflammation, diarrhea, colitis, or who has received an antibiotic within about 1, 2, 3, 4, 5, 6, 7, 8, 9, or 10 weeks can be deemed to comprise dysbiosis. An impaired microbiota can comprise small intestinal bacterial or fungal overgrowth. Antibiotic administration (e.g., systemically, such as by intravenous injection or orally) can be a common and significant cause of major alterations in the normal microbiota. Thus, as used herein, the term "antibiotic-induced dysbiosis can refer to dysbiosis caused by or following the administration of an antibiotic. Dysbiosis can be associated with various diseases and conditions such as inflammation (e.g., chronic and/or allergic inflammation), auto-immune disorders, infections, and/or cancer. Thus, a subject suffering from dysbiosis can have an inflammatory disease (e.g., chronic and/or allergic inflammatory disease), auto-immune disorders, infections, and/or cancer.

As described herein, the term "diagnosis" generally refers to a relative probability that a disease (e.g., an autoimmune, inflammatory autoimmune, cancer, infectious, immune, dysbiosis, etc.) is present in a subject. Similarly, the term "prognosis" generally refers to a relative probability that a certain future outcome may occur in the subject with respect to a disease state.

As described herein, the terms "biological sample" or "sample" can be used interchangeably herein and generally refer to materials obtained from or derived from a subject (e.g., a human). A biological sample can include sections of tissues such as biopsy and autopsy samples, and frozen sections taken for histological purposes. Such samples can include bodily fluids such as blood and blood fractions or products (e.g., serum, plasma, platelets, red blood cells, and the like), feces and feces fractions or products (e.g., fecal water, such as but not limited to fecal water separated from other fecal components and solids by methods such as centrifugation and filtration) sputum, tissue, cultured cells (e.g., primary cultures, explants, and transformed cells), stool, urine, synovial fluid, joint tissue, synovial tissue, synoviocytes, fibroblast-like synoviocytes, macrophage-like synoviocytes, immune cells, hematopoietic cells, fibroblasts, macrophages, dendritic cells, T-cells, etc. A sample can be obtained from a eukaryotic organism, such as a mammal such as a primate e.g., chimpanzee or human; cow; dog; cat; a rodent, e.g., guinea pig, rat, mouse; rabbit; or a bird; reptile; or fish.

As described herein, the abbreviation "sp." for species can mean at least one species (e.g., 1, 2, 3, 4, 5, or more species) of the indicated genus. The abbreviation "spp." for species can mean 2 or more species (e.g., 2, 3, 4, 5, 6, 7, 8, 9, 10 or more) of the indicated genus. Generally, a first and a second bacterium may be differentiated at various taxonomic leveles, for example, the genus level (e.g., *Akkermansia* sp.), the species level (e.g., *Akkermansia muciniphila*), the strain level (e.g., *Akkermansia muciniphila* ST7, or AM-ST7), and/or a variant (e.g., a genetic variant) level (e.g., AM-ST7_1), or by any other taxonomic method. The methods and compositions provided herein can comprise a single species within an indicated genus or indicated genera, or 2 or more (e.g., a plurality comprising more than 2) species within an indicated genus or indicated genera. Furthermore, the methods and compositions described herein can comprise one or more strains of an indicated species. A strain (e.g., a *Akkermansia muciniphila* ST7 or AM-ST7) of the present disclosure can comprise one or more genetic variants (e.g., AM-ST7_1, AM-ST7_2, and/or AM-ST7_3). Thus, the methods and compositions of the present disclosure can comprise one or more different variants of an indicated strain. Such genetic strain variants can have a high genetic similarity to each other as exemplified in FIG. 4-FIG. 6 for the variants AM-ST7_1, AM-ST7_2, and AM-ST7_3.

As described herein, the terms "bacterial composition", "bacterial population", and "bacterial consortium" can be used interchangeably herein.

As described herein, the term "derivative" in the context of chemical compounds generally refers to any chemical derivative of such compound, including any isomer, conformer, or otherwise structurally, chemically, or biologically related compounds. For example, the term "phosphatidylcholine derivative" generally refers to any phosphatidylcholine derivative, any phosphatidylcholine-like compound, any phosphatidylcholine isomer, conformer, or otherwise structurally, chemically, or biologically related compounds to the compound class of phosphatidylcholines. Moreover, the terms "phosphatidylcholine derivative" and "phosphatidylcholine-like compound" can be used interchangeably herein. In an example, a bacterial strain (e.g., a *Akkermansia muciniphila* strain) of the present disclosure can produce one or more phosphatidylcholine-like compounds. Such compounds can have a therapeutic effect, and may be used to prevent and/or treat a disease or condition in a subject.

The present disclosure provides for the identification, characterization, and use of bacterial consortia for the treatment of diseases or disorders that include but are not limited to dysbiosis, asthma, allergy, infections, and inflammatory diseases. Advances in genomics and next-generation sequencing can allow for identification and characterization of specific bacterial strains that inhabit the human gut. A presence or an absence of one or more of such bacterial strains in a subject can be associated with a disease or condition, such as a dysbiotic condition, an asthmatic condition, an allergic condition, an infection, or an inflammatory condition in a subject. The characterization and stratification of bacterial consortia comprising such bacterial strains (e.g., those listed in Table 1) may provide a platform for the identification of compositions comprising bacteria that can act synergistically to treat and/or prevent one or more of the aforementioned conditions.

Microbial Consortia

Generally, a microbial consortium of the present disclosure can comprise one or more genera, species, strains, and/or strain variants belonging to the phyla Verrucomicrobia, Firmicutes, Proteobacteria, Actinobacteria, and/or Bacteroidetes, or any combination thereof. A microbial consortium can comprise bacteria belonging to one or more of the genera *Faecalibacterium* sp., *Akkermansia* sp, *Lactobacillus* sp., or any combination thereof.

A microbial consortium can comprise less than about 20, 19, 18, 17, 16, 15, 14, 13, 12, 11, 10, 9, 8, 7, 6, 5, 4, 3, or 2 different species of bacteria. A microbial consortium can comprise less than about 20 different species of bacteria. The composition can include less than about 20 different species of bacteria. A microbial consortium can comprise less than about 15 different species of bacteria. A microbial consortium can comprise less than 15 different species of bacteria. A microbial consortium can comprise less than about 10 different species of bacteria. A microbial consortium can comprise less than 10 different species of bacteria. A microbial consortium can comprise less than about 9 different species of bacteria. A microbial consortium can comprise less than 9 different species of bacteria. A microbial consortium can comprise less than about 8 different species of bacteria. A microbial consortium can comprise less than 8 different species of bacteria. A microbial consortium can comprise less than about 7 different species of bacteria. A microbial consortium can comprise less than 7 different species of bacteria. A microbial consortium can comprise than about 6 different species of bacteria. A microbial consortium can comprise than 6 different species of bacteria. A microbial consortium can comprise less than about 5 different species of bacteria. A microbial consortium can comprise less than 5 different species of bacteria. A microbial consortium can comprise less than about 4 different species of bacteria. A microbial consortium can comprise less than 4 different species of bacteria. A microbial consortium can comprise less than about 3 different species of bacteria. A microbial consortium can comprise less than 3 different species of bacteria. A microbial consortium can comprise less than about 2 different species of bacteria. A microbial consortium can comprise less than 2 different species of bacteria.

The present disclosure provides and compositions and methods that can comprise microbial compositions comprising, consisting essentially of, or consisting of one or more (i) *Lactobacillus* strain(s), one or more (ii) *Faecalibacterium* strain(s), one or more (iii) *Akkermansia* strain(s), and/or one or more (iv) *Bifidobacterium* strain(s) for treating a disease or disorder. The compositions can comprise at least one strain of *Lactobacillus johnsonii* or *Lactobacillus crispatus*, at least one strain of *Faecalibacterium prausnitzii*, at least one strain of *Akkermansia muciniphila*, and in some cases at least one strain of *Bifidobacterium longum* or another suitable *Bifidobacterium*. *Lactobacillus johnsonii* and *Lactobacillus crispatus* is a species in the genus of *Lactobacillus* that belongs to the phylum Firmicutes. *Faecalibacterium prausnitzii* is the only known species in the *Faecalibacterium* genus, and it belongs to the phylum Firmicutes. *Akkermansia muciniphila* is a species within the genus of *Akkermansia* that belongs to the phylum Verruccomicrobia. Bifidobacteria is a genus of gram-positive bacteria that belong to the phylum Actinobacteria.

The present disclosure provides compositions and methods that can comprise microbial compositions comprising a *Lactobacillus* species that can be *Lactobacillus johnsonii* or *Lactobacillus crispatus*. The *Lactobacillus* species can be *Lactobacillus johnsonii, Lactobacillus rhamnosus, Lactobacillus zeae, Lactobacillus acidipiscis, Lactobacillus acidophilus, Lactobacillus agilis, Lactobacillus aviarius, Lactobacillus brevis, Lactobacillus coleohominis, Lactobacillus crispatus, Lactobacillus crustorum, Lactobacillus curvatus, Lactobacillus dioliovorans, Lactobacillus farraginis, Lactobacillus fermentum, Lactobacillus fuchuensis, Lactobacillus harbinensis, Lactobacillus helveticus, Lactobacillus hilgardii, Lactobacillus intestinalis, Lactobacillus jensenii, Lactobacillus kefiranofaciens, Lactobacillus kefiri, Lactobacillus lindneri, Lactobacillus mali, Lactobacillus manihotivorans, Lactobacillus mucosae, Lactobacillus oeni, Lactobacillus oligofermentans, Lactobacillus panis, Lacto-* bacillus pantheris, Lactobacillus parabrevis, Lactobacillus paracollinoides, Lactobacillus parakefiri, Lactobacillus paraplantarum, Lactobacillus pentosus, Lactobacillus pontis, Lactobacillus reuteri, Lactobacillus rossiae, Lactobacillus salivarius, Lactobacillus siliginis, Lactobacillus sucicola, Lactobacillus vaccinostercus, Lactobacillus vaginalis, Lactobacillus vini, Laclococcus garvieae, or Lactococcus lactis, or a combination thereof.

The present disclosure provides compositions and methods that can comprise microbial compositions comprising an Akkermansia species that is Akkermansia muciniphila. The Akkermansia species can be Akkermansia muciniphila or Akkermansia glycaniphila, or a combination thereof.

The present disclosure provides compositions and methods where the Bifidobacterium species can be Bifidobacterium faecale. The Bifidobacterium species can be Bifidobacterium angulatum, Bifidobacterium animalis, Bifidobacterium asteroides; Bifidobacterium bifidum; Bifidobacterium boum; Bifidobacterium breve, Bifidobacterium catenulatum, Bifidobacterium choerinum, Bifidobacterium coryneforme, Bifidobacterium cuniculi, Bifidobacterium dentium, Bifidobacterium gallicum, Bifidobacterium gallinarum, Bifidobacterium indicum, Bifidobacterium longum, Bifidobacterium longum infantis, Bifidobacterium magnum, Bifidobacterium merycicum, Bifidobacterium minimum, Bifidobacterium pseudocatenulatum, Bifidobacterium pseudolongum, Bifidobacterium psychraerophilum, Bifidobacterium pullorum, Bifidobacterium ruminantium, Bifidobacterium saeculare, Bifidobacterium scardovii, Bifidobacterium simiae, Bifidobacterium stercoris, Bifidobacterium subtile, Bifidobacterium thermacidophilum, Bifidobacterium thermophilum, or Bifidobacterium urinalis, or a combination thereof.

The present disclosure provides microbial compositions that can comprise at least one Akkermansia species. A microbial composition can comprise at least one Faecalibacterium species. A microbial composition can comprise at least one Lactobacillus species. A microbial composition can comprise at least one Akkermansia species and at least one Faecalibacterium species. A microbial composition can comprise at least one Akkermansia species and at least one Lactobacillus species (Lactobacillus sp.). A microbial composition can comprise at least one Faecalibacterium species (Faecalibacterium sp.) and at least one Lactobacillus species. The present disclosure provides microbial compositions that can comprise at least one Akkermansia species, at least one Faecalibacterium species and at least one Lactobacillus species (e.g., any of those listed below in Table 1, second to the left column).

The compositions and methods described herein can comprise one or more bacterial populations that can be described and characterized on a species level (e.g., Akkermansia muciniphila). The compositions and methods described herein can also comprise one or more bacterial populations that can be described and characterized on a strain level (e.g., Akkermansia muciniphila ST7). The compositions and methods described herein can also comprise one or more bacterial populations that can be described and characterized on a genetic variant level (e.g., Akkermansia muciniphila ST7_1), wherein the genetic variants of an indicated strain can be closely related, e.g., as those described in FIG. 4 and FIG. 5.

The present disclosure provides compositions and methods that can comprise one or more of the bacterial species and/or strains shown as isolate numbers 1-251 described in Table 1 below, or any combination of such strains (i.e., each isolate number of Table 1 corresponds to an isolated bacterial strain).

TABLE 1

Examples of Strains Used in Therapeutic Consortia

| Isolate Number | Species | Source | Isolation Media |
| --- | --- | --- | --- |
| 1 | Akkermansia muciniphila | Human - fecal | Mucin Minimal Media |
| 2 | Akkermansia muciniphila | Human - fecal | Mucin Minimal Media |
| 3 | Akkermansia muciniphila | Human - fecal | Mucin Minimal Media |
| 4 | Akkermansia muciniphila | Human - fecal | Mucin Minimal Media |
| 5 | Akkermansia muciniphila | Mus musculus - fecal | Mucin Minimal Media |
| 6 | Akkermansia muciniphila | Mus musculus - fecal | Mucin Minimal Media |
| 7 | Akkermansia muciniphila | Mus musculus - fecal | Mucin Minimal Media |
| 8 | Akkermansia muciniphila | Mus musculus - fecal | Mucin Minimal Media |
| 9 | Akkermansia muciniphila | Mus musculus - fecal | Mucin Minimal Media |
| 10 | Akkermansia muciniphila | Mus musculus - fecal | Mucin Minimal Media |
| 11 | Akkermansia muciniphila | Mus musculus - fecal | Mucin Minimal Media |
| 12 | Akkermansia muciniphila | Mus musculus - fecal | Mucin Minimal Media |
| 13 | Akkermansia muciniphila | Mus musculus - fecal | Mucin Minimal Media |
| 14 | Akkermansia muciniphila | Mus musculus - fecal | Mucin Minimal Media |
| 15 | Akkermansia muciniphila | Mus musculus - fecal | Mucin Minimal Media |
| 16 | Akkermansia muciniphila | Mus musculus - fecal | Mucin Minimal Media |
| 17 | Akkermansia muciniphila | Mus musculus - fecal | Mucin Minimal Media |
| 18 | Akkermansia muciniphila | Mus musculus - fecal | Mucin Minimal Media |
| 19 | Akkermansia muciniphila | Mus musculus - fecal | Mucin Minimal Media |
| 20 | Akkermansia muciniphila | Mus musculus - fecal | Mucin Minimal Media |
| 21 | Akkermansia muciniphila | Mus musculus - fecal | Mucin Minimal Media |
| 22 | Akkermansia muciniphila | Mus musculus - fecal | Mucin Minimal Media |
| 23 | Akkermansia muciniphila | Mus musculus - fecal | Mucin Minimal Media |
| 24 | Akkermansia muciniphila | Mus musculus - fecal | Mucin Minimal Media |
| 25 | Akkermansia muciniphila | Mus musculus - fecal | Mucin Minimal Media |
| 26 | Akkermansia muciniphila | Mus musculus - fecal | Mucin Minimal Media |
| 27 | Akkermansia muciniphila | Mus musculus - fecal | Mucin Minimal Media |
| 28 | Akkermansia muciniphila | Mus musculus - fecal | Mucin Minimal Media |
| 29 | Akkermansia muciniphila | Mus musculus - fecal | Mucin Minimal Media |
| 30 | Akkermansia muciniphila | Mus musculus - fecal | Mucin Minimal Media |
| 31 | Akkermansia muciniphila | Mus musculus - fecal | Mucin Minimal Media |
| 32 | Akkermansia muciniphila | Mus musculus - fecal | Mucin Minimal Media |

TABLE 1-continued

Examples of Strains Used in Therapeutic Consortia

| Isolate Number | Species | Source | Isolation Media |
|---|---|---|---|
| 33 | *Akkermansia muciniphila* | *Mus musculus* - fecal | Mucin Minimal Media |
| 34 | *Akkermansia muciniphila* | *Mus musculus* - fecal | Mucin Minimal Media |
| 35 | *Akkermansia muciniphila* | *Mus musculus* - fecal | Mucin Minimal Media |
| 36 | *Akkermansia muciniphila* | *Mus musculus* - fecal | Mucin Minimal Media |
| 37 | *Akkermansia muciniphila* | *Mus musculus* - fecal | Mucin Minimal Media |
| 38 | *Akkermansia muciniphila* | *Mus musculus* - fecal | Mucin Minimal Media |
| 39 | *Akkermansia muciniphila* | *Mus musculus* - fecal | Mucin Minimal Media |
| 40 | *Akkermansia muciniphila* | *Mus musculus* - fecal | Mucin Minimal Media |
| 41 | *Anaerostipes hadrus* | Human - fecal | Yeast Fatty Acid Casitone Media |
| 42 | *Anaerotignum lactatifermentans* | Human - fecal | Yeast Fatty Acid Casitone Media |
| 43 | *Bacteroides caccae* | Human - fecal | Yeast Fatty Acid Casitone Media |
| 44 | *Bacteroides caccae* | Human - fecal | Yeast Fatty Acid Casitone Media |
| 45 | *Bacteroides dorei* | Human - fecal | Yeast Fatty Acid Casitone Media |
| 46 | *Bacteroides dorei* | Human - fecal | Yeast Fatty Acid Casitone Media |
| 47 | *Bacteroides dorei* | Human - fecal | Mucin Minimal Media |
| 48 | *Bacteroides faecis* | Human - fecal | Mucin Minimal Media |
| 49 | *Bacteroides faecis* | Human - fecal | Mucin Minimal Media |
| 50 | *Bacteroides faecis* | Human - fecal | Yeast Fatty Acid Casitone Media |
| 51 | *Bacteroides faecis* | Human - fecal | Yeast Fatty Acid Casitone Media |
| 52 | *Bacteroides faecis* | Human - fecal | Yeast Fatty Acid Casitone Media |
| 53 | *Bacteroides faecis* | Human - fecal | Yeast Fatty Acid Casitone Media |
| 54 | *Bacteroides faecis* | Human - fecal | Yeast Fatty Acid Casitone Media |
| 55 | *Bacteroides faecis* | Human - fecal | Yeast Fatty Acid Casitone Media |
| 56 | *Bacteroides faecis* | Human - fecal | Yeast Fatty Acid Casitone Media |
| 57 | *Bacteroides faecis* | Human - fecal | Yeast Fatty Acid Casitone Media |
| 58 | *Bacteroides finegoldii* | Human - fecal | Yeast Fatty Acid Casitone Media |
| 59 | *Bacteroides fragilis* | Human - fecal | Yeast Fatty Acid Casitone Media |
| 60 | *Bacteroides fragilis* | Human - fecal | Yeast Fatty Acid Casitone Media |
| 61 | *Bacteroides fragilis* | Human - fecal | Yeast Fatty Acid Casitone Media |
| 62 | *Bacteroides fragilis* | Human - fecal | Yeast Fatty Acid Casitone Media |
| 63 | *Bacteroides fragilis* | Human - fecal | Yeast Fatty Acid Casitone Media |
| 64 | *Bacteroides fragilis* | Human - fecal | Yeast Fatty Acid Casitone Media |
| 65 | *Bacteroides fragilis* | Human - fecal | Yeast Fatty Acid Casitone Media |
| 66 | *Bacteroides fragilis* | Human - fecal | Mucin Minimal Media |
| 67 | *Bacteroides fragilis* | Human - fecal | Mucin Minimal Media |
| 68 | *Bacteroides fragilis* | Human - fecal | Mucin Minimal Media |
| 69 | *Bacteroides fragilis* | Human - fecal | Yeast Fatty Acid Casitone Media |
| 70 | *Bacteroides fragilis* | Human - fecal | Yeast Fatty Acid Casitone Media |
| 71 | *Bacteroides fragilis* | Human - fecal | Yeast Fatty Acid Casitone Media |
| 72 | *Bacteroides fragilis* | Human - fecal | Yeast Fatty Acid Casitone Media |
| 73 | *Bacteroides intestinalis* | Human - fecal | Yeast Fatty Acid Casitone Media |
| 74 | *Bacteroides stercoris* | Human - fecal | Yeast Fatty Acid Casitone Media |
| 75 | *Bacteroides stercoris* | Human - fecal | Yeast Fatty Acid Casitone Media |
| 76 | *Bacteroides stercoris* | Human - fecal | Yeast Fatty Acid Casitone Media |
| 77 | *Bacteroides stercoris* | Human - fecal | Yeast Fatty Acid Casitone Media |
| 78 | *Bacteroides stercoris* | Human - fecal | Yeast Fatty Acid Casitone Media |
| 79 | *Bacteroides stercoris* | Human - fecal | Yeast Fatty Acid Casitone Media |
| 80 | *Bacteroides stercoris* | Human - fecal | Yeast Fatty Acid Casitone Media |
| 81 | *Bacteroides stercoris* | Human - fecal | Yeast Fatty Acid Casitone Media |
| 82 | *Bacteroides thetaiotaomicron* | Human - fecal | Yeast Fatty Acid Casitone Media |
| 83 | *Bacteroides thetaiotaomicron* | Human - fecal | Yeast Fatty Acid Casitone Media |
| 84 | *Bacteroides thetaiotaomicron* | Human - fecal | Yeast Fatty Acid Casitone Media |
| 85 | *Bacteroides thetaiotaomicron* | Human - fecal | Yeast Fatty Acid Casitone Media |
| 86 | *Bacteroides thetaiotaomicron* | Human - fecal | Yeast Fatty Acid Casitone Media |
| 87 | *Bacteroides thetaiotaomicron* | Human - fecal | Yeast Fatty Acid Casitone Media |
| 88 | *Bacteroides thetaiotaomicron* | *Mus musculus* - fecal | Mucin Minimal Media |
| 89 | *Bacteroides thetaiotaomicron* | Human - fecal | Yeast Fatty Acid Casitone Media |
| 90 | *Bacteroides thetaiotaomicron* | Human - fecal | Mucin Minimal Media |
| 91 | *Bacteroides thetaiotaomicron* | Human - fecal | Yeast Fatty Acid Casitone Media |
| 92 | *Bacteroides uniformis* | Human - fecal | Yeast Fatty Acid Casitone Media |
| 93 | *Bacteroides uniformis* | Human - fecal | Yeast Fatty Acid Casitone Media |
| 94 | *Bacteroides uniformis* | Human - fecal | Yeast Fatty Acid Casitone Media |
| 95 | *Bacteroides vulgatus* | Human - fecal | Yeast Fatty Acid Casitone Media |
| 96 | *Bacteroides vulgatus* | Human - fecal | Yeast Fatty Acid Casitone Media |

TABLE 1-continued

Examples of Strains Used in Therapeutic Consortia

| Isolate Number | Species | Source | Isolation Media |
|---|---|---|---|
| 97 | *Bacteroides vulgatus* | Human - fecal | Yeast Fatty Acid Casitone Media |
| 98 | *Bacteroides vulgatus* | Human - fecal | Yeast Fatty Acid Casitone Media |
| 99 | *Bacteroides vulgatus* | Human - fecal | Yeast Fatty Acid Casitone Media |
| 100 | *Bacteroides vulgatus* | Human - fecal | Yeast Fatty Acid Casitone Media |
| 101 | *Bacteroides vulgatus* | Human - fecal | Yeast Fatty Acid Casitone Media |
| 102 | *Bacteroides vulgatus* | Human - fecal | Yeast Fatty Acid Casitone Media |
| 103 | *Bacteroides vulgatus* | Human - fecal | Yeast Fatty Acid Casitone Media |
| 104 | *Bacteroides vulgatus* | Human - fecal | Yeast Fatty Acid Casitone Media |
| 105 | *Bacteroides vulgatus* | Human - fecal | Yeast Fatty Acid Casitone Media |
| 106 | *Bacteroides vulgatus* | Human - fecal | Yeast Fatty Acid Casitone Media |
| 107 | *Bacteroides vulgatus* | Human - fecal | Yeast Fatty Acid Casitone Media |
| 108 | *Bacteroides vulgatus* | Human - fecal | Yeast Fatty Acid Casitone Media |
| 109 | *Bacteroides xylanisolvens* | Human - fecal | Mucin Minimal Media |
| 110 | *Bacteroides xylanisolvens* | Human - fecal | Yeast Fatty Acid Casitone Media |
| 111 | *Bifidobacterium faecale* | Human - fecal | Bifidobacterium Selective Media |
| 112 | *Bifidobacterium faecale* | Human - fecal | Bifidobacterium Selective Media |
| 113 | *Bifidobacterium longum* | Human - fecal | Bifidobacterium Selective Media |
| 114 | *Bifidobacterium stercoris* | Human - fecal | Bifidobacterium Selective Media |
| 115 | *Bifidobacterium stercoris* | Human - fecal | Bifidobacterium Selective Media |
| 116 | *Blautia faecis* | Human - fecal | Yeast Fatty Acid Casitone Media |
| 117 | *Blautia faecis* | Human - fecal | Yeast Fatty Acid Casitone Media |
| 118 | *Blautia gnavus* | Human - fecal | Yeast Fatty Acid Casitone Media |
| 119 | *Blautia luti* | Human - fecal | Yeast Fatty Acid Casitone Media |
| 120 | *Blautia obeum* | Human - fecal | Yeast Fatty Acid Casitone Media |
| 121 | *Blautia obeum* | Human - fecal | Yeast Fatty Acid Casitone Media |
| 122 | *Blautia obeum* | Human - fecal | Yeast Fatty Acid Casitone Media |
| 123 | *Blautia obeum* | Human - fecal | Yeast Fatty Acid Casitone Media |
| 124 | *Blautia obeum* | Human - fecal | Yeast Fatty Acid Casitone Media |
| 125 | *Blautia obeum* | Human - fecal | Yeast Fatty Acid Casitone Media |
| 126 | *Blautia product* | Human - fecal | Yeast Fatty Acid Casitone Media |
| 127 | *Blautia product* | Human - fecal | Yeast Fatty Acid Casitone Media |
| 128 | *Blautia product* | Human - fecal | Yeast Fatty Acid Casitone Media |
| 129 | *Blautia product* | Human - fecal | Yeast Fatty Acid Casitone Media |
| 130 | *Blautia product* | Human - fecal | Yeast Fatty Acid Casitone Media |
| 131 | *Blautia product* | Human - fecal | Yeast Fatty Acid Casitone Media |
| 132 | *Blautia product* | Human - fecal | Yeast Fatty Acid Casitone Media |
| 133 | *Blautia product* | Human - fecal | Mucin Minimal Media |
| 134 | *Blautia product* | Human - fecal | Mucin Minimal Media |
| 135 | *Blautia product* | Human - fecal | Yeast Fatty Acid Casitone Media |
| 136 | *Blautia stercoris* | Human - fecal | Yeast Fatty Acid Casitone Media |
| 137 | *Blautia stercoris* | Human - fecal | Yeast Fatty Acid Casitone Media |
| 138 | *Blautia torque* | Human - fecal | Yeast Fatty Acid Casitone Media |
| 139 | *Blautia wexlerae* | Human - fecal | Yeast Fatty Acid Casitone Media |
| 140 | *Blautia wexlerae* | Human - fecal | Yeast Fatty Acid Casitone Media |
| 141 | *Blautia wexlerae* | Human - fecal | Mucin Minimal Media |
| 142 | *Blautia wexlerae* | Human - fecal | Yeast Fatty Acid Casitone Media |
| 143 | *Blautia wexlerae* | Human - fecal | Yeast Fatty Acid Casitone Media |
| 144 | *Blautia wexlerae* | Human - fecal | Mucin Minimal Media |
| 145 | *Blautia wexlerae* | Human - fecal | Yeast Fatty Acid Casitone Media |
| 146 | *Collinsella aerofaciens* | Human - fecal | Yeast Fatty Acid Casitone Media |
| 147 | *Coprococcus comes* | Human - fecal | Yeast Fatty Acid Casitone Media |
| 148 | *Coprococcus comes* | Human - fecal | Yeast Fatty Acid Casitone Media |
| 149 | *Coprococcus comes* | Human - fecal | Yeast Fatty Acid Casitone Media |
| 150 | *Coprococcus comes* | Human - fecal | Yeast Fatty Acid Casitone Media |
| 151 | *Coprococcus comes* | Human - fecal | Yeast Fatty Acid Casitone Media |
| 152 | *Coprococcus comes* | Human - fecal | Yeast Fatty Acid Casitone Media |
| 153 | *Coprococcus comes* | Human - fecal | Yeast Fatty Acid Casitone Media |
| 154 | *Coprococcus eutactus* | Human - fecal | Yeast Fatty Acid Casitone Media |
| 155 | *Dorea formicigenerans* | Human - fecal | Yeast Fatty Acid Casitone Media |
| 156 | *Dorea formicigenerans* | Human - fecal | Yeast Fatty Acid Casitone Media |
| 157 | *Dorea formicigenerans* | Human - fecal | Yeast Fatty Acid Casitone Media |
| 158 | *Dorea longicatena* | Human - fecal | Yeast Fatty Acid Casitone Media |
| 159 | *Dorea longicatena* | Human - fecal | Yeast Fatty Acid Casitone Media |
| 160 | *Dorea longicatena* | Human - fecal | Yeast Fatty Acid Casitone Media |
| 161 | *Eisenbergiella massiliensis* | Human - fecal | Yeast Fatty Acid Casitone Media |
| 162 | *Erysipelatoclostridium ramosum* | Human - fecal | Yeast Fatty Acid Casitone Media |
| 163 | *Erysipelatoclostridium ramosum* | Human - fecal | Yeast Fatty Acid Casitone Media |
| 164 | *Erysipelatoclostridium ramosum* | Human - fecal | Yeast Fatty Acid Casitone Media |
| 165 | *Erysipelatoclostridium ramosum* | Human - fecal | Yeast Fatty Acid Casitone Media |

TABLE 1-continued

Examples of Strains Used in Therapeutic Consortia

| Isolate Number | Species | Source | Isolation Media |
|---|---|---|---|
| 166 | Erysipelatoclostridium ramosum | Human - fecal | Yeast Fatty Acid Casitone Media |
| 167 | Erysipelatoclostridium ramosum | Human - fecal | Yeast Fatty Acid Casitone Media |
| 168 | Erysipelatoclostridium ramosum | Human - fecal | Yeast Fatty Acid Casitone Media |
| 169 | Escherichia fergusonii | Human - fecal | Yeast Fatty Acid Casitone Media |
| 170 | Escherichia fergusonii | Human - fecal | Yeast Fatty Acid Casitone Media |
| 171 | Escherichia fergusonii | Human - fecal | Yeast Fatty Acid Casitone Media |
| 172 | Escherichia fergusonii | Human - fecal | Yeast Fatty Acid Casitone Media |
| 173 | Escherichia fergusonii | Human - fecal | Yeast Fatty Acid Casitone Media |
| 174 | Escherichia fergusonii | Human - fecal | Yeast Fatty Acid Casitone Media |
| 175 | Escherichia fergusonii | Human - fecal | Yeast Fatty Acid Casitone Media |
| 176 | Escherichia fergusonii | Human - fecal | Yeast Fatty Acid Casitone Media |
| 177 | Escherichia fergusonii | Human - fecal | Yeast Fatty Acid Casitone Media |
| 178 | Escherichia fergusonii | Human - fecal | Yeast Fatty Acid Casitone Media |
| 179 | Escherichia fergusonii | Human - fecal | Yeast Fatty Acid Casitone Media |
| 180 | Escherichia fergusonii | Human - fecal | Yeast Fatty Acid Casitone Media |
| 181 | Escherichia fergusonii | Human - fecal | Yeast Fatty Acid Casitone Media |
| 182 | Eubacterium hallii | Human - fecal | Yeast Fatty Acid Casitone Media |
| 183 | Eubacterium ventriosum | Human - fecal | Yeast Fatty Acid Casitone Media |
| 184 | Faecalibacterium prausnitzii | Human - fecal | Yeast Fatty Acid Casitone Media |
| 185 | Faecalibacterium prausnitzii | Human - fecal | Yeast Fatty Acid Casitone Media |
| 186 | Faecalibacterium prausnitzii | Human - fecal | Yeast Fatty Acid Casitone Media |
| 187 | Faecalibacterium prausnitzii | Human - fecal | Yeast Fatty Acid Casitone Media |
| 188 | Faecalibacterium prausnitzii | Human - fecal | Yeast Fatty Acid Casitone Media |
| 189 | Faecalibacterium prausnitzii | Human - fecal | Yeast Fatty Acid Casitone Media |
| 190 | Faecalibacterium prausnitzii | Human - fecal | Yeast Fatty Acid Casitone Media |
| 191 | Faecalibacterium prausnitzii | Human - fecal | Yeast Fatty Acid Casitone Media |
| 192 | Faecalibacterium prausnitzii | Human - fecal | Yeast Fatty Acid Casitone Media |
| 193 | Faecalibacterium prausnitzii | Human - fecal | Yeast Fatty Acid Casitone Media |
| 194 | Faecalibacterium prausnitzii | Human - fecal | Yeast Fatty Acid Casitone Media |
| 195 | Faecalibacterium prausnitzii | Human - fecal | Yeast Fatty Acid Casitone Media |
| 196 | Faecalibacterium prausnitzii | Human - fecal | Yeast Fatty Acid Casitone Media |
| 197 | Faecalibacterium prausnitzii | Human - fecal | Yeast Fatty Acid Casitone Media |
| 198 | Faecalibacterium prausnitzii | Human - fecal | Yeast Fatty Acid Casitone Media |
| 199 | Faecalibacterium prausnitzii | Human - fecal | Yeast Fatty Acid Casitone Media |
| 200 | Holdemanella biforme | Human - fecal | Yeast Fatty Acid Casitone Media |
| 201 | Holdemanella biforme | Human - fecal | Yeast Fatty Acid Casitone Media |
| 202 | Holdemanella biforme | Human - fecal | Yeast Fatty Acid Casitone Media |
| 203 | Hungatella effluvia | Human - fecal | Yeast Fatty Acid Casitone Media |
| 204 | Hungatella hathewayi | Human - fecal | Yeast Fatty Acid Casitone Media |
| 205 | Lachnoclostridium aerotolerans | Human - fecal | Yeast Fatty Acid Casitone Media |
| 206 | Lachnoclostridium aerotolerans | Human - fecal | Yeast Fatty Acid Casitone Media |
| 207 | Lachnoclostridium aldenense | Human - fecal | Yeast Fatty Acid Casitone Media |
| 208 | Lachnoclostridium asparagiforme | Human - fecal | Yeast Fatty Acid Casitone Media |
| 209 | Lachnoclostridium bolteae | Human - fecal | Yeast Fatty Acid Casitone Media |
| 210 | Lachnoclostridium lavalense | Human - fecal | Yeast Fatty Acid Casitone Media |
| 211 | Lachnoclostridium symbiosum | Human - fecal | Yeast Fatty Acid Casitone Media |
| 212 | Lachnospira pectinoschiza | Human - fecal | Yeast Fatty Acid Casitone Media |
| 213 | Lactobacillus coleohominis | Human - vaginal | de Man Rogosa Sharpe Media |
| 214 | Lactobacillus crispatus | Human - vaginal | de Man Rogosa Sharpe Media |

TABLE 1-continued

Examples of Strains Used in Therapeutic Consortia

| Isolate Number | Species | Source | Isolation Media |
|---|---|---|---|
| 215 | Lactobacillus crispatus | Human - vaginal | de Man Rogosa Sharpe Media |
| 216 | Lactobacillus crispatus | Human - vaginal | de Man Rogosa Sharpe Media |
| 217 | Lactobacillus gasseri | Mus musculus - fecal | de Man Rogosa Sharpe Media |
| 218 | Lactobacillus jensenii | Human - vaginal | de Man Rogosa Sharpe Media |
| 219 | Lactobacillus jensenii | Human - vaginal | de Man Rogosa Sharpe Media |
| 220 | Lactobacillus jensenii | Human - vaginal | de Man Rogosa Sharpe Media |
| 221 | Lactobacillus jensenii | Human - vaginal | de Man Rogosa Sharpe Media |
| 222 | Lactobacillus jensenii | Human - vaginal | de Man Rogosa Sharpe Media |
| 223 | Lactobacillus johnsonii | Mus musculus - fecal | de Man Rogosa Sharpe Media |
| 224 | Lactobacillus johnsonii | Mus musculus - fecal | de Man Rogosa Sharpe Media |
| 225 | Lactobacillus johnsonii | Mus musculus - fecal | de Man Rogosa Sharpe Media |
| 226 | Lactobacillus johnsonii | Mus musculus - fecal | de Man Rogosa Sharpe Media |
| 227 | Lactonifactor longoviformis | Human - fecal | Yeast Fatty Acid Casitone Media |
| 228 | Longibaculum muris | Human - fecal | Yeast Fatty Acid Casitone Media |
| 229 | Longibaculum muris | Human - fecal | Yeast Fatty Acid Casitone Media |
| 230 | Longibaculum muris | Human - fecal | Yeast Fatty Acid Casitone Media |
| 231 | Longibaculum muris | Human - fecal | Yeast Fatty Acid Casitone Media |
| 232 | Muribaculum intestinale | Human - fecal | Yeast Fatty Acid Casitone Media |
| 233 | Oscillibacter ruminantium | Human - fecal | Yeast Fatty Acid Casitone Media |
| 234 | Oscillibacter ruminantium | Human - fecal | Yeast Fatty Acid Casitone Media |
| 235 | Oscillibacter ruminantium | Human - fecal | Yeast Fatty Acid Casitone Media |
| 236 | Oscillibacter ruminantium | Human - fecal | Yeast Fatty Acid Casitone Media |
| 237 | Parabacteroides distasonis | Human - fecal | Yeast Fatty Acid Casitone Media |
| 238 | Parabacteroides merdae | Human - fecal | Yeast Fatty Acid Casitone Media |
| 239 | Parabacteroides merdae | Human - fecal | Yeast Fatty Acid Casitone Media |
| 240 | Parabacteroides merdae | Human - fecal | Yeast Fatty Acid Casitone Media |
| 241 | Parabacteroides merdae | Human - fecal | Yeast Fatty Acid Casitone Media |
| 242 | Parabacteroides merdae | Human - fecal | Yeast Fatty Acid Casitone Media |
| 243 | Propionibacterium acnes | Mus musculus - fecal | Mucin Minimal Media |
| 244 | Roseburia inulinivorans | Human - fecal | Yeast Fatty Acid Casitone Media |
| 245 | Roseburia inulinivorans | Human - fecal | Yeast Fatty Acid Casitone Media |
| 246 | Roseburia inulinivorans | Human - fecal | Yeast Fatty Acid Casitone Media |
| 247 | Ruminococcus bromii | Human - fecal | Yeast Fatty Acid Casitone Media |
| 248 | Shigella flexneri | Human - fecal | Yeast Fatty Acid Casitone Media |
| 249 | Staphylococcus epidermidis | Human - fecal | Yeast Fatty Acid Casitone Media |
| 250 | Staphylococcus warneri | Human - fecal | Yeast Fatty Acid Casitone Media |
| 251 | Sutterella wadsworthensis | Mus musculus - fecal | Mucin Minimal Media |

The present disclosure provides compositions and methods that can comprise at least one bacterial strain of Table 1. The present disclosure provides compositions and methods that can comprise at least two bacterial strains of Table 1. The present disclosure provides compositions and methods that can comprise at least three bacterial strains of Table 1. The present disclosure provides compositions and methods that can comprise at least about 4, 5, 6, 7, 8, 9, 10, 11, 12, 13, 14, 15, 16, 17, 18, 19, 20, 21, 22, 23, 24, 25, or least about 30 bacterial strains of Table 1.

The present disclosure provides compositions and methods that can comprise one or more of the bacterial strains 1-25 described in Table 2 below, or any combination of strains 1-25. The isolated strains of Table 2 have been numbered as strains 1-25. The isolate number of such strains corresponds to the isolate numbers shown in Table 1.

TABLE 2

Examples of Strains Used in Therapeutic Consortia

| Isolate Number | Strain Number | Bacterial Strain |
|---|---|---|
| 1 | 1 | A. muciniphila ST7 |
| 2 | 2 | A. muciniphila ST6 |
| 4 | 3 | A. muciniphila ST5 |
| 5 | 4 | A. muciniphila ST1 (Am1) |
| 11 | 5 | A. muciniphila ST15 (Am5) |
| 18 | 6 | A. muciniphila ST22 (Am6) |
| 28 | 7 | A. muciniphila ST38 (Am4) |
| 31 | 8 | A. muciniphila ST43 (Am2) |
| 33 | 9 | A. muciniphila ST46 (Am3) |
| 39 | 10 | A. muciniphila ST58 (Am7) |
| 111 | 11 | B. adolescentis ST15 (Bs10) |
| 113 | 12 | B. longum ST27 (Bl9) |
| 126 | 13 | B. producta ST4 (Bp8) |
| 147 | 14 | C. comes ST3 (Cc11) |
| 184 | 15 | F. prausnitzii ST23 (Fp13) |
| 188 | 16 | F. prausnitzii ST27 (Fp14) |
| 192 | 17 | F. prausnitzii ST38 (Fp12) |
| 195 | 18 | F. prausnitzii ST58 (Fp15) |
| 199 | 19 | F. prausnitzii ST74 (Fp16) |
| 211 | 20 | L. symbiosum ST40 (Bp7) |
| 214 | 21 | L. crispatus ST100 (Lj20) |
| 221 | 22 | L. jensenii ST10 (Lc18) |

TABLE 2-continued

Examples of Strains Used
in Therapeutic Consortia

| Isolate Number | Strain Number | Bacterial Strain |
|---|---|---|
| 223 | 23 | *L. johnsonii* ST8 (Lg19) |
| 225 | 24 | *L. johnsonii* ST74 (Lj 17) |
| 247 | 25 | *R. bromii* ST42 (Rb21) |

The present disclosure provides compositions and methods that can comprise of various microbial compositions. Such compositions can comprise any of the bacterial strains 1-25 (e.g., those listed in Table 2), or any combination of bacterial strains 1-25. Thus, a microbial composition can comprise at least one bacterial strain of Table 2. A microbial composition can comprise at least about two bacterial strains of Table 2. A microbial composition can comprise at least about three bacterial strains of Table 2. A microbial composition can comprise at least about 4, 5, 6, 7, 8, 9, 10, 11, 12, 13, 14, 15, 16, 17, 18, 19, 20, 21, 22, 23, 24, or least about 25 bacterial strains of Table 2.

A microbial composition as described herein can comprise one or more *Akkermansia muciniphila* strains, one or more *Faecalibacterium prausnitzii* strains, and/or one or more *Lactobacillus crispatus* strains. The compositions and methods described herein can comprise a microbial composition (e.g., a therapeutic microbial composition) that can comprise at least the *Akkermansia muciniphila* strain *A. muciniphila* ST7 (e.g., strain 1). The compositions and methods described herein can comprise a microbial composition (e.g., a therapeutic microbial composition) that can comprise at least the *Faecalibacterium prausnitzii* strain *F. prausnitzii* ST38 (e.g., strain 17). The compositions and methods described herein can comprise a microbial composition (e.g., a therapeutic microbial composition) that can comprise at least the *Lactobacillus crispatus* strain *L. crispatus* ST100 (e.g., strain 21).

A microbial composition of the present disclosure can comprise any one or more of the bacterial strains *A. muciniphila* ST7, *F. prausnitzii* ST38, or *L. crispatus* ST100, or any combination thereof. A microbial composition described herein can comprise at least the bacterial strains *A. muciniphila* ST7, *F. prausnitzii* ST38, and *L. crispatus* ST100.

A microbial composition as described herein can achieve certain biological effects (e.g., therapeutic effects) in a synergistic manner. A synergistic bacterial consortium can comprise any one or more of the bacterial strains *A. muciniphila* ST7, *F. prausnitzii* ST38, or *L. crispatus* ST100, or any combination thereof. Such synergistic effects of a microbial composition can include metabolic interaction between cells of different bacterial strains (e.g., cells of a first strain produce a metabolite that can be used metabolically by cells of a second strain). Such synergistic effects of a microbial composition can include therapeutic effects when administered to a subject (e.g., a rodent or a human). The metabolic activity of a bacterial composition described herein can have a synergistic therapeutic effect, such as anti-inflammatory effects, when administered to a subject in need thereof.

The microbial compositions described herein that can comprise any one or more of the bacterial strains *A. muciniphila* ST7, *F. prausnitzii* ST38, or *L. crispatus* ST100, or any combination thereof can be synergistic bacterial consortia. Synergistic effects of such a consortium can include increased therapeutic efficacy in a subject and beneficial long-term effects for said subject. A microbial composition of the present disclosure can comprise one or more bacterial species and/or strains that can produce one or more therapeutically effective compounds. Such compounds can have anti-inflammatory effects.

The production of such compounds can contribute to beneficial effects of a species or strain, or that of a microbial composition that comprises such species or strain(s). The therapeutic compositions and consortia of the present disclosure can produce various compounds and/or metabolites that can have therapeutic and/r preventative properties when administered to a subject in need thereof. Such compounds and metabolites can include fatty acids (e.g., SCFAs such as acetic acid or butyric acid), lipids, phospholipids (e.g., phosphatidylcholines and/or derivatives thereof), and/or other metabolites with beneficial (e.g., health-promoting) properties (e.g., when administered to a subject).

The compositions and methods described herein can comprise one or more bacterial cells of one or more bacterial species or strains that produce short-chain fatty acids (SCFAs). The compositions and methods described herein can comprise one or more bacterial cell of one or more bacterial species or strains that produce phospholipids and/or derivatives thereof. Such phospholipid and/or derivative thereof can be a phosphatidylcholine and/or a derivative thereof. The present disclosure provides one or more species or strains of *Akkermansia* sp. that can produce one or more phospholipids and/or derivatives thereof. The *Akkermansia* strain that produces one or more phospholipids can be *A. muciniphila* ST7. At least one of the phospholipids that can be produced by *Akkermansia* sp. (e.g., *A. muciniphila* ST7) can be a phosphatidylcholine, a phopshatidylcholine-like compound, and/or a chemical derivative thereof. Such compounds can be, or can have structural similarity to compounds 1-3 shown in FIG. 13. Such compounds can be, or can have structural similarity to any one of phosphatidylcholine-derived compounds including [3-[2-aminoethoxy(hydroxy)phosphoryl]oxy-2-hydroxypropyl] tetradecanoate, [3-[2-aminoethoxy(hydroxy)phosphoryl]oxy-2-hydroxypropyl] pentadecanoate, or [3-[2-aminoethoxy(hydroxy)phosphoryl]oxy-2-hydroxypropyl] hexadecanoate, or chemical derivatives thereof.

Therapeutic Microbial Consortia

Generally, a therapeutic microbial consortium (or population) of the present disclosure can comprise one or more genera, species, strains, and/or strain variants belonging to the phyla Verrucomicrobia, Firmicutes, Proteobacteria, Actinobacteria, and/or Bacteroidetes, or any combination thereof. A therapeutic microbial consortium can comprise bacteria belonging to one or more of the genera *Faecalibacterium* sp., *Akkermansia* sp., *Lactobacillus* sp., or any combination thereof.

A therapeutic microbial consortium can comprise less than about 20, 19, 18, 17, 16, 15, 14, 13, 12, 11, 10, 9, 8, 7, 6, 5, 4, 3, or 2 different species of bacteria. A therapeutic microbial consortium can comprise less than about 20 different species of bacteria A therapeutic microbial consortium can comprise less than 20 different species of bacteria. A therapeutic microbial consortium can comprise less than about 15 different species of bacteria. A therapeutic microbial consortium can comprise less than 15 different species of bacteria. A therapeutic microbial consortium can comprise less than about 10 different species of bacteria. A therapeutic microbial consortium can comprise less than 10 different species of bacteria. A therapeutic microbial consortium can comprise less than about 9 different species of bacteria. A therapeutic microbial consortium can comprise less than 9 different species of bacteria. A therapeutic microbial consortium can comprise less than about 8 different species of bacteria. A therapeutic microbial consortium can comprise less than 8 different species of bacteria. A therapeutic microbial consortium can comprise less than about 7 different species of bacteria. A therapeutic microbial consortium can comprise less than 7 different species of bacteria. A therapeutic microbial consortium can comprise than about 6 different species of bacteria. A therapeutic microbial consortium can comprise than 6 different species of bacteria. A therapeutic microbial consortium can comprise less than about 5 different species of bacteria. A therapeutic microbial consortium can comprise less than 5 different species of bacteria. A therapeutic microbial consortium can comprise less than about 4 different species of bacteria. A therapeutic microbial consortium can comprise less than 4 different species of bacteria. A therapeutic microbial consortium can comprise less than about 3 different species of bacteria. A therapeutic microbial consortium can comprise less than 3 different species of bacteria. A therapeutic microbial consortium can comprise less than about 2 different species of bacteria. A therapeutic microbial consortium can comprise less than 2 different species of bacteria.

A therapeutic microbial consortium (i.e., therapeutic consortium, also abbreviated herein as "TC") of the present disclosure can provide therapeutically effective amounts of said bacterial consortium to a subject in need thereof. The therapeutic consortium can comprise, consist essentially of, or consist of any of the bacterial species listed in Table 1, or any combination thereof. The present disclosure provides therapeutic microbial compositions that can comprise at least one *Akkermansia* species. A therapeutic microbial composition can comprise at least one *Faecalibacterium* species. A therapeutic microbial composition can comprise at least one *Lactobacillus* species. A therapeutic microbial composition can comprise at least one *Akkermansia* species and at least one *Faecalibacterium* species. A therapeutic microbial composition can comprise at least one *Akkermansia* species and at least one *Lactobacillus* species (*Lactobacillus* sp.). A therapeutic microbial composition can comprise at least one *Faecalibacterium* species (*Faecalibacterium* sp.) and at least one *Lactobacillus* species. The present disclosure provides therapeutic microbial compositions that can comprise at least one *Akkermansia* species, at least one *Faecalibacterium* species and at least one *Lactobacillus* species. A therapeutic microbial composition can comprise at least 1, 2, 3, 4, 5, 6, 7, 8, 9, 10, 11, 12, 13, 14, 15, 16, 17, 18, 19, 20, 21, 22, 23, 24, or least 25 bacterial species of Table 1.

Such species can be *Lactobacillus crispatus, Faecalibacterium prausnitzii, Akkermansia muciniphila,* and/or a *Bifidobacterium* species. A therapeutic microbial consortium of the present disclosure can comprise the bacterial species *Lactobacillus crispatus, Faecalibacterium prausnitzii, Akkermansia muciniphila,* and/or a *Bifidobacterium* species. Such consortia can be administered to a subject in need to treat diseases such as dysbiosis, asthma, inflammation, and/or allergy.

A therapeutic bacterial consortium of the present disclosure can comprise any one or more of the bacterial strains listed in Table 1 and/or Table 2, or any combination thereof. The present disclosure provides therapeutic microbial compositions and methods that can comprise at least one bacterial strain of Table 1. The present disclosure provides therapeutic microbial compositions and methods that can comprise at least two bacterial strains of Table 1. The present disclosure provides therapeutic microbial compositions and methods that can comprise at least three bacterial strains of Table 1. The present disclosure provides therapeutic microbial compositions and methods that can comprise at least about 4, 5, 6, 7, 8, 9, 10, 11, 12, 13, 14, 15, 16, 17, 18, 19, 20, 21, 22, 23, 24, 25, or least about 30 bacterial strain of Table 1. The present disclosure provides therapeutic microbial compositions and methods that can comprise of various microbial compositions. Such therapeutic microbial compositions can comprise any of the bacterial strains 1-25 (e.g., those listed in Table 2), or any combination of bacterial strains 1-25. Thus, a therapeutic microbial composition can comprise at least one bacterial strain of Table 2. A therapeutic microbial composition can comprise at least about two bacterial strains of Table 2. A therapeutic microbial composition can comprise at least about three bacterial strains of Table 2. A therapeutic microbial composition can comprise at least about 4, 5, 6, 7, 8, 9, 10, 11, 12, 13, 14, 15, 16, 17, 18, 19, 20, 21, 22, 23, 24, or least about 25 bacterial strains of Table 2.

A therapeutic bacterial consortium of the present disclosure can comprise at least one *A. muciniphila* strain. Such at least one strain can be *A. muciniphila* ST7. A therapeutic bacterial consortium of the present disclosure can comprise at least one *F. prausnitzii* strain. Such at least one strain can be *F. prausnitzii* ST38. A therapeutic bacterial consortium of the present disclosure can comprise at least one *L. crispatus* strain. Such strain can be *L. crispatus* ST100. A therapeutic bacterial consortium of the present disclosure can comprise at least one *A. muciniphila* strain and at least one *F. prausnitzii* strain. The at least one *A. muciniphila* strain can be *A. muciniphila* ST7, and the at least one *F. prausnitzii* strain can be *F. prausnitzii* ST38. A therapeutic bacterial consortium of the present disclosure can comprise at least one *A. muciniphila* strain and at least one *L. crispatus* strain. The at least one *A. muciniphila* strain can be *A. muciniphila* ST7, and the at least one *L. crispatus* strain can be *L. crispatus* ST100. A therapeutic bacterial consortium of the present disclosure can comprise at least one *F. prausnitzii* strain and at least one *L. crispatus* strain. The at least one *F. prausnitzii* strain can be *F. prausnitzii* ST38, and the at least one *L. crispatus* strain can be *L. crispatus* ST100. A therapeutic bacterial consortium of the present disclosure can comprise at least one *A. muciniphila* strain, at least one *F. prausnitzii* strain and at least one *L. crispatus* strain. The at least one *A. muciniphila* strain can be *A. muciniphila* ST7, the at least one *F. prausnitzii* strain can be *F. prausnitzii* ST38, and the at least one *L. crispatus* strain can be *L. crispatus* ST100. A therapeutic bacterial consortium of the present disclosure can comprise *A. muciniphila* ST7, *F. prausnitzii* ST38, or *L. crispatus* ST100. Any one of these strains, or any combination thereof, can be combined with any of the strains 1-25 of Table 1 and/or any of the strains of Table 2.

A therapeutic bacterial consortium of the present disclosure can comprise one or more variants (e.g., genetic variants) of a certain strain. For example, therapeutic consortium can comprise any one or more of the *A. muciniphila* ST7 (or AM ST7) variants AM-ST7_1, AM-ST7_2, and AM-ST7_3 (see e.g., FIG. 4-FIG. 6).

A therapeutic consortium or composition as disclosed herein can have one or more beneficial and/or therapeutic properties. Such therapeutic properties can include anti-inflammatory properties, anti-allergic, anti-infective properties, or anti-cancer properties. Such properties can include reduction of one or more pro-inflammatory markers and/or metabolites. These can include certain immunoglobulins (e.g., IgE), histamines, pro-inflammatory chemokines or cytokines (e.g., IL-4, IL-13, etc.), certain T helper cells (e.g., $T_H2$ or $T_H17$ cells), or certain immune cells such as eosinophils, neutrophils, mast cells, or basophils. The anti-inflammatory compound, marker, and/or metabolite can be a cytokine, a microbial lipid, a microbial carbohydrate, a microbial fatty acid, or a microbial amino acid. The anti-inflammatory compound can be IL-17. The pro-inflammatory compound can be a cytokine, a microbial lipid, a microbial carbohydrate, or a microbial amino acid. The pro-inflammatory compound can be IL-4, IL-10, IL-8, IL-13, TNF-a, or MUC5B, or any combination thereof. The microbial lipid can be a phospholipid. The phospholipid can be a phosphatidylcholine or a phosphatidylcholine-like compound (e.g., those listed in FIG. 13, or derivatives thereof, or those having the chemical names of any one of phosphatidylcholine-derived compounds including [3-[2-aminoethoxy(hydroxy)phosphoryl]oxy-2-hydroxypropyl] tetradecanoate, [3-[2-aminoethoxy(hydroxy)phosphoryl]oxy-2-hydroxypropyl] pentadecanoate, or [3-[2-aminoethoxy(hydroxy)phosphoryl]oxy-2-hydroxypropyl] hexadecanoate, structurally similar derivatives thereof, or those phosphatidylcholine-derived compounds that are shown in FIG. 13).

A microbial composition of the present disclosure can comprise one or more bacterial species and/or strains that can produce one or more therapeutically effective compounds. Such compounds can be small molecules (e.g., fatty acids, lipids, etc.), peptides, polypeptide, and/or nucleic acids. Such compounds can have beneficial effects in a subject (e.g., a rodent or a human) when administered to said subject (e.g., in an oral formulation). Such beneficial effects can include anti-inflammatory effects. Such anti-inflammatory effects can be systemic, i.e., anti-inflammatory effects can be elicited in various parts of the body of an organism (e.g., a mammal such as a human). The therapeutic consortia described herein can comprise one or more bacterial cells of one or more bacterial genera, species or strains that can produce small molecule metabolites with beneficial (e.g., therapeutic) properties. The beneficial small molecules can include fatty acids such as produce short-chain fatty acids (SCFAs) and/or lipids such as phospholipids. In particular, the compositions and methods described herein can comprise one or more bacterial cells of one or more bacterial genera, species or strains that produce phospholipids and/or derivatives thereof. Such phospholipid and/or derivative thereof can be a phosphatidylcholine, a phosphatidylcholine-like compound and/or a phosphatidylcholine derivative (e.g., a chemically and/or structurally similar molecule to a phosphatidylcholine). The present disclosure provides one or more species and/or strains of *Akkermansia* sp. that can produce one or more phospholipids and/or derivatives thereof. The *Akkermansia* strain that produces one or more phospholipids can be *A. muciniphila* ST7. At least one of the phospholipids that can be produced by *A. muciniphila* ST7 can be a phosphatidylcholine and/or a derivative thereof. Such compounds can have structural similarity with compounds 1-3 shown in FIG. 14. The production of one or more phosphatidylcholine(s) or derivatives thereof by *Akkermansia* sp. (e.g., *A. muciniphila* ST7) can have an anti-inflammatory effect in a subject (e.g., a human).

A therapeutic consortium of the present disclosure, once administered to a subject, can affect the metabolism of one or more compounds in the subject (e.g., a human or non-human animal). Affecting the metabolism of one or more compounds in the subject can be beneficial for said subject, e.g., in terms of having preventative and/or therapeutic properties (e.g., anti-inflammatory properties). A therapeutic consortium of the present disclosure can affect and/or alter the metabolism of fatty acids and/or lipids in a subject. A therapeutic consortium can affect and/or alter the metabolism of phospholipids and unsaturated or poly-unsaturated fatty acids. Such fatty acids can include omega-3- and/or omega-6 fatty acids. The metabolic effects that a therapeutic consortium can elicit include the metabolism of linoleic acid (e.g., alpha-linolenic acid), arachidonic acid, and other fatty acids. The metabolism of such fatty acids can be affected in a way that results in a reduction of inflammation in a subject. A therapeutic consortium can affect metabolic pathways used to metabolize certain compounds such as fatty acids, lipids, etc. Affecting such metabolic pathways can include at least a partial of full inhibition of certain metabolic pathways, such as pathways that result in the production of pro-inflammatory compounds or metabolites and/or compounds or metabolites that are associated with inflammation. A therapeutic consortium can affect and/or alter a metabolic pathway directly and/or indirectly. For example, a therapeutic consortium of the present disclosure can directly and/or indirectly increase the anti-inflammatory effects of alpha-linolenic acid by reducing the amount of alpha-linolenic acid metabolite(s) that may mediate inflammation and thus counteract the anti-inflammatory effects of that lipid. Thus, a therapeutic consortium can beneficially affect and/or alter a metabolism in a subject. This can result in reducing the incidence of inflammation (e.g., chronic and/or allergic inflammation), a metabolic disease or disorder, an allergy, a dysbiosis, a cancer, or any combination thereof.

A therapeutic consortium of the present disclosure can produce beneficial fatty acids, SCFAs, lipids, and/or phospholipids (e.g., phosphatidylcholine or a derivative thereof). The amount of any of such compounds produced by a therapeutic consortium can be at least about 1.1, 1.2, 1.3., 1.4, 1.5., 1.6, 1.7, 1.8., 1.9., 2, 2.2, 2.5, 2.8, 3, 3.5, 4, 5, 6, 7, 8, 9, 10, 20, 50, or 100 times the amount produced by a consortium that does not contain all the bacterial genera, species, and/or strains of the therapeutic consortium.

A therapeutic consortium of the present disclosure can comprise *A. muciniphila* sp. Such a therapeutic consortium can produce one or more phosphatidylcholine(s) and/or derivatives thereof. The consortium comprising *A. muciniphila* sp. can produce at least about 1.1, 1.2, 1.3., 1.4, 1.5., 1.6, 1.7, 1.8., 1.9., 2, 2.2, 2.5, 2.8, 3, 3.5, 4, 5, 6, 7, 8, 9, 10, 20, 50, or 100 times the amount of a phosphatidylcholine or a derivative thereof than a consortium that does not contain *A. muciniphila* sp.

A therapeutically effective microbial consortium as provided herein can refer to a therapeutically effective composition including a bacterial population that comprises, consists essentially of, or consists of any 1, 2, 3, 4, 5, 6, 7, or 8 of *Lactobacillus* species and/or strains, *Faecalibacterium* species and/or strains, and/or *Akkermansia* species and/or strains, or any combination thereof. A microbial composition as described herein can comprise one or more *Bifidobacterium* species and/o strains. The composition can include less than about 20, 19, 18, 17, 16, 15, 14, 13, 12, 11, 10, 9, 8, 7, 6, 5, 4, 3, or 2 different species of bacteria.

A composition provided herein can be administered orally and can include live microorganisms at a concentration of at least about $10^3$, $10^4$, $10^5$, $10^6$, $10^7$, $10^8$, $10^9$, $10^{10}$, $10^{11}$ or greater units per gram (cfu/g). The composition provided herein can be administered orally and includes live microorganisms from about $10^7$ to about $10^{11}$ cfu/g. The composition can include from about $10^4$ to about $10^{15}$ cfu/g of a bacterial species or strain. The composition can include from about $10^5$ to about $10^{15}$ cfu/g of a bacterial species or strain.

The composition can include from about $10^6$ to about $10^{15}$ cfu/g of a bacterial species or strain. The composition can include from about $10^7$ to about $10^{15}$ cfu/g of a bacterial species or strain. The composition can include from about $10^8$ to about $10^{15}$ cfu/g of a bacterial species or strain. The composition can include from about $10^9$ to about $10^{15}$ cfu/g. The composition can include from about $10^{10}$ to about $10^{15}$ cfu/g of a bacterial species or strain. The composition can include from about $10^{11}$ to about $10^{15}$ cfu/g of a bacterial species or strain. The composition can include from about $10^{12}$ to about $10^{15}$ cfu/g of a bacterial species or strain. The composition can include from about $10^{13}$ to about $10^{15}$ cfu/g of a bacterial species or strain. The composition can include from about $10^{14}$ to about $10^{15}$ cfu/g of a bacterial species or strain. The composition can include from about $10^3$ to about $10^{15}$ cfu/g of a bacterial species or strain.

A bacterial composition as provided herein can be administered orally (e.g., as a solid dosage from or as a liquid such as a solution or suspension) and can include at least about $10^7$ to about $10^{11}$ cfu per bacterial species or strain. A composition provided herein can be administered orally and can include at least about $10^7$ to about $10^{13}$ cfu per bacterial specie or strain. A composition provided herein can be administered orally and can include at least about $10^5$ to about $10^{10}$ cfu per bacterial species or strain. A composition provided herein can be administered orally and can include at least about $10^4$ to about $10^9$ cfu per bacterial species or strain. A composition provided herein can be administered orally and can include at least about $10^5$ to about $10^8$ cfu per bacterial species or strain.

Pharmaceutical Compositions

A microbial composition (e.g., a therapeutic bacterial consortium) of the present disclosure can be used and/or administered as a pharmaceutical composition. Such a pharmaceutical composition can comprise one or more pharmaceutically acceptable excipients and/or carriers.

"Pharmaceutically acceptable excipient" and "pharmaceutically acceptable carrier" can refer to a substance that aids the administration of an active agent (e.g., a microbial composition) to and absorption by a subject and can be included in the compositions of the present disclosure without causing a significant adverse toxicological effect on a subject (e.g., a rodent or a human). Non-limiting examples of pharmaceutically acceptable excipients can include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethycellulose, polyvinyl pyrrolidine, and colors, and the like. Such preparations can be sterilized and/or mixed with auxiliary agents such as lubricants, preservatives, stabilizers, wetting agents, emulsifiers, salts for influencing osmotic pressure, buffers, coloring, and/or aromatic substances and the like that do not deleteriously react with the compounds of the present disclosure. An excipient can consume oxygen, e.g., reducing the oxygen content of or within a composition or pharmaceutical composition. Reducing the oxygen content may increase the viability of the bacterial cells in that composition, in cases where e.g., the bacteria are anaerobic bacteria.

The microbial compositions provided herein can be administered orally, gastrointestinally, or rectally. Administration can be in the form of a single bolus dose, or may be, for example, by a continuous perfusion pump. The microbial consortium provided herein can be combined with one or more excipients, for example, a disintegrant, a filler, a glidant, or a preservative. The microbial consortium provided herein can form part of a capsule. Suitable capsules include both hard shell capsules or soft-shelled capsules. Any lipid-based or polymer-based colloid can be used to form the capsule. Exemplary polymers useful for colloid preparations include gelatin, plant polysaccharides or their derivatives such as carrageenans and modified forms of starch and cellulose, e.g., hypromellose. Optionally, other ingredients can be added to the gelling agent solution, for example plasticizers such as glycerin and/or sorbitol to decrease the capsule's hardness, coloring agents, preservatives, disintegrants, lubricants and surface treatment.

The microbial compositions of the present disclosure can be formulated in a unit dosage form, each dosage containing, for example, from about 0.005 mg to about 2000 mg of a defined microbial consortium having minimal urease activity per dose. The term "unit dosage forms" can refer to physically discrete units suitable as unitary dosages for human subjects and other mammals, each unit containing a predetermined quantity of active material calculated to produce the desired therapeutic effect, in association with a suitable pharmaceutical excipient. For preparing solid compositions such as tablets, the principal active ingredient can be mixed with a pharmaceutical excipient to form a solid preformulation composition containing a homogeneous mixture of a compound of the present disclosure. When referring to these preformulation compositions as homogeneous, the active ingredient is typically dispersed evenly throughout the composition so that the composition can be readily subdivided into equally effective unit dosage forms such as tablets, pills and capsules. This solid preformulation can then be subdivided into unit dosage forms of the type described above containing from, for example, 0.005 mg to about 1000 mg of the microbial composition provided herein.

The microbial compositions of the present disclosure can be formulated in a unit dosage form, each dosage containing from about 0.1 mg to about 50 mg, from about 0.1 mg to about 40 mg, from about 0.1 mg to about 20 mg from about 0.1 mg to about 10 mg, from about 0.2 mg to about 20 mg, from about 0.3 mg to about 15 mg, from about 0.4 mg to about 10 mg, from about 0.5 mg to about 1 mg; from about 0.5 mg to about 100 mg, from about 0.5 mg to about 50 mg, from about 0.5 mg to about 30 mg, from about 0.5 mg to about 20 mg, from about 0.5 mg to about 10 mg, from about 0.5 mg to about 5 mg; from about 1 mg from to about 50 mg, from about 1 mg to about 30 mg, from about 1 mg to about 20 mg, from about 1 mg to about 10 mg, from about 1 mg to about 5 mg; from about 5 mg to about 50 mg, from about 5 mg to about 20 mg, from about 5 mg to about 10 mg; from about 10 mg to about 100 mg, from about 20 mg to about 200 mg, from about 30 mg to about 150 mg, from about 40 mg to about 100 mg, from about 50 mg to about 100 mg of a *Lactobacillus* sp. (e.g., *L. crispatus* ST100), *Faecalibacterium* sp. (e.g., *F. prausnitzii* ST38), and/or an *Akkermansia* sp. (e.g., *A. muciniphila* ST7), either individually or combined.

Tablets or pills that can be used in combination with the microbial compositions of the present disclosure can be coated or otherwise compounded to provide a dosage form affording the advantage of prolonged action. A tablet or pill can comprise an inner dosage and an outer dosage component, the latter being in the form of an envelope over the former. The two components can be separated by an enteric layer which serves to resist disintegration in the stomach and permit the inner component to pass intact into the duodenum or to be delayed in release. A variety of materials can be used for such enteric layers or coatings, such materials including a number of polymeric acids and mixtures of polymeric acids with such materials as shellac, cetyl alcohol, and cellulose acetate. The liquid forms in which the compositions of the present disclosure can be incorporated for administration orally or by injection include aqueous solutions, suitably flavored syrups, aqueous or oil suspensions, and flavored emulsions with edible oils such as cottonseed oil, sesame oil, coconut oil, or peanut oil, as well as elixirs and similar pharmaceutical vehicles.

Methods of Treatment

The therapeutic microbial compositions and methods described herein can be used for the prevention and/or treatment of a disease or condition in a subject (e.g., a rodent or a human).

Therapeutic treatment using the herein described microbial compositions (e.g., those comprising one or more of A. muciniphila ST7, F. prausnitzii ST38, or L. crispatus ST100, or a combination thereof) can include administering to a subject a therapeutically effective amount of said microbial composition (e.g., as a pharmaceutical composition) before and/or after diagnosis or development of a disease, condition, or disorder. Thus, a method of treating a disease (e.g., an inflammatory disease, an infection, and/or a dysbiosis) in a subject in need thereof can be provided by utilizing the herein described compositions and methods.

The one or more bacteria of a therapeutic composition of the present disclosure can be delivered in a lyophilized form or a suspended (e.g., liquid) from. The dosage that may be administered to a subject in need thereof can depend on the route of administration, the nature of the formulation, the nature of the subject's condition, e.g., immaturity of the immune system or a gastrointestinal disorder, the subject's size, weight, surface area, age, and sex, and/or other drugs being administered, and the judgment of the attending clinicians. Suitable dosages can be in the range of 0.01-1,000 mg/kg. Some typical dose ranges can be from about 1 µg/kg to about 1 g/kg of body weight per day. The dose range can be from about 0.01 mg/kg to about 100 mg/kg of body weight per day. The dose can be, for example, 1 mg/kg, 2 mg/kg, 5 mg kg, 10 mg/kg, 20 mg/kg, 50 mg/kg or 100 mg/kg. Alternatively or in addition, the dosage can be expressed as cfu or as cfu/g of dry weight. Thus, the dosage may vary, but can range from the equivalent of about $10^2$ to about $10^{12}$ cfu/g, e.g., $1\times10^2$ cfu/g, $5\times10^2$ cfu/g, $1\times10^3$ cfu/g, $5\times10^3$ cfu/g, $1\times10^4$ cfu/g, $5\times10^4$ cfu/g, $1\times10^5$ cfu/g, $5\times10^5$ cfu/g, $1\times10^6$ cfu/g, $5\times10^6$ cfu/g, $1\times10^7$ cfu/g, $5\times10^7$ cfu/g, $1\times10^8$ cfu/g, $5\times10^8$ cfu/g, $1\times10^9$ cfu/g, $5\times10^9$ cfu/g, $1\times10^{10}$ cfu/g $5\times10^{10}$ cfu/g, $1\times10^{11}$ cfu/g, $5\times10^{11}$ cfu/g, or $1\times10^{12}$ cfu/g, or more of dry weight of any one of the administered bacteria (individually) or of the total population of bacteria. The dosage can range from about $10^2$ to about $10^{12}$ cfu, e.g., $1\times10^2$ cfu, $5\times10^2$ cfu, $1\times10^3$ cfu, $5\times10^3$ cfu, $1\times10^4$ cfu, $5\times10^4$ cfu, $1\times10^5$ cfu, $5\times10^5$ cfu, $1\times10^6$ cfu, $5\times10^6$ cfu, $1\times10^7$ cfu, $5\times10^7$ cfu, $1\times10^8$ cfu, $5\times10^8$ cfu, $1\times10^9$ cfu, $5\times10^9$ cfu, $1\times10^{10}$ cfu, $5\times10^{10}$ cfu, $1\times10^{11}$ cfu, $5\times10^{11}$ cfu, or $1\times10^{12}$ cfu of any one of the administered bacteria (individually) or of the total population of bacteria (e.g., A. muciniphila ST7, F. prausnitzii ST38, or L. crispatus ST100, or any combination thereof).

The methods and compositions of the present disclosure can be administered to a subject in need thereof. The subject may suffer from a disease or conditions. The subject can be a neonate, an infant, a toddler, a child, a teenager, an adult, or a subject of any age. The neonate can be less than about 3 days old. The neonate can be less than about 1 week old. The neonate can be less than about 2 weeks old. The neonate can be less than about 3 weeks old. The neonate can be less than about 4 weeks old. The infant can be less than about 8 weeks old. The infant can be at least about 2 months old. The infant can be at least 6 about months old. The infant can be at least about 12 about months old.

The methods and compositions of the present disclosure can be administered to a subject of varying ages and maturity. The microbial compositions can be used to treat a subject that can be between about 2 and about 18 years old, or can be at least about 18 years old. The subject can be between 2 and 18 years old, or is at least 18 years old. The subject can be between about 2 and about 18 years old, or is at least about 18 (e.g., 19, 20, 25, 30, 40, 50, 60, 70, 80, 90) years old. The subject can be between about 2 and about 18 years old, or is about 19 years old. The subject can be between about 2 and about 18 years old, or is 19 years old. The subject can be between about 2 and about 18 years old, or is about 20 years old. The subject can be between about 2 and about 18 years old, or can be 20 years old. The subject can be between about 2 and about 18 years old, or can be about 25 years old. The subject can be between about 2 and about 18 years old, or can be 25 years old. The subject can be between about 2 and about 18 years old, or can be about 30 years old, or older. The subject can be between about 2 and about 18 years old, or can be 30 years old. The subject can be between about 2 and about 18 years old, or can be about 40 years old. The subject can be between about 2 and about 18 years old, or can be 40 years old. The subject can be less than about 50 years old. The subject can be less than about 60 years old. The subject can be at least about 60 years old. The subject can be at least about 80 years old.

The compositions and methods described herein can be used to prevent and/or treat various disorders, conditions, or disease, and can be administered for various periods of time. A treatment period may vary between subjects and individuals and can depend on various factors as described herein, e.g., disease state, age, etc. A subject can be treated for at least about one day to at least about one week. The subject can be treated for at least about a week to at least about one month. The subject can be treated for at least about one month to at least about one year. The subject can be treated for at least about two months. The subject can be treated for at least about six months. The subject can be treated for at least twelve months. The subject can be treated for at least two years. The subject can be treated on consecutive days, consecutive weeks, and/or consecutive months.

The methods and compositions of the present disclosure can be used to prevent and/or treat various disorders, conditions, or diseases. Such disorders, conditions, or diseases can be caused by dysbiosis. The dysbiosis can be dysbiosis of a gut microbial composition. Dysbiosis can be described as a microbial imbalance within the human gut. Microbial imbalance can include the overgrowth of potentially pathogenic bacteria leading to changes in functional and metabolic compositions of the gut flora.

The disease to be prevented and/or treated can be an inflammatory disease. The inflammatory disease can be an allergy, atopy, asthma, an autoimmune disease, an autoinflammatory disease, a hypersensitivity, pediatric allergic asthma, allergic asthma, inflammatory bowel disease, Celiac disease, Crohn's disease, colitis, ulcerative colitis, collagenous colitis, lymphocytic colitis, diverticulitis, irritable bowel syndrome, short bowel syndrome, stagnant loop syndrome, chronic persistent diarrhea, intractable diarrhea of infancy, Traveler's diarrhea, immunoproliferative small intestinal disease, chronic prostatitis, postenteritis syndrome, tropical sprue, Whipple's disease, Wolman disease, arthritis, rheumatoid arthritis, Behcet's disease, uveitis, pyoderma gangrenosum, erythema nodosum, traumatic brain injury, psoriatic arthritis, juvenile idiopathic arthritis, multiple sclerosis, systemic lupus erythematosus (SLE), myasthenia gravis, juvenile onset diabetes, diabetes mellitus type 1, Guillain-Barre syndrome, Hashimoto's encephalitis, Hashimoto's thyroiditis, ankylosing spondylitis, psoriasis, Sjogren's syndrome, vasculitis, glomerulonephritis, autoimmune thyroiditis, bullous pemphigoid, sarcoidosis, ichthyosis, Graves ophthalmopathy, Addison's disease, Vitiligo, acne vulgaris, pelvic inflammatory disease, reperfusion injury, sarcoidosis, transplant rejection, interstitial cystitis, atherosclerosis, or atopic dermatitis.

The inflammatory disease to be treated and/or prevented using the herein described microbial consortia can be a pediatric condition such as pediatric allergic asthma or inflammatory bowel disease. The pediatric subject may suffer from constipation, diarrhea, bloating, urgency, and/or abdominal pain.

Therapeutically effective bacterial consortia as described herein can comprise, consist essentially of, or consist of the bacterial species *Lactobacillus johnsonii* or *Lactobacillus crispatus, Faecalibacterium prausnitzii, Akkermansia muciniphila*, or a *Bifidobacterium* species, strains thereof, and/or any combination thereof. Such microbial compositions can be used to treat pediatric indications, including pediatric dysbiosis and pediatric inflammatory diseases. Such a bacterial consortium can comprise any one or more of the bacterial strains *A. muciniphila* ST7, *F. prausnitzii* ST38, or *L. crispatus* ST100, or any combination thereof. A microbial composition described herein can comprise at least the bacterial strains *A. muciniphila* ST7, *F. prausnitzii* ST38, and *L. crispatus* ST100.

Containers, Kits, and Instructions

The present disclosure provides containers and kits that can be used in combination with the herein described microbial (e.g., bacterial) compositions (e.g., therapeutic microbial compositions). The present disclosure further provides instructions that can direct a user (e.g., a human user) to use the microbial compositions as well as the containers and kits that comprise such microbial compositions.

Containers of the present disclosure can be used to grow, store, transport, aliquot, and/or administer therapeutic microbial compositions. Containers can be used to administer a therapeutic microbial composition to a subject (e.g., a human subject). Such containers can, for example, provide conditions suitable for growth, transport, and/or storage (e.g., cooled or frozen storage) of microbial populations, e.g., those populations that comprise one or more anaerobic bacterial cells. In such cases, a container may be used to provide a certain oxygen content or concentration during growth, transport, and/or storage of a therapeutic microbial composition in order to preserve the viability of the bacteria. Containers can further be used to provide suitable volumes, amounts, and schedules for administration a microbial composition to a subject (e.g., self-administration).

Kits of the present disclosure provide various components for using the microbial compositions described herein. Such components can include containers, test samples, equipment for analyzing the composition, e.g., its viability, pH of the storage medium, etc. Generally, kits allow for user-friendly, accurate and reliable use of the therapeutic compositions described herein, including, but not limited to dosing, administration, storage, transport, etc.

The present disclosure provides instructions for using kits and/or containers in combination with the therapeutic compositions described herein. Such instructions can be written instructions or oral instructions, or a combination thereof. Such instructions can direct a user to use the therapeutic microbial compositions as well as the containers and kits that comprise such microbial compositions.

Procedures and Methods

General Sample Preparation. Samples such as biological samples comprising one or more bacterial species can be collected and prepared using various methodologies. The sample may be a fecal sample obtained from a subject, such as a rodent or a human.

Fecal samples can be collected from subjects. Subsequent to delivery, these samples can be divided into aliquots (e.g., 0.5 g aliquots). One tube from each sample can be frozen immediately at −80° C. One tube of each sample can be stored at +4° C. for several hours (e.g., one for about 6 h and the other for about 24 h). Two additional tubes can be incubated at room temperature and collected at the same time points (e.g., 6 and 24 h). At the end point, samples can be rapidly frozen at −80° C. for subsequent fecal DNA extraction as described below.

Aliquots of (e.g., 0.5 g) of feces can be resuspended in 10 mL of SM buffer and homogenized by vigorous vortexing for at least 5 min. Tubes can then be cooled on ice for 5 min prior to centrifugation at 5000 rpm for 10 min at +4° C. Supernatants can be transferred to new tubes, and the centrifugation step can be repeated one or more times. Supernatants can be subsequently filtered twice through a 0.45-millipore PES syringe-mounted membrane filters. NaCl and PEG-8000 powders can then be added to filtrates to give a final concentration of 0.5 M and 10% (weight), respectively. Once the samples have been dissolved they can be incubated overnight at +4° C. The samples can be subsequently centrifuged at 5000 rpm for 20 min at +4° C. to collect precipitate. Pellets can be resuspended in 400 μl of SM buffer and extracted by gentle shaking with equal volume of chloroform. Emulsions can then be centrifuged at 2500 rpm for 5 min using a desktop centrifuge. The aqueous phase (~360 μl) can be aspirated into clean Eppendorf tubes and mixed with 40 μl of a solution of 10 mM $CaCl_2$ and 50 mM $MgCl_2$. After addition of 8 U of TURBO DNase (Ambion/ThermoFisher Scientific) and 20 U of RNase I (ThermoFisher Scientific) free DNA/RNA digestion can be carried out at 37° C. for 1 h before inactivating enzymes at 70° C. for 10 min. Proteinase K (40 μg) and 20 μl of 10% SDS can then be added to the tubes, and incubation was continued for 20 min at 56° C. Finally, viral particles can be lysed by addition of 100 μl of Phage Lysis Buffer (e.g., 4.5 M guanidinium isothiocyanate, 44 mM sodium citrate pH 7.0, 0.88% sarkosyl, 0.72% 2-mercaptoethanol) and incubation at 65° C. for 10 min. Ly-sates can then be extracted twice by gentle vortexing with equal volume of Phenol/Chloroform/Isoamyl Alcohol 25:24:1 (Fisher Scientific) followed by centrifugation at 8000 rpm for 5 min at room temperature. The resulting aqueous phase can be subjected to a final round of purification using DNeasy Blood & Tissue Kit (Qiagen), e.g., according to manufacturer's instruction with a final elution volume of 50 μl.

Sequencing. The microbial compositions of the present disclosure can be analyzed and characterized using a variety of techniques. For example, iTag amplicon sequencing can be a barcoded 16S rRNA gene amplicon sequencing methodology that can be utilized to determine the relative abundance of each taxon in a community, and/or to compare the taxonomic profile between subject groups of interest. Amplicon sequencing analysis can provide information on the overall microbial profile and its changes over time, both within and between treatment groups. The microbial compositions of the present disclosure can also be characterized using Shotgun metagenomic sequencing, an effective environmental sequencing approach that provides information about biodiversity and function of a microbial community. The microbial compositions of the present disclosure may be analyzed and characterized using short-chain fatty acid (SCFA) analysis. Since SCFAs can be the main fermentation products of gut microbiota and provide important insights into the relationship between the gut microbiota and the host's physiology, their analysis offers information about status, composition, and activity of the gut microbial composition. The health and disease status of a host as well as the compositions and activities of the hosts' microbiome can be analyzed and characterized using calprotectin analysis. Fecal sample analysis of calprotectin can provide information on inflammation in the gut. Moreover, fecal sample analysis of calprotectin can provide information on the composition of the microbial consortium of the subject. Amplicon sequencing analysis can be performed for the taxonomic profiling of prokaryotic communities (16S V4 region), eukaryotic communities (18S), fungal communities (ITS2), and archaeal communities (16S V4-V5 region), or any combination thereof.

The identification of isolate samples (e.g., strains) can be performed by PCR amplification of the full-length 16S rRNA gene. Such a method can use one or more forward primer and/or one or more reverse primer followed by capillary sequencing. Full-length 16S rRNA gene sequence reads can be aligned in the Ribosomal Database Project (RDP), manually curated using nucleic acid analysis and sequencing programs (e.g., ARB, mother, etc.) to classify reads to operational taxonomic units (OTUs). The full-length 16S rRNA gene sequence of each species-level OTU can then be compared to the RDP reference database to assign taxonomic designations to the genus and/or strain level followed by a BLASTn search to either a characterized or candidate novel species.

Sequencing results can be compared with databases, e.g., those of the Human Microbiome Project (HMP), and can be carried out using 97% sequence similarity of the 16S rRNA gene sequence from the cultured bacteria to define a species when only partial 16S rRNA gene sequences may be available. Genomic DNA can be extracted from at least one representative of each unique OTU using, for example, a phenol-chloroform-based DNA isolation procedure. DNA can then be sequenced on an Illumina HiSeq platform generating read lengths of 100 bp which can be assembled and annotated for further analysis. DNA can be extracted directly from each sample (e.g., a fecal sample) for whole-community metagenomic and 16S rRNA gene amplicon sequencing using the MP Biomedical FastDNA SPIN Kit for soil. For comparisons with the complete community samples, non-confluent cultures can be scraped from agar plates 72 h after inoculation with the initial fecal sample and DNA is extracted from this community using the same or similar DNA isolation process. 16S rRNA gene amplicon libraries are produced by PCR amplification of variable regions 1 and 2 of the 16S rRNA gene using the Q5 High-Fidelity Polymerase Kit supplied by New England Biolabs.

Shotgun Sequencing. Several microliters (e.g., 5-20 μL) of fecal nucleic acid sample regardless of concentration can be taken into reverse transcription reaction using Super-Script IV Reverse Transcriptase (RT) kit (Invitrogen/ThermoFisher Scientific), or similar equipment, according to the manufacturer's random hexamer primer protocol. One microliter of reverse-transcribed nucleic acids is then amplified using MDA technology with Illustra GenomiPhi V2 kit (GE Healthcare), and repeated for each sample. Products from all three MDA reactions, together with the remainder of RT products, can be pooled together and subjected to additional round of purification using DNeasy Blood & Tissue Kit. Amplified DNA can be quantified using Qubit dsDNA HS Assay Kit (Invitrogen/ThermoFisher Scientific) and may be subjected to random shotgun library preparation using Nextera XT DNA Library Preparation Kit (Illumina) and bead-based normalization following the standard manufacturer's protocol. Ready-to-load libraries can be sequenced using a proprietary modified protocol using e.g., 2×300 bp paired-end chemistry on an Illumina MiSeq platform (Illumina, San Diego, Calif.).

DNA Extraction and Library Preparation for Microbiota Profiling using 16S rRNA Amplicon Sequencing. The QIAamp Fast DNA Stool Mini Kit (Qiagen, Hilden, Germany) can be used according to manufacturer's guidelines to extract total fecal DNA from 200 mg aliquots of feces, but may be modified to include a bead-beating step. The samples can be placed in 2 mL screw-cap tubes containing 1 mL of InhibitEX Buffer and a mixture of inert beads (ThistleScientific) of various diameters (one 3.5 mm glass bead, 200.tl of 1 mm zirconium beads, 200.tl of 0.1 mm zirconium beads). Following 2×30 s beating in FastPrep-24 instrument (MP Biomedicals) with an intermittent step of cooling on ice for 30 s, the samples can be lysed by heating for 5 min at 95° C. Subsequently, the samples are processed according to the standard Qiagen protocol.

Hypervariable regions V3 and V4 of bacterial 16S ribosomal RNA genes can be amplified from 15 ng of total DNA template via PCR using Phusion High-Fidelity PCR Master Mix (ThermoFisher Scientific), appropriate primers and overhang adapter sequences (sequence portions complementary to bacterial 16S rRNA genes are underlined). The following PCR program can be used: 98° C. 30 s, 25 cycles of 98° C. 10 s, 55° C. 15 s, 72° C. 20 s, final extension 72° C. 5 min. Following purification using Agencourt AMPure XP magnetic beads (Beckman-Coulter), the amplicon libraries can undergo a second PCR reaction to attach dual Illumina Nextera indices using the Nextera XT index kit v2 (Illumina). Following purification (as described above), the dsDNA libraries can then be quantified using a Qubit dsDNA HS Assay Kit and pooled in equimolar concentrations. Ready-to-load libraries can be sequenced using a proprietary modified protocol using 2×300 bp paired-end chemistry on an Illumina MiSeq platform (Illumina, San Diego, Calif.).

Analysis of 16S rRNA amplicon sequencing data. The quality of the raw reads can be visualized using FastQC (e.g., version v0.11.3). The reads are then imported into R (e.g., version v3.3.0) for data analysis with the DADA2 package (e.g., version v1.03). Errors introduced during the sequencing process can be corrected to generate ribosomal sequence variants (RSVs). These can be exported and further chimera filtered using both the de novo and reference-based chimera filtering implemented in USEARCH v8.1.1861 with the ChimeraSlayer gold database v20110519. The remaining RSVs are classified with mothur v1.38 against the RDP database version 11.4, as well as classified with SPINGO to species level. Only RSVs with a domain classification of bacteria or archaea are kept for further analysis. A phylogenetic tree of the RSV sequences rooted on the midpoint is generated with FastTree.

Culturing of Microbial Strains and Species. The bacterial strains of the present disclosure may be obtained from a variety of sources. The bacterial strains can be obtained from live sources or may be purchased from commercially available providers, or a combination thereof. The microorganisms that the microbial consortia of the present disclosure can be comprised of may be obtained from fecal samples (e.g., from an animal such as a rodent or a human). The microorganisms (e.g., bacteria) that the microbial consortia of the present disclosure can be comprised of may be obtained from human fecal samples.

Fecal samples are generally stored and handled under anaerobic conditions (see e.g., EXAMPLE 1 and EXAMPLE 2). Fresh fecal samples can be stored and handled under anaerobic conditions within 1 h of passing to preserve the viability of anaerobic bacteria. All sample processing and culturing steps can be performed under anaerobic conditions. Culture media, PBS and all other materials that can be used for culturing can be generally placed in the anaerobic cabinet at least 24 h before use to reduce to anaerobic conditions. Anaerobic culture methods can include the use of Hungate culture tubes, sealed with butyl rubber septa (Bellco Glass), for example.

Homogenization of fecal samples can be performed using reduced PBS (e.g., using 0.1 g sample per ml PBS) and can be serially diluted and plated directly onto YCFA agar supplemented with approximately 0.002 g/ml each of glucose, maltose and cellobiose in large (13.5 cm diameter) Petri dishes. In some instances, YCFA medium is used as growth medium for bacteria. The YCFA medium may generally contain (per 100 ml) Casitone (1.0 g), yeast extract (0.25 g), $NaHCO_3$ (0.4 g), cysteine (0.1 g), $K_2HPO_4$ (0.045 g), $KH_2PO_4$ (0.045 g), NaCl (0.09 g), $(NH_4)_2SO_4$ (0.09 g), $MgSO_4.7H_2O$ (0.009 g), $CaCl_2$ (0.009 g), resazurin (0.1 mg), hemin (1 mg), biotin (1 μg), cobalamin (1 μg), p-aminobenzoic acid (3 μg), folic acid (5 μg), and pyridoxamine (15 μg). In addition, certain short-chain fatty acids (SCFA) are present including (final concentrations) acetate (33 mM); propionate (9 mM); isobutyrate, isovalerate, and valerate (1 mM each). Cysteine can be added to the medium following boiling and dispensed into Hungate tubes while the tubes are flushed with $CO_2$. After autoclaving, filter-sterilized solutions of thiamine and riboflavin are added to give final concentrations of 0.05 μg/ml of each. For some experiments, the Casitone content can be decreased to 0.2%. Carbohydrate or other energy sources can be added as needed, and the final pH of the medium is generally adjusted to 6.8±0.1.

Bacterial strains can be isolated from samples by plating a specific volume (e.g., about 1 μl) of the fecal material with directly on YCFAG medium. After a specific incubation time (e.g., 12 h to 16 h) at 37° C. in an anaerobic tent (approximately 80% $N_2$, 12% $CO_2$, and 8% $H_2$), 500 translucent colonies per sample are selected and subcultured on fresh plates (50 per plate in a grid-like fashion). After continued growth, bacterial colonies can presumptively be identified based on morphology. The majority of colonies (e.g., 95%) are disregarded, with the remaining colonies being submitted for purification and further analysis including Gram staining. Colonies of the isolated strains (i.e., isolate samples) can be routinely maintained by growing colonies for 16 to 18 h at 37° C. in 7.5-ml aliquots of M2GSC medium and maintained anaerobically using $O_2$-free $CO_2$. Isolate samples obtained and isolated from fecal matter can also be subjected to metagenomic sequencing in order to profile the entire bacterial community present.

Isolated strains disclosed herein have been deposited in the DSM Leibniz Institute DSMZ—German Collection of Microorganisms and Cell Cultures, Inhoffenstr. 7B, D-38124 Braunschweig, Germany in accordance with and under the provisions of the Budapest Treaty for the Deposit of Microorganisms, i.e., they will be stored with all the care necessary to keep them viable and uncontaminated for a period of at least five years after the most recent request for the furnishing of a sample of the deposits, and in any case, for a period of at least 30 (thirty) years after the date of deposit or for the enforceable life of any patent which may issue disclosing the cultures plus five years after the last request for a sample from the deposit. The strains were tested by the DSMZ and determined to be viable. The DSMZ has assigned the following deposit accession numbers to the strains: *Coprococcus comes* ST3 (DSM 33176), *Bacteroides faecis* (DSM 33177), *Bacteroides thetaiotaomicron* (DSM 33178), *Bifidobacterium Longum* ST27 (DSM 33179), *Blautia producta* ST4 (DSM 33180), *Faecalibacterium prausnitzii* ST38 (DSM 33185), *Faecalibacterium prausnitzii* ST23 (DSM 33186), *Lactobacillus crispatus* ST100 (DSM 33187), *Dorea longicatena* (DSM 33188), *Faecalibacterium prausnitzii* ST27 (DSM 33190), *Faecalibacterium prausnitzii* ST58 (DSM 33191), *Akkermansia muciniphila* ST7 (DSM 33213), all of which were deposited on Jun. 27, 2019. The depositor acknowledges the duty to replace the deposits should the depository be unable to furnish a sample when requested, due to the condition of the deposits. All restrictions on the availability to the public of the subject culture deposits will be irrevocably removed upon the granting of a patent disclosing them. The deposits are available as required by foreign patent laws in countries wherein counterparts of the subject application, or its progeny, are filed. However, it should be understood that the availability of a deposit does not constitute a license to practice the subject matter disclosed herein in derogation of patent rights granted by governmental action.

EXAMPLES

These examples are provided for illustrative purposes only and not to limit the scope of the claims provided herein.

Example 1

Preparation of the Anaerobic Chamber for Isolation of Anaerobic Bacterial Colonies This example describes illustrative steps conducted in preparation to handling and isolating anaerobic bacterial strains within an anaerobic chamber.

All sterile and pre-reduced consumable plastics and culture media were placed into the anaerobic chamber at least one day prior to utilization to allow for full oxygen reduction. Further, all tubes, vials, and flasks were left in the anaerobic chamber with open lids in order to allow for gas exchange and reduction over night.

The following consumables were placed into the anaerobic chamber at least one day prior to use: >100 mL PBS+0.5 mg/mL cysteine (PBS+Cys); 1 mL filter tips, 1.5 mL tubes, 2 mL screw cap cryovials containing 0.75 mL of 50% glycerol in PBS.

Agar and broth culture media are prepared and transferred to the anaerobic chamber at least one day prior to use. The anaerobic media contained either 1 mM $Na_2S.9H_2O$ or 0.5 mg/mL cysteine as reducing agents to promote growth of strict anaerobes. Agar plates were poured inside the anaerobic chamber to prevent the oxidation of media components after autoclaving.

Example 2

Growth, Isolation, and Selection of Liquid Culture Colonies

This example describes the culture of obligatory and facultative anaerobic bacterial strains that were derived from human sample on selective media. Upon subculturing, the colonies were transferred to a liquid medium and subsequently prepared for PCR and sequencing. Colonies were also preserved as glycerol stocks.

Human samples were collected in anaerobic transport media (Anaerobic Systems As-915) or in fecal collection vials sealed within a plastic bag containing an anaerobic atmosphere generating system (e.g. AnaeroPouch Thermo Fisher R686001). All samples were immediately transferred into an anaerobic chamber to minimize transit time and potential oxygen exposure to ensure viability of the anaerobic strains.

Serial dilution tubes were prepared by aliquoting 0.9 mL of PBS+Cys into 13 tubes (with a volume of 1.5 mL). Using a disposable spatula or loop, 20-30 mg of sample is transferred into a first 1.5 mL tube containing 0.9 mL of PBS+Cys. The resulting mixture was vortexed for approximately 30 seconds and 0.1 mL of the resulting, homogenous solution is transferred into the second 1.5 mL tube containing 0.9 mL of PBS+Cys. This step was then repeated until all 13 tubes contain serial dilutions ($10^0$-$10^{-12}$ dilutions in vials 1-13) of the sample.

Using a disposable hockey stick spreader, ~0.1 mL from the sample tubes containing the dilutions $10^{-5}$ to $10^{-12}$ (vials 6-13) were added to separate agar plates containing the selective agar growth media. The agar plates were then sealed with parafilm to prevent evaporation and placed into an incubator for 72 hours at 37° C. Colonies that fit a target's colony morphology were identified, and placed on a new, pre-reduced agar plate for isolation. The agar plates were sealed with parafilm and placed into an incubator for another 72 hours at 37° C.

For instance, the target morphology of *Lactobacillus johnsonii* colonies was circular white colonies with an entire margin and convex elevation, and with a diameter of 2-3 mm. The target morphology of *Faecalibacterium prausnitzii* colonies appeared as circular shaped and with a tan color, with an entire margin and flat to umbonate elevation, and with a diameter of 2-3 mm. The target morphology of *Akkermansia muciniphila* colonies appeared as circular shaped and opaque, with an entire margin and convex elevation, and with a diameter of 1-2 mm.

The isolated colonies were transferred into liquid media by picking target isolated colonies from culture plates and resuspending the colonies in 1 mL of pre-reduced liquid broth. Positive and negative controls of target organisms are inoculated in parallel to compare for growth and monitor for contamination, respectively. All liquid colony samples are then incubated for 72 hours at 37° C.

Using the positive and negative controls, positive match broth cultures were identified. Glycerol stocks of positive match broth cultures were prepared by transferring 0.75 mL of the broth culture solution into a 2 mL cryotube containing 0.75 mL of 50% glycerol in PBS. Sealed cryotube samples were then removed from the anaerobic chamber and stored at −80° C. The remaining broth culture samples were used for isolate identification using 16S-based PCR as described in the example below (EXAMPLE 3).

Example 3

16S-Based PCR for Isolate Identification

This example describes a method for conducting 16S-based PCR for isolate identification.

Broth culture samples were centrifuged to form cell pellets and the resulting supernatant is carefully removed to leave the formed cell pellet intact. The cell pellet is then resuspended in 0.5-1 mL ultrapure water.

The PCR Mastermix for a final reaction volume of 50 µL was prepared using the following PCR components (NEB E5000S) and volumes: 10× Buffer (5 µL), 10 mM dNTPs (1 µL), 10 µM 27F Forward Primer (1 µL), 10 µM 1492R Reverse Primer (1 µL), Taq Polymerase (0.25 µL), and sterile water (40.25 µL). The PCR Mastermix (48.5 µL) and 1.5 µL of resuspended bacterial cells are placed into a 0.2 mL PCR strip tube and vortexed before the PCR reaction samples are exposed to the following thermocycler protocol:

| Step | Temp | Time |
| --- | --- | --- |
| 1 | 95° C. | 2 min |
| 2 | 95° C. | 30 sec |
| 3 | 50° C. | 30 sec |
| 4 | 68° C. | 1 min 30 sec |
|  |  | (30 repeats of steps 2-4) |
| 5 | 72° C. | 5 min |
| 6 | 4° C. | HOLD |

Upon completion of the PCR reactions, samples can be submitted for Sanger sequencing using GENEWIZ or a comparable vendor.

Example 4

Listing and Identification of Refined and Isolated Bacterial Strains

This example shows all isolates (isolate numbers 1-251) that were produced using the isolation protocol as described above (EXAMPLE 2). All isolates were further identified in terms of their taxonomy using the above described protocol for 16S-based PCR (EXAMPLE 3).

Overall, 251 isolated bacterial strains (e.g., isolates) were identified and characterized. Fecal samples were obtained from healthy female children (human), healthy male and female adults (human), and from female C57/blk6 mice (*Mus musculus*).

Table 3 below shows the isolate numbers, species, sample sources, and isolation media for all isolated strains 1-251.

Table 4 below shows the 16S-based PCR results for all isolates, including quality score and identity.

Table 5 below shows the taxonomic identification of all bacterial isolates 1-251, including phylum, class, family, genus, and species.

TABLE 3

Species, Source, and Isolation Media Information for Isolate Samples (Strains) 1-251

| Isolate Number | Species | Source | Source ID | Isolation Media |
|---|---|---|---|---|
| 1 | *Akkermansia muciniphila* | Human - fecal | healthy child ♀ | Mucin Minimal Media |
| 2 | *Akkermansia muciniphila* | Human - fecal | healthy child ♀ | Mucin Minimal Media |
| 3 | *Akkermansia muciniphila* | Human - fecal | healthy child ♀ | Mucin Minimal Media |
| 4 | *Akkermansia muciniphila* | Human - fecal | healthy adult ♀ | Mucin Minimal Media |
| 5 | *Akkermansia muciniphila* | *Mus musculus* - fecal | C57/blk6 ♀ | Mucin Minimal Media |
| 6 | *Akkermansia muciniphila* | *Mus musculus* - fecal | C57/blk6 ♀ | Mucin Minimal Media |
| 7 | *Akkermansia muciniphila* | *Mus musculus* - fecal | C57/blk6 ♀ | Mucin Minimal Media |
| 8 | *Akkermansia muciniphila* | *Mus musculus* - fecal | C57/blk6 ♀ | Mucin Minimal Media |
| 9 | *Akkermansia muciniphila* | *Mus musculus* - fecal | C57/blk6 ♀ | Mucin Minimal Media |
| 10 | *Akkermansia muciniphila* | *Mus musculus* - fecal | C57/blk6 ♀ | Mucin Minimal Media |
| 11 | *Akkermansia muciniphila* | *Mus musculus* - fecal | C57/blk6 ♀ | Mucin Minimal Media |
| 12 | *Akkermansia muciniphila* | *Mus musculus* - fecal | C57/blk6 ♀ | Mucin Minimal Media |
| 13 | *Akkermansia muciniphila* | *Mus musculus* - fecal | C57/blk6 ♀ | Mucin Minimal Media |
| 14 | *Akkermansia muciniphila* | *Mus musculus* - fecal | C57/blk6 ♀ | Mucin Minimal Media |
| 15 | *Akkermansia muciniphila* | *Mus musculus* - fecal | C57/blk6 ♀ | Mucin Minimal Media |
| 16 | *Akkermansia muciniphila* | *Mus musculus* - fecal | C57/blk6 ♀ | Mucin Minimal Media |
| 17 | *Akkermansia muciniphila* | *Mus musculus* - fecal | C57/blk6 ♀ | Mucin Minimal Media |
| 18 | *Akkermansia muciniphila* | *Mus musculus* - fecal | C57/blk6 ♀ | Mucin Minimal Media |
| 19 | *Akkermansia muciniphila* | *Mus musculus* - fecal | C57/blk6 ♀ | Mucin Minimal Media |
| 20 | *Akkermansia muciniphila* | *Mus musculus* - fecal | C57/blk6 ♀ | Mucin Minimal Media |
| 21 | *Akkermansia muciniphila* | *Mus musculus* - fecal | C57/blk6 ♀ | Mucin Minimal Media |
| 22 | *Akkermansia muciniphila* | *Mus musculus* - fecal | C57/blk6 ♀ | Mucin Minimal Media |
| 23 | *Akkermansia muciniphila* | *Mus musculus* - fecal | C57/blk6 ♀ | Mucin Minimal Media |
| 24 | *Akkermansia muciniphila* | *Mus musculus* - fecal | C57/blk6 ♀ | Mucin Minimal Media |
| 25 | *Akkermansia muciniphila* | *Mus musculus* - fecal | C57/blk6 ♀ | Mucin Minimal Media |
| 26 | *Akkermansia muciniphila* | *Mus musculus* - fecal | C57/blk6 ♀ | Mucin Minimal Media |
| 27 | *Akkermansia muciniphila* | *Mus musculus* - fecal | C57/blk6 ♀ | Mucin Minimal Media |
| 28 | *Akkermansia muciniphila* | *Mus musculus* - fecal | C57/blk6 ♀ | Mucin Minimal Media |
| 29 | *Akkermansia muciniphila* | *Mus musculus* - fecal | C57/blk6 ♀ | Mucin Minimal Media |
| 30 | *Akkermansia muciniphila* | *Mus musculus* - fecal | C57/blk6 ♀ | Mucin Minimal Media |
| 31 | *Akkermansia muciniphila* | *Mus musculus* - fecal | C57/blk6 ♀ | Mucin Minimal Media |
| 32 | *Akkermansia muciniphila* | *Mus musculus* - fecal | C57/blk6 ♀ | Mucin Minimal Media |
| 33 | *Akkermansia muciniphila* | *Mus musculus* - fecal | C57/blk6 ♀ | Mucin Minimal Media |
| 34 | *Akkermansia muciniphila* | *Mus musculus* - fecal | C57/blk6 ♀ | Mucin Minimal Media |
| 35 | *Akkermansia muciniphila* | *Mus musculus* - fecal | C57/blk6 ♀ | Mucin Minimal Media |
| 36 | *Akkermansia muciniphila* | *Mus musculus* - fecal | C57/blk6 ♀ | Mucin Minimal Media |
| 37 | *Akkermansia muciniphila* | *Mus musculus* - fecal | C57/blk6 ♀ | Mucin Minimal Media |
| 38 | *Akkermansia muciniphila* | *Mus musculus* - fecal | C57/blk6 ♀ | Mucin Minimal Media |
| 39 | *Akkermansia muciniphila* | *Mus musculus* - fecal | C57/blk6 ♀ | Mucin Minimal Media |
| 40 | *Akkermansia muciniphila* | *Mus musculus* - fecal | C57/blk6 ♀ | Mucin Minimal Media |
| 41 | Anaerostipes hadrus | Human - fecal | healthy adult ♀ | Yeast Fatty Acid Casitone Media |
| 42 | Anaerotignum lactatifermentans | Human - fecal | healthy adult ♂ | Yeast Fatty Acid Casitone Media |
| 43 | Bacteroides caccae | Human - fecal | healthy child ♀ | Yeast Fatty Acid Casitone Media |
| 44 | Bacteroides caccae | Human - fecal | healthy child ♀ | Yeast Fatty Acid Casitone Media |
| 45 | Bacteroides dorei | Human - fecal | healthy child ♀ | Yeast Fatty Acid Casitone Media |
| 46 | Bacteroides dorei | Human - fecal | healthy child ♀ | Yeast Fatty Acid Casitone Media |
| 47 | Bacteroides dorei | Human - fecal | healthy child ♀ | Mucin Minimal Media |
| 48 | Bacteroides faecis | Human - fecal | healthy adult ♀ | Mucin Minimal Media |
| 49 | Bacteroides faecis | Human - fecal | healthy adult ♀ | Mucin Minimal Media |
| 50 | Bacteroides faecis | Human - fecal | healthy adult ♀ | Yeast Fatty Acid Casitone Media |
| 51 | Bacteroides faecis | Human - fecal | healthy adult ♀ | Yeast Fatty Acid Casitone Media |
| 52 | Bacteroides faecis | Human - fecal | healthy adult ♀ | Yeast Fatty Acid Casitone Media |
| 53 | Bacteroides faecis | Human - fecal | healthy adult ♀ | Yeast Fatty Acid Casitone Media |
| 54 | Bacteroides faecis | Human - fecal | healthy adult ♀ | Yeast Fatty Acid Casitone Media |
| 55 | Bacteroides faecis | Human - fecal | healthy child ♀ | Yeast Fatty Acid Casitone Media |
| 56 | Bacteroides faecis | Human - fecal | healthy child ♀ | Yeast Fatty Acid Casitone Media |
| 57 | Bacteroides faecis | Human - fecal | healthy child ♀ | Yeast Fatty Acid Casitone Media |
| 58 | Bacteroides finegoldii | Human - fecal | healthy adult ♀ | Yeast Fatty Acid Casitone Media |
| 59 | Bacteroides fragilis | Human - fecal | healthy adult ♂ | Yeast Fatty Acid Casitone Media |

TABLE 3-continued

Species, Source, and Isolation Media Information for Isolate Samples (Strains) 1-251

| Isolate Number | Species | Source | Source ID | Isolation Media |
|---|---|---|---|---|
| 60 | Bacteroides fragilis | Human - fecal | healthy adult ♂ | Yeast Fatty Acid Casitone Media |
| 61 | Bacteroides fragilis | Human - fecal | healthy adult ♂ | Yeast Fatty Acid Casitone Media |
| 62 | Bacteroides fragilis | Human - fecal | healthy adult ♂ | Yeast Fatty Acid Casitone Media |
| 63 | Bacteroides fragilis | Human - fecal | healthy adult ♂ | Yeast Fatty Acid Casitone Media |
| 64 | Bacteroides fragilis | Human - fecal | healthy adult ♂ | Yeast Fatty Acid Casitone Media |
| 65 | Bacteroides fragilis | Human - fecal | healthy adult ♂ | Yeast Fatty Acid Casitone Media |
| 66 | Bacteroides fragilis | Human - fecal | healthy adult ♂ | Mucin Minimal Media |
| 67 | Bacteroides fragilis | Human - fecal | healthy adult ♂ | Mucin Minimal Media |
| 68 | Bacteroides fragilis | Human - fecal | healthy child ♀ | Mucin Minimal Media |
| 69 | Bacteroides fragilis | Human - fecal | healthy child ♀ | Yeast Fatty Acid Casitone Media |
| 70 | Bacteroides fragilis | Human - fecal | healthy child ♀ | Yeast Fatty Acid Casitone Media |
| 71 | Bacteroides fragilis | Human - fecal | healthy adult ♀ | Yeast Fatty Acid Casitone Media |
| 72 | Bacteroides fragilis | Human - fecal | healthy adult ♀ | Yeast Fatty Acid Casitone Media |
| 73 | Bacteroides intestinalis | Human - fecal | healthy child ♀ | Yeast Fatty Acid Casitone Media |
| 74 | Bacteroides stercoris | Human - fecal | healthy child ♀ | Yeast Fatty Acid Casitone Media |
| 75 | Bacteroides stercoris | Human - fecal | healthy child ♀ | Yeast Fatty Acid Casitone Media |
| 76 | Bacteroides stercoris | Human - fecal | healthy adult ♂ | Yeast Fatty Acid Casitone Media |
| 77 | Bacteroides stercoris | Human - fecal | healthy adult ♂ | Yeast Fatty Acid Casitone Media |
| 78 | Bacteroides stercoris | Human - fecal | healthy adult ♂ | Yeast Fatty Acid Casitone Media |
| 79 | Bacteroides stercoris | Human - fecal | healthy adult ♂ | Yeast Fatty Acid Casitone Media |
| 80 | Bacteroides stercoris | Human - fecal | healthy adult ♂ | Yeast Fatty Acid Casitone Media |
| 81 | Bacteroides stercoris | Human - fecal | healthy adult ♀ | Yeast Fatty Acid Casitone Media |
| 82 | Bacteroides thetaiotaomicron | Human - fecal | healthy adult ♂ | Yeast Fatty Acid Casitone Media |
| 83 | Bacteroides thetaiotaomicron | Human - fecal | healthy adult ♂ | Yeast Fatty Acid Casitone Media |
| 84 | Bacteroides thetaiotaomicron | Human - fecal | healthy child ♀ | Yeast Fatty Acid Casitone Media |
| 85 | Bacteroides thetaiotaomicron | Human - fecal | healthy child ♀ | Yeast Fatty Acid Casitone Media |
| 86 | Bacteroides thetaiotaomicron | Human - fecal | healthy child ♀ | Yeast Fatty Acid Casitone Media |
| 87 | Bacteroides thetaiotaomicron | Human - fecal | healthy child ♀ | Yeast Fatty Acid Casitone Media |
| 88 | Bacteroides thetaiotaomicron | Mus musculus - fecal | C57/blk6 ♀ | Mucin Minimal Media |
| 89 | Bacteroides thetaiotaomicron | Human - fecal | healthy adult ♀ | Yeast Fatty Acid Casitone Media |
| 90 | Bacteroides thetaiotaomicron | Human - fecal | healthy adult ♀ | Mucin Minimal Media |
| 91 | Bacteroides thetaiotaomicron | Human - fecal | healthy adult ♀ | Yeast Fatty Acid Casitone Media |
| 92 | Bacteroides uniformis | Human - fecal | healthy adult ♂ | Yeast Fatty Acid Casitone Media |
| 93 | Bacteroides uniformis | Human - fecal | healthy adult ♂ | Yeast Fatty Acid Casitone Media |
| 94 | Bacteroides uniformis | Human - fecal | healthy child ♀ | Yeast Fatty Acid Casitone Media |
| 95 | Bacteroides vulgatus | Human - fecal | healthy adult ♀ | Yeast Fatty Acid Casitone Media |
| 96 | Bacteroides vulgatus | Human - fecal | healthy child ♀ | Yeast Fatty Acid Casitone Media |
| 97 | Bacteroides vulgatus | Human - fecal | healthy child ♀ | Yeast Fatty Acid Casitone Media |
| 98 | Bacteroides vulgatus | Human - fecal | healthy adult ♂ | Yeast Fatty Acid Casitone Media |
| 99 | Bacteroides vulgatus | Human - fecal | healthy adult ♂ | Yeast Fatty Acid Casitone Media |

TABLE 3-continued

Species, Source, and Isolation Media Information for Isolate Samples (Strains) 1-251

| Isolate Number | Species | Source | Source ID | Isolation Media |
|---|---|---|---|---|
| 100 | Bacteroides vulgatus | Human - fecal | healthy adult ♂ | Yeast Fatty Acid Casitone Media |
| 101 | Bacteroides vulgatus | Human - fecal | healthy adult ♂ | Yeast Fatty Acid Casitone Media |
| 102 | Bacteroides vulgatus | Human - fecal | healthy adult ♂ | Yeast Fatty Acid Casitone Media |
| 103 | Bacteroides vulgatus | Human - fecal | healthy child ♀ | Yeast Fatty Acid Casitone Media |
| 104 | Bacteroides vulgatus | Human - fecal | healthy child ♀ | Yeast Fatty Acid Casitone Media |
| 105 | Bacteroides vulgatus | Human - fecal | healthy child ♀ | Yeast Fatty Acid Casitone Media |
| 106 | Bacteroides vulgatus | Human - fecal | healthy child ♀ | Yeast Fatty Acid Casitone Media |
| 107 | Bacteroides vulgatus | Human - fecal | healthy adult ♀ | Yeast Fatty Acid Casitone Media |
| 108 | Bacteroides vulgatus | Human - fecal | healthy child ♀ | Yeast Fatty Acid Casitone Media |
| 109 | Bacteroides xylanisolvens | Human - fecal | healthy adult ♂ | Mucin Minimal Media |
| 110 | Bacteroides xylanisolvens | Human - fecal | healthy child ♀ | Yeast Fatty Acid Casitone Media |
| 111 | Bifidobacterium faecale | Human - fecal | healthy child ♀ | Bifidobacterium Selective Media |
| 112 | Bifidobacterium faecale | Human - fecal | healthy child ♀ | Bifidobacterium Selective Media |
| 113 | Bifidobacterium longum | Human - fecal | healthy adult ♀ | Bifidobacterium Selective Media |
| 114 | Bifidobacterium stercoris | Human - fecal | healthy adult ♂ | Bifidobacterium Selective Media |
| 115 | Bifidobacterium stercoris | Human - fecal | healthy adult ♂ | Bifidobacterium Selective Media |
| 116 | Blautia faecis | Human - fecal | healthy adult ♀ | Yeast Fatty Acid Casitone Media |
| 117 | Blautia faecis | Human - fecal | healthy adult ♀ | Yeast Fatty Acid Casitone Media |
| 118 | Blautia gnavus | Human - fecal | healthy adult ♂ | Yeast Fatty Acid Casitone Media |
| 119 | Blautia luti | Human - fecal | healthy child ♀ | Yeast Fatty Acid Casitone Media |
| 120 | Blautia obeum | Human - fecal | healthy adult ♀ | Yeast Fatty Acid Casitone Media |
| 121 | Blautia obeum | Human - fecal | healthy child ♀ | Yeast Fatty Acid Casitone Media |
| 122 | Blautia obeum | Human - fecal | healthy child ♀ | Yeast Fatty Acid Casitone Media |
| 123 | Blautia obeum | Human - fecal | healthy adult ♂ | Yeast Fatty Acid Casitone Media |
| 124 | Blautia obeum | Human - fecal | healthy child ♀ | Yeast Fatty Acid Casitone Media |
| 125 | Blautia obeum | Human - fecal | healthy child ♀ | Yeast Fatty Acid Casitone Media |
| 126 | Blautia product | Human - fecal | healthy adult ♀ | Yeast Fatty Acid Casitone Media |
| 127 | Blautia product | Human - fecal | healthy adult ♀ | Yeast Fatty Acid Casitone Media |
| 128 | Blautia product | Human - fecal | healthy adult ♀ | Yeast Fatty Acid Casitone Media |
| 129 | Blautia product | Human - fecal | healthy adult ♀ | Yeast Fatty Acid Casitone Media |
| 130 | Blautia product | Human - fecal | healthy adult ♀ | Yeast Fatty Acid Casitone Media |
| 131 | Blautia product | Human - fecal | healthy adult ♀ | Yeast Fatty Acid Casitone Media |
| 132 | Blautia product | Human - fecal | healthy adult ♀ | Yeast Fatty Acid Casitone Media |
| 133 | Blautia product | Human - fecal | healthy child ♀ | Mucin Minimal Media |
| 134 | Blautia product | Human - fecal | healthy adult ♀ | Mucin Minimal Media |
| 135 | Blautia product | Human - fecal | healthy adult ♂ | Yeast Fatty Acid Casitone Media |
| 136 | Blautia stercoris | Human - fecal | healthy adult ♂ | Yeast Fatty Acid Casitone Media |
| 137 | Blautia stercoris | Human - fecal | healthy adult ♂ | Yeast Fatty Acid Casitone Media |
| 138 | Blautia torque | Human - fecal | healthy adult ♀ | Yeast Fatty Acid Casitone Media |

TABLE 3-continued

Species, Source, and Isolation Media Information for Isolate Samples (Strains) 1-251

| Isolate Number | Species | Source | Source ID | Isolation Media |
|---|---|---|---|---|
| 139 | Blautia wexlerae | Human - fecal | healthy child ♀ | Yeast Fatty Acid Casitone Media |
| 140 | Blautia wexlerae | Human - fecal | healthy adult ♂ | Yeast Fatty Acid Casitone Media |
| 141 | Blautia wexlerae | Human - fecal | healthy adult ♂ | Mucin Minimal Media |
| 142 | Blautia wexlerae | Human - fecal | healthy adult ♂ | Yeast Fatty Acid Casitone Media |
| 143 | Blautia wexlerae | Human - fecal | healthy child ♀ | Yeast Fatty Acid Casitone Media |
| 144 | Blautia wexlerae | Human - fecal | healthy child ♀ | Mucin Minimal Media |
| 145 | Blautia wexlerae | Human - fecal | healthy child ♀ | Yeast Fatty Acid Casitone Media |
| 146 | Collinsella aerofaciens | Human - fecal | healthy child ♀ | Yeast Fatty Acid Casitone Media |
| 147 | Coprococcus comes | Human - fecal | healthy adult ♀ | Yeast Fatty Acid Casitone Media |
| 148 | Coprococcus comes | Human - fecal | healthy child ♀ | Yeast Fatty Acid Casitone Media |
| 149 | Coprococcus comes | Human - fecal | healthy child ♀ | Yeast Fatty Acid Casitone Media |
| 150 | Coprococcus comes | Human - fecal | healthy child ♀ | Yeast Fatty Acid Casitone Media |
| 151 | Coprococcus comes | Human - fecal | healthy adult ♂ | Yeast Fatty Acid Casitone Media |
| 152 | Coprococcus comes | Human - fecal | healthy child ♀ | Yeast Fatty Acid Casitone Media |
| 153 | Coprococcus comes | Human - fecal | healthy child ♀ | Yeast Fatty Acid Casitone Media |
| 154 | Coprococcus eutactus | Human - fecal | healthy adult ♂ | Yeast Fatty Acid Casitone Media |
| 155 | Dorea formicigenerans | Human - fecal | healthy child ♀ | Yeast Fatty Acid Casitone Media |
| 156 | Dorea formicigenerans | Human - fecal | healthy child ♀ | Yeast Fatty Acid Casitone Media |
| 157 | Dorea formicigenerans | Human - fecal | healthy child ♀ | Yeast Fatty Acid Casitone Media |
| 158 | Dorea longicatena | Human - fecal | healthy adult ♂ | Yeast Fatty Acid Casitone Media |
| 159 | Dorea longicatena | Human - fecal | healthy adult ♂ | Yeast Fatty Acid Casitone Media |
| 160 | Dorea longicatena | Human - fecal | healthy adult ♂ | Yeast Fatty Acid Casitone Media |
| 161 | Eisenbergiella massiliensis | Human - fecal | healthy child ♀ | Yeast Fatty Acid Casitone Media |
| 162 | Erysipelatoclostridium ramosum | Human - fecal | healthy child ♀ | Yeast Fatty Acid Casitone Media |
| 163 | Erysipelatoclostridium ramosum | Human - fecal | healthy child ♀ | Yeast Fatty Acid Casitone Media |
| 164 | Erysipelatoclostridium ramosum | Human - fecal | healthy child ♀ | Yeast Fatty Acid Casitone Media |
| 165 | Erysipelatoclostridium ramosum | Human - fecal | healthy adult ♀ | Yeast Fatty Acid Casitone Media |
| 166 | Erysipelatoclostridium ramosum | Human - fecal | healthy adult ♀ | Yeast Fatty Acid Casitone Media |
| 167 | Erysipelatoclostridium ramosum | Human - fecal | healthy adult ♀ | Yeast Fatty Acid Casitone Media |
| 168 | Erysipelatoclostridium ramosum | Human - fecal | healthy adult ♀ | Yeast Fatty Acid Casitone Media |
| 169 | Escherichia fergusonii | Human - fecal | healthy adult ♀ | Yeast Fatty Acid Casitone Media |
| 170 | Escherichia fergusonii | Human - fecal | healthy adult ♀ | Yeast Fatty Acid Casitone Media |
| 171 | Escherichia fergusonii | Human - fecal | healthy adult ♀ | Yeast Fatty Acid Casitone Media |
| 172 | Escherichia fergusonii | Human - fecal | healthy adult ♂ | Yeast Fatty Acid Casitone Media |
| 173 | Escherichia fergusonii | Human - fecal | healthy child ♀ | Yeast Fatty Acid Casitone Media |
| 174 | Escherichia fergusonii | Human - fecal | healthy child ♀ | Yeast Fatty Acid Casitone Media |
| 175 | Escherichia fergusonii | Human - fecal | healthy child ♀ | Yeast Fatty Acid Casitone Media |

TABLE 3-continued

Species, Source, and Isolation Media Information for Isolate Samples (Strains) 1-251

| Isolate Number | Species | Source | Source ID | Isolation Media |
|---|---|---|---|---|
| 176 | Escherichia fergusonii | Human - fecal | healthy child ♀ | Yeast Fatty Acid Casitone Media |
| 177 | Escherichia fergusonii | Human - fecal | healthy child ♀ | Yeast Fatty Acid Casitone Media |
| 178 | Escherichia fergusonii | Human - fecal | healthy child ♀ | Yeast Fatty Acid Casitone Media |
| 179 | Escherichia fergusonii | Human - fecal | healthy child ♀ | Yeast Fatty Acid Casitone Media |
| 180 | Escherichia fergusonii | Human - fecal | healthy adult ♂ | Yeast Fatty Acid Casitone Media |
| 181 | Escherichia fergusonii | Human - fecal | healthy child ♀ | Yeast Fatty Acid Casitone Media |
| 182 | Eubacterium hallii | Human - fecal | healthy adult ♀ | Yeast Fatty Acid Casitone Media |
| 183 | Eubacterium ventriosum | Human - fecal | healthy child ♀ | Yeast Fatty Acid Casitone Media |
| 184 | Faecalibacterium prausnitzii | Human - fecal | healthy child ♀ | Yeast Fatty Acid Casitone Media |
| 185 | Faecalibacterium prausnitzii | Human - fecal | healthy child ♀ | Yeast Fatty Acid Casitone Media |
| 186 | Faecalibacterium prausnitzii | Human - fecal | healthy adult ♂ | Yeast Fatty Acid Casitone Media |
| 187 | Faecalibacterium prausnitzii | Human - fecal | healthy child ♀ | Yeast Fatty Acid Casitone Media |
| 188 | Faecalibacterium prausnitzii | Human - fecal | healthy adult ♂ | Yeast Fatty Acid Casitone Media |
| 189 | Faecalibacterium prausnitzii | Human - fecal | healthy child ♀ | Yeast Fatty Acid Casitone Media |
| 190 | Faecalibacterium prausnitzii | Human - fecal | healthy adult ♂ | Yeast Fatty Acid Casitone Media |
| 191 | Faecalibacterium prausnitzii | Human - fecal | healthy adult ♂ | Yeast Fatty Acid Casitone Media |
| 192 | Faecalibacterium prausnitzii | Human - fecal | healthy adult ♂ | Yeast Fatty Acid Casitone Media |
| 193 | Faecalibacterium prausnitzii | Human - fecal | healthy child ♀ | Yeast Fatty Acid Casitone Media |
| 194 | Faecalibacterium prausnitzii | Human - fecal | healthy child ♀ | Yeast Fatty Acid Casitone Media |
| 195 | Faecalibacterium prausnitzii | Human - fecal | healthy child ♀ | Yeast Fatty Acid Casitone Media |
| 196 | Faecalibacterium prausnitzii | Human - fecal | healthy child ♀ | Yeast Fatty Acid Casitone Media |
| 197 | Faecalibacterium prausnitzii | Human - fecal | healthy child ♀ | Yeast Fatty Acid Casitone Media |
| 198 | Faecalibacterium prausnitzii | Human - fecal | healthy child ♀ | Yeast Fatty Acid Casitone Media |
| 199 | Faecalibacterium prausnitzii | Human - fecal | healthy child ♀ | Yeast Fatty Acid Casitone Media |
| 200 | Holdemanella biforme | Human - fecal | healthy child ♀ | Yeast Fatty Acid Casitone Media |
| 201 | Holdemanella biforme | Human - fecal | healthy adult ♂ | Yeast Fatty Acid Casitone Media |
| 202 | Holdemanella biforme | Human - fecal | healthy adult ♀ | Yeast Fatty Acid Casitone Media |
| 203 | Hungatella effluvia | Human - fecal | healthy child ♀ | Yeast Fatty Acid Casitone Media |
| 204 | Hungatella hathewayi | Human - fecal | healthy child ♀ | Yeast Fatty Acid Casitone Media |
| 205 | Lachnoclostridium aerotolerans | Human - fecal | healthy child ♀ | Yeast Fatty Acid Casitone Media |
| 206 | Lachnoclostridium aerotolerans | Human - fecal | healthy child ♀ | Yeast Fatty Acid Casitone Media |
| 207 | Lachnoclostridium aldenense | Human - fecal | healthy adult ♂ | Yeast Fatty Acid Casitone Media |
| 208 | Lachnoclostridium asparagiforme | Human - fecal | healthy child ♀ | Yeast Fatty Acid Casitone Media |
| 209 | Lachnoclostridium bolteae | Human - fecal | healthy child ♀ | Yeast Fatty Acid Casitone Media |
| 210 | Lachnoclostridium lavalense | Human - fecal | healthy child ♀ | Yeast Fatty Acid Casitone Media |
| 211 | Lachnoclostridium symbiosum | Human - fecal | healthy adult ♂ | Yeast Fatty Acid Casitone Media |

TABLE 3-continued

Species, Source, and Isolation Media Information for Isolate Samples (Strains) 1-251

| Isolate Number | Species | Source | Source ID | Isolation Media |
|---|---|---|---|---|
| 212 | *Lachnospira pectinoschiza* | Human - fecal | healthy adult ♀ | Yeast Fatty Acid Casitone Media |
| 213 | *Lactobacillus coleohominis* | Human - vaginal | healthy adult ♀ | de Man Rogosa Sharpe Media |
| 214 | *Lactobacillus crispatus* | Human - vaginal | healthy adult ♀ | de Man Rogosa Sharpe Media |
| 215 | *Lactobacillus crispatus* | Human - vaginal | healthy adult ♀ | de Man Rogosa Sharpe Media |
| 216 | *Lactobacillus crispatus* | Human - vaginal | healthy adult ♀ | de Man Rogosa Sharpe Media |
| 217 | *Lactobacillus gasseri* | *Mus musculus* - fecal | C57/blk6 ♀ | de Man Rogosa Sharpe Media |
| 218 | *Lactobacillus jensenii* | Human - vaginal | healthy adult ♀ | de Man Rogosa Sharpe Media |
| 219 | *Lactobacillus jensenii* | Human - vaginal | healthy adult ♀ | de Man Rogosa Sharpe Media |
| 220 | *Lactobacillus jensenii* | Human - vaginal | healthy adult ♀ | de Man Rogosa Sharpe Media |
| 221 | *Lactobacillus jensenii* | Human - vaginal | healthy adult ♀ | de Man Rogosa Sharpe Media |
| 222 | *Lactobacillus jensenii* | Human - vaginal | healthy adult ♀ | de Man Rogosa Sharpe Media |
| 223 | *Lactobacillus johnsonii* | *Mus musculus* - fecal | C57/blk6 ♀ | de Man Rogosa Sharpe Media |
| 224 | *Lactobacillus johnsonii* | *Mus musculus* - fecal | C57/blk6 ♀ | de Man Rogosa Sharpe Media |
| 225 | *Lactobacillus johnsonii* | *Mus musculus* - fecal | C57/blk6 ♀ | de Man Rogosa Sharpe Media |
| 226 | *Lactobacillus johnsonii* | *Mus musculus* - fecal | C57/blk6 ♀ | de Man Rogosa Sharpe Media |
| 227 | *Lactonifactor longoviformis* | Human - fecal | healthy child ♀ | Yeast Fatty Acid Casitone Media |
| 228 | *Longibaculum muris* | Human - fecal | healthy child ♀ | Yeast Fatty Acid Casitone Media |
| 229 | *Longibaculum muris* | Human - fecal | healthy child ♀ | Yeast Fatty Acid Casitone Media |
| 230 | *Longibaculum muris* | Human - fecal | healthy child ♀ | Yeast Fatty Acid Casitone Media |
| 231 | *Longibaculum muris* | Human - fecal | healthy child ♀ | Yeast Fatty Acid Casitone Media |
| 232 | *Muribaculum intestinale* | Human - fecal | healthy child ♀ | Yeast Fatty Acid Casitone Media |
| 233 | *Oscillibacter ruminantium* | Human - fecal | healthy child ♀ | Yeast Fatty Acid Casitone Media |
| 234 | *Oscillibacter ruminantium* | Human - fecal | healthy child ♀ | Yeast Fatty Acid Casitone Media |
| 235 | *Oscillibacter ruminantium* | Human - fecal | healthy child ♀ | Yeast Fatty Acid Casitone Media |
| 236 | *Oscillibacter ruminantium* | Human - fecal | healthy child ♀ | Yeast Fatty Acid Casitone Media |
| 237 | *Parabacteroides distasonis* | Human - fecal | healthy child ♀ | Yeast Fatty Acid Casitone Media |
| 238 | *Parabacteroides merdae* | Human - fecal | healthy child ♀ | Yeast Fatty Acid Casitone Media |
| 239 | *Parabacteroides merdae* | Human - fecal | healthy child ♀ | Yeast Fatty Acid Casitone Media |
| 240 | *Parabacteroides merdae* | Human - fecal | healthy child ♀ | Yeast Fatty Acid Casitone Media |
| 241 | *Parabacteroides merdae* | Human - fecal | healthy child ♀ | Yeast Fatty Acid Casitone Media |
| 242 | *Parabacteroides merdae* | Human - fecal | healthy child ♀ | Yeast Fatty Acid Casitone Media |
| 243 | *Propionibacterium acnes* | *Mus musculus* - fecal | C57/blk6 ♀ | Mucin Minimal Media |
| 244 | *Roseburia inulinivorans* | Human - fecal | healthy child ♀ | Yeast Fatty Acid Casitone Media |
| 245 | *Roseburia inulinivorans* | Human - fecal | healthy child ♀ | Yeast Fatty Acid Casitone Media |
| 246 | *Roseburia inulinivorans* | Human - fecal | healthy child ♀ | Yeast Fatty Acid Casitone Media |
| 247 | *Ruminococcus bromii* | Human - fecal | healthy child ♀ | Yeast Fatty Acid Casitone Media |
| 248 | *Shigella flexneri* | Human - fecal | healthy child ♀ | Yeast Fatty Acid Casitone Media |
| 249 | *Staphylococcus epidermidis* | Human - fecal | healthy adult ♀ | Yeast Fatty Acid Casitone Media |

TABLE 3-continued

Species, Source, and Isolation Media Information for Isolate Samples (Strains) 1-251

| Isolate Number | Species | Source | Source ID | Isolation Media |
|---|---|---|---|---|
| 250 | Staphylococcus warneri | Human - fecal | healthy child ♀ | Yeast Fatty Acid Casitone Media |
| 251 | Sutterella wadsworthensis | Mus musculus - fecal | C57/blk6 ♀ | Mucin Minimal Media |

TABLE 4

16S-Based PCR Results Obtained for Isolate Samples 1-251

| Isolate Number | Quality Score (QS) | Continuous Reading Length (CRL) | Query cover | Identification |
|---|---|---|---|---|
| 1 | 45 | 993 | 0.9 | 0.99 |
| 2 | 48 | 1034 | 0.97 | 0.98 |
| 3 | 46 | 1018 | 0.92 | 0.98 |
| 4 | 47 | 1001 | 0.95 | 0.98 |
| 5 | 47 | 946 | 0.96 | 0.98 |
| 6 | 48 | 931 | 0.95 | 0.99 |
| 7 | 48 | 919 | 0.95 | 0.99 |
| 8 | 46 | 966 | 0.95 | 0.98 |
| 9 | 45 | 921 | 0.95 | 0.97 |
| 10 | 45 | 982 | 0.96 | 0.98 |
| 11 | 49 | 919 | 0.96 | 0.99 |
| 12 | 50 | 913 | 0.95 | 0.99 |
| 13 | 46 | 942 | 0.96 | 0.98 |
| 14 | 49 | 944 | 0.97 | 0.99 |
| 15 | 49 | 903 | 0.95 | 0.99 |
| 16 | 48 | 936 | 0.96 | 0.99 |
| 17 | 44 | 932 | 0.95 | 0.98 |
| 18 | 45 | 923 | 0.95 | 0.98 |
| 19 | 48 | 898 | 0.96 | 0.98 |
| 20 | 47 | 937 | 0.94 | 0.99 |
| 21 | 45 | 949 | 0.95 | 0.98 |
| 22 | 47 | 936 | 0.95 | 0.98 |
| 23 | 45 | 931 | 0.95 | 0.98 |
| 24 | 48 | 952 | 0.95 | 0.97 |
| 25 | 47 | 921 | 0.96 | 0.99 |
| 26 | 48 | 954 | 0.96 | 0.99 |
| 27 | 48 | 952 | 0.96 | 0.99 |
| 28 | 47 | 937 | 0.96 | 0.98 |
| 29 | 43 | 895 | 0.95 | 0.97 |
| 30 | 46 | 968 | 0.96 | 0.98 |
| 31 | 47 | 950 | 0.95 | 0.99 |
| 32 | 46 | 942 | 0.96 | 0.98 |
| 33 | 42 | 918 | 0.96 | 0.96 |
| 34 | 45 | 920 | 0.96 | 0.98 |
| 35 | 48 | 914 | 0.95 | 0.99 |
| 36 | 47 | 934 | 0.95 | 0.98 |
| 37 | 47 | 937 | 0.95 | 0.99 |
| 38 | 49 | 907 | 0.95 | 0.98 |
| 39 | 45 | 918 | 0.95 | 0.98 |
| 40 | 45 | 907 | 0.94 | 0.98 |
| 41 | 39 | 933 | 0.89 | 0.96 |
| 42 | 47 | 995 | 0.96 | 0.94 |
| 43 | 50 | 1018 | 0.97 | 0.99 |
| 44 | 50 | 1016 | 0.98 | 0.98 |
| 45 | 48 | 999 | 0.96 | 0.99 |
| 46 | 51 | 1003 | 0.97 | 0.99 |
| 47 | 41 | 993 | 0.97 | 0.99 |
| 48 | 47 | 996 | 0.94 | 0.98 |
| 49 | 48 | 992 | 0.96 | 0.98 |
| 50 | 45 | 988 | 0.93 | 0.97 |
| 51 | 47 | 993 | 0.94 | 0.98 |
| 52 | 47 | 999 | 0.94 | 0.98 |
| 53 | 48 | 960 | 0.96 | 0.98 |
| 54 | 46 | 992 | 0.89 | 0.98 |
| 55 | 43 | 966 | 0.96 | 0.85 |
| 56 | 37 | 269 | 0.99 | 0.88 |
| 57 | 49 | 1014 | 0.97 | 0.99 |
| 58 | 43 | 958 | 0.87 | 0.97 |
| 59 | 49 | 1002 | 0.96 | 0.98 |
| 60 | 49 | 991 | 0.97 | 0.98 |
| 61 | 48 | 994 | 0.97 | 0.98 |
| 62 | 50 | 991 | 0.97 | 0.98 |
| 63 | 46 | 992 | 0.97 | 0.98 |
| 64 | 50 | 994 | 0.97 | 0.98 |
| 65 | 49 | 979 | 0.96 | 0.98 |
| 66 | 50 | 996 | 0.96 | 0.99 |
| 67 | 50 | 987 | 0.97 | 0.98 |
| 68 | 48 | 1006 | 0.96 | 0.98 |
| 69 | 48 | 1016 | 0.95 | 0.97 |
| 70 | 40 | 799 | 0.78 | 0.98 |
| 71 | 49 | 998 | 0.97 | 0.98 |
| 72 | 49 | 1028 | 0.98 | 0.98 |
| 73 | 50 | 991 | 0.97 | 0.99 |
| 74 | 47 | 1033 | 0.97 | 0.99 |
| 75 | 49 | 999 | 0.97 | 0.99 |
| 76 | 47 | 1048 | 0.97 | 0.99 |
| 77 | 50 | 986 | 0.98 | 0.99 |
| 78 | 49 | 976 | 0.97 | 0.99 |
| 79 | 47 | 1007 | 0.97 | 0.97 |
| 80 | 48 | 1044 | 0.97 | 0.97 |
| 81 | 50 | 1014 | 0.97 | 0.99 |
| 82 | 47 | 991 | 0.97 | 0.98 |
| 83 | 47 | 977 | 0.97 | 0.98 |
| 84 | 47 | 988 | 0.97 | 0.98 |
| 85 | 48 | 1000 | 0.96 | 0.99 |
| 86 | 50 | 976 | 0.97 | 0.98 |
| 87 | 48 | 1013 | 0.96 | 0.99 |
| 88 | 49 | 918 | 0.96 | 0.99 |
| 89 | 49 | 1016 | 0.95 | 0.98 |
| 90 | 46 | 1009 | 0.97 | 0.96 |
| 91 | 46 | 1002 | 0.94 | 0.97 |
| 92 | 49 | 1070 | 0.97 | 0.99 |
| 93 | 49 | 989 | 0.96 | 0.98 |
| 94 | 46 | 1015 | 0.95 | 0.98 |
| 95 | 42 | 982 | 0.86 | 0.98 |
| 96 | 50 | 987 | 0.96 | 0.99 |
| 97 | 49 | 1009 | 0.97 | 0.99 |
| 98 | 49 | 1010 | 0.94 | 0.98 |
| 99 | 49 | 1002 | 0.94 | 0.98 |
| 100 | 48 | 1000 | 0.97 | 0.97 |
| 101 | 48 | 996 | 0.92 | 0.99 |
| 102 | 48 | 1007 | 0.96 | 0.99 |
| 103 | 49 | 1016 | 0.94 | 0.99 |
| 104 | 49 | 1011 | 0.96 | 0.99 |
| 105 | 48 | 1016 | 0.96 | 0.99 |
| 106 | 49 | 1011 | 0.97 | 0.99 |
| 107 | 49 | 1031 | 0.97 | 0.99 |
| 108 | 46 | 1039 | 0.9 | 0.99 |
| 109 | 48 | 1014 | 0.97 | 0.99 |
| 110 | 48 | 1003 | 0.97 | 0.99 |
| 111 | 43 | 975 | 0.94 | 0.96 |
| 112 | 50 | 997 | 0.94 | 0.99 |
| 113 | 46 | 1010 | 0.88 | 0.98 |
| 114 | 49 | 1042 | 0.97 | 0.98 |
| 115 | 50 | 1021 | 0.97 | 0.98 |
| 116 | 45 | 990 | 0.83 | 0.98 |
| 117 | 39 | 1004 | 0.79 | 0.98 |
| 118 | 47 | 1064 | 0.93 | 0.99 |

TABLE 4-continued

16S-Based PCR Results Obtained for Isolate Samples 1-251

| Isolate Number | Quality Score (QS) | Continuous Reading Length (CRL) | Query cover | Identification |
|---|---|---|---|---|
| 119 | 47 | 1019 | 0.97 | 0.96 |
| 120 | 43 | 934 | 0.91 | 0.94 |
| 121 | 45 | 948 | 0.95 | 0.89 |
| 122 | 38 | 939 | 0.96 | 0.8 |
| 123 | 49 | 990 | 0.96 | 0.97 |
| 124 | 47 | 1043 | 0.91 | 0.98 |
| 125 | 47 | 982 | 0.93 | 0.98 |
| 126 | 46 | 975 | 0.93 | 0.96 |
| 127 | 46 | 976 | 0.95 | 0.95 |
| 128 | 47 | 972 | 0.96 | 0.97 |
| 129 | 46 | 988 | 0.91 | 0.97 |
| 130 | 47 | 1018 | 0.91 | 0.98 |
| 131 | 48 | 993 | 0.94 | 0.97 |
| 132 | 46 | 993 | 0.89 | 0.97 |
| 133 | 25 | 144 | 0.91 | 0.83 |
| 134 | 48 | 1034 | 0.98 | 0.98 |
| 135 | 45 | 1054 | 0.94 | 0.98 |
| 136 | 48 | 1006 | 0.97 | 0.94 |
| 137 | 50 | 975 | 0.95 | 0.95 |
| 138 | 44 | 976 | 0.88 | 0.98 |
| 139 | 50 | 961 | 0.96 | 0.98 |
| 140 | 47 | 978 | 0.97 | 0.97 |
| 141 | 48 | 1007 | 0.97 | 0.97 |
| 142 | 47 | 970 | 0.97 | 0.97 |
| 143 | 47 | 948 | 0.97 | 0.97 |
| 144 | 47 | 988 | 0.97 | 0.97 |
| 145 | 48 | 974 | 0.96 | 0.98 |
| 146 | 48 | 1019 | 0.95 | 0.98 |
| 147 | 43 | 932 | 0.91 | 0.96 |
| 148 | 46 | 982 | 0.97 | 0.89 |
| 149 | 25 | 535 | 0.93 | 0.9 |
| 150 | 32 | 373 | 0.95 | 0.93 |
| 151 | 48 | 1030 | 0.97 | 0.98 |
| 152 | 43 | 975 | 0.94 | 0.98 |
| 153 | 49 | 1040 | 0.96 | 0.98 |
| 154 | 49 | 1013 | 0.97 | 0.98 |
| 155 | 48 | 997 | 0.97 | 0.97 |
| 156 | 49 | 1018 | 0.96 | 0.97 |
| 157 | 48 | 1026 | 0.97 | 0.97 |
| 158 | 48 | 995 | 0.89 | 0.98 |
| 159 | 49 | 1011 | 0.9 | 0.99 |
| 160 | 48 | 1043 | 0.89 | 0.99 |
| 161 | 36 | 345 | 0.97 | 0.9 |
| 162 | 49 | 991 | 0.98 | 0.99 |
| 163 | 49 | 1015 | 0.96 | 0.99 |
| 164 | 48 | 991 | 0.96 | 0.99 |
| 165 | 49 | 1028 | 0.97 | 0.98 |
| 166 | 48 | 1024 | 0.97 | 0.98 |
| 167 | 49 | 1025 | 0.98 | 0.98 |
| 168 | 48 | 991 | 0.97 | 0.98 |
| 169 | 46 | 946 | 0.95 | 0.97 |
| 170 | 44 | 924 | 0.92 | 0.97 |
| 171 | 47 | 936 | 0.96 | 0.97 |
| 172 | 48 | 1038 | 0.97 | 0.98 |
| 173 | 48 | 963 | 0.97 | 0.98 |
| 174 | 48 | 1041 | 0.97 | 0.99 |
| 175 | 48 | 1003 | 0.97 | 0.99 |
| 176 | 49 | 975 | 0.96 | 0.99 |
| 177 | 50 | 976 | 0.98 | 0.99 |
| 178 | 49 | 999 | 0.97 | 0.98 |
| 179 | 49 | 998 | 0.94 | 0.98 |
| 180 | 48 | 1046 | 0.97 | 0.98 |
| 181 | 44 | 962 | 0.94 | 0.98 |
| 182 | 44 | 912 | 0.88 | 0.96 |
| 183 | 45 | 984 | 0.91 | 0.96 |
| 184 | 48 | 1040 | 0.97 | 0.97 |
| 185 | 46 | 944 | 0.92 | 0.97 |
| 186 | 46 | 922 | 0.96 | 0.96 |
| 187 | 48 | 1015 | 0.97 | 0.97 |
| 188 | 46 | 926 | 0.97 | 0.96 |
| 189 | 49 | 1002 | 0.97 | 0.97 |
| 190 | 46 | 926 | 0.97 | 0.97 |
| 191 | 46 | 922 | 0.97 | 0.96 |
| 192 | 46 | 930 | 0.96 | 0.96 |
| 193 | 48 | 948 | 0.97 | 0.96 |
| 194 | 46 | 1033 | 0.97 | 0.96 |
| 195 | 49 | 1023 | 0.97 | 0.96 |
| 196 | 48 | 1037 | 0.97 | 0.97 |
| 197 | 48 | 1006 | 0.97 | 0.97 |
| 198 | 48 | 1028 | 0.97 | 0.97 |
| 199 | 49 | 1008 | 0.97 | 0.97 |
| 200 | 47 | 986 | 0.97 | 0.97 |
| 201 | 46 | 983 | 0.97 | 0.97 |
| 202 | 43 | 998 | 0.96 | 0.95 |
| 203 | 43 | 984 | 0.97 | 0.98 |
| 204 | 45 | 978 | 0.97 | 0.97 |
| 205 | 31 | 327 | 0.9 | 0.88 |
| 206 | 30 | 656 | 0.9 | 0.88 |
| 207 | 45 | 951 | 0.85 | 0.97 |
| 208 | 43 | 648 | 0.91 | 0.95 |
| 209 | 46 | 1017 | 0.93 | 0.91 |
| 210 | 44 | 1024 | 0.94 | 0.88 |
| 211 | 48 | 999 | 0.96 | 0.96 |
| 212 | 40 | 943 | 0.93 | 0.96 |
| 213 | 42 | 809 | 0.87 | 0.97 |
| 214 | 40 | 710 | 0.8 | 0.97 |
| 215 | 43 | 852 | 0.89 | 0.98 |
| 216 | 41 | 771 | 0.84 | 0.99 |
| 217 | 39 | 923 | 0.95 | 0.98 |
| 218 | 42 | 881 | 0.91 | 0.96 |
| 219 | 41 | 799 | 0.85 | 0.97 |
| 220 | 41 | 774 | 0.86 | 0.96 |
| 221 | 40 | 794 | 0.83 | 0.96 |
| 222 | 43 | 869 | 0.9 | 0.97 |
| 223 | 49 | 902 | 0.96 | 0.99 |
| 224 | 47 | 930 | 0.96 | 0.98 |
| 225 | 48 | 908 | 0.95 | 0.98 |
| 226 | 44 | 899 | 0.94 | 0.97 |
| 227 | 44 | 983 | 0.98 | 0.92 |
| 228 | 51 | 998 | 0.97 | 0.95 |
| 229 | 50 | 987 | 0.98 | 0.95 |
| 230 | 51 | 984 | 0.98 | 0.95 |
| 231 | 50 | 1029 | 0.98 | 0.95 |
| 232 | 47 | 1002 | 0.94 | 0.84 |
| 233 | 43 | 986 | 0.93 | 0.91 |
| 234 | 39 | 343 | 0.93 | 0.91 |
| 235 | 38 | 813 | 0.9 | 0.9 |
| 236 | 50 | 999 | 0.96 | 0.95 |
| 237 | 28 | 867 | 0.94 | 0.81 |
| 238 | 48 | 990 | 0.97 | 0.99 |
| 239 | 49 | 978 | 0.97 | 0.99 |
| 240 | 48 | 1019 | 0.96 | 0.99 |
| 241 | 49 | 1007 | 0.97 | 0.99 |
| 242 | 49 | 1025 | 0.96 | 0.99 |
| 243 | 48 | 868 | 0.96 | 0.95 |
| 244 | 45 | 966 | 0.96 | 0.96 |
| 245 | 46 | 974 | 0.97 | 0.97 |
| 246 | 48 | 981 | 0.97 | 0.98 |
| 247 | 46 | 975 | 0.96 | 0.96 |
| 248 | 48 | 954 | 0.97 | 0.97 |
| 249 | 46 | 1006 | 0.91 | 0.98 |
| 250 | 50 | 962 | 0.97 | 0.99 |
| 251 | 43 | 836 | 0.93 | 0.97 |

TABLE 5

Taxonomy Information for All Isolate Samples 1-251

| Isolate Number | Phylum | Class | Family | Genus | Species |
|---|---|---|---|---|---|
| 1 | Verrucomicrobia | Verrucomicrobiae | Akkermansiaceae | *Akkermansia* | *muciniphila* |
| 2 | Verrucomicrobia | Verrucomicrobiae | Akkermansiaceae | *Akkermansia* | *muciniphila* |
| 3 | Verrucomicrobia | Verrucomicrobiae | Akkermansiaceae | *Akkermansia* | *muciniphila* |
| 4 | Verrucomicrobia | Verrucomicrobiae | Akkermansiaceae | *Akkermansia* | *muciniphila* |
| 5 | Verrucomicrobia | Verrucomicrobiae | Akkermansiaceae | *Akkermansia* | *muciniphila* |
| 6 | Verrucomicrobia | Verrucomicrobiae | Akkermansiaceae | *Akkermansia* | *muciniphila* |
| 7 | Verrucomicrobia | Verrucomicrobiae | Akkermansiaceae | *Akkermansia* | *muciniphila* |
| 8 | Verrucomicrobia | Verrucomicrobiae | Akkermansiaceae | *Akkermansia* | *muciniphila* |
| 9 | Verrucomicrobia | Verrucomicrobiae | Akkermansiaceae | *Akkermansia* | *muciniphila* |
| 10 | Verrucomicrobia | Verrucomicrobiae | Akkermansiaceae | *Akkermansia* | *muciniphila* |
| 11 | Verrucomicrobia | Verrucomicrobiae | Akkermansiaceae | *Akkermansia* | *muciniphila* |
| 12 | Verrucomicrobia | Verrucomicrobiae | Akkermansiaceae | *Akkermansia* | *muciniphila* |
| 13 | Verrucomicrobia | Verrucomicrobiae | Akkermansiaceae | *Akkermansia* | *muciniphila* |
| 14 | Verrucomicrobia | Verrucomicrobiae | Akkermansiaceae | *Akkermansia* | *muciniphila* |
| 15 | Verrucomicrobia | Verrucomicrobiae | Akkermansiaceae | *Akkermansia* | *muciniphila* |
| 16 | Verrucomicrobia | Verrucomicrobiae | Akkermansiaceae | *Akkermansia* | *muciniphila* |
| 17 | Verrucomicrobia | Verrucomicrobiae | Akkermansiaceae | *Akkermansia* | *muciniphila* |
| 18 | Verrucomicrobia | Verrucomicrobiae | Akkermansiaceae | *Akkermansia* | *muciniphila* |
| 19 | Verrucomicrobia | Verrucomicrobiae | Akkermansiaceae | *Akkermansia* | *muciniphila* |
| 20 | Verrucomicrobia | Verrucomicrobiae | Akkermansiaceae | *Akkermansia* | *muciniphila* |
| 21 | Verrucomicrobia | Verrucomicrobiae | Akkermansiaceae | *Akkermansia* | *muciniphila* |
| 22 | Verrucomicrobia | Verrucomicrobiae | Akkermansiaceae | *Akkermansia* | *muciniphila* |
| 23 | Verrucomicrobia | Verrucomicrobiae | Akkermansiaceae | *Akkermansia* | *muciniphila* |
| 24 | Verrucomicrobia | Verrucomicrobiae | Akkermansiaceae | *Akkermansia* | *muciniphila* |
| 25 | Verrucomicrobia | Verrucomicrobiae | Akkermansiaceae | *Akkermansia* | *muciniphila* |
| 26 | Verrucomicrobia | Verrucomicrobiae | Akkermansiaceae | *Akkermansia* | *muciniphila* |
| 27 | Verrucomicrobia | Verrucomicrobiae | Akkermansiaceae | *Akkermansia* | *muciniphila* |
| 28 | Verrucomicrobia | Verrucomicrobiae | Akkermansiaceae | *Akkermansia* | *muciniphila* |
| 29 | Verrucomicrobia | Verrucomicrobiae | Akkermansiaceae | *Akkermansia* | *muciniphila* |
| 30 | Verrucomicrobia | Verrucomicrobiae | Akkermansiaceae | *Akkermansia* | *muciniphila* |
| 31 | Verrucomicrobia | Verrucomicrobiae | Akkermansiaceae | *Akkermansia* | *muciniphila* |
| 32 | Verrucomicrobia | Verrucomicrobiae | Akkermansiaceae | *Akkermansia* | *muciniphila* |
| 33 | Verrucomicrobia | Verrucomicrobiae | Akkermansiaceae | *Akkermansia* | *muciniphila* |
| 34 | Verrucomicrobia | Verrucomicrobiae | Akkermansiaceae | *Akkermansia* | *mucimphila* |
| 35 | Verrucomicrobia | Verrucomicrobiae | Akkermansiaceae | *Akkermansia* | *mucimphila* |
| 36 | Verrucomicrobia | Verrucomicrobiae | Akkermansiaceae | *Akkermansia* | *mucimphila* |
| 37 | Verrucomicrobia | Verrucomicrobiae | Akkermansiaceae | *Akkermansia* | *mucimphila* |
| 38 | Verrucomicrobia | Verrucomicrobiae | Akkermansiaceae | *Akkermansia* | *mucimphila* |
| 39 | Verrucomicrobia | Verrucomicrobiae | Akkermansiaceae | *Akkermansia* | *mucimphila* |
| 40 | Verrucomicrobia | Verrucomicrobiae | Akkermansiaceae | *Akkermansia* | *mucimphila* |
| 41 | Firmicutes | Clostridia | Lachnospiracea | *Anaerostipes* | *hadrus* |
| 42 | Firmicutes | Clostridia | Lachnospiraceae | *Anaerotignum* | *lactatifermentans* |
| 43 | Bacteroidetes | Bacteroidia | Bacteroidaceae | *Bacteroides* | *caccae* |
| 44 | Bacteroidetes | Bacteroidia | Bacteroidaceae | *Bacteroides* | *caccae* |
| 45 | Bacteroidetes | Bacteroidia | Bacteroidaceae | *Bacteroides* | *dorei* |
| 46 | Bacteroidetes | Bacteroidia | Bacteroidaceae | *Bacteroides* | *dorei* |
| 47 | Bacteroidetes | Bacteroidia | Bacteroidaceae | *Bacteroides* | *dorei* |
| 48 | Bacteroidetes | Bacteroidia | Bacteroidaceae | *Bacteroides* | *faecis* |
| 49 | Bacteroidetes | Bacteroidia | Bacteroidaceae | *Bacteroides* | *faecis* |
| 50 | Bacteroidetes | Bacteroidia | Bacteroidaceae | *Bacteroides* | *faecis* |
| 51 | Bacteroidetes | Bacteroidia | Bacteroidaceae | *Bacteroides* | *faecis* |
| 52 | Bacteroidetes | Bacteroidia | Bacteroidaceae | *Bacteroides* | *faecis* |
| 53 | Bacteroidetes | Bacteroidia | Bacteroidaceae | *Bacteroides* | *faecis* |
| 54 | Bacteroidetes | Bacteroidia | Bacteroidaceae | *Bacteroides* | *faecis* |
| 55 | Bacteroidetes | Bacteroidia | Bacteroidaceae | *Bacteroides* | *faecis* |
| 56 | Bacteroidetes | Bacteroidia | Bacteroidaceae | *Bacteroides* | *faecis* |
| 57 | Bacteroidetes | Bacteroidia | Bacteroidaceae | *Bacteroides* | *faecis* |
| 58 | Bacteroidetes | Bacteroidia | Bacteroidaceae | *Bacteroides* | *finegoldii* |
| 59 | Bacteroidetes | Bacteroidia | Bacteroidaceae | *Bacteroides* | *fragilis* |
| 60 | Bacteroidetes | Bacteroidia | Bacteroidaceae | *Bacteroides* | *fragilis* |
| 61 | Bacteroidetes | Bacteroidia | Bacteroidaceae | *Bacteroides* | *fragilis* |
| 62 | Bacteroidetes | Bacteroidia | Bacteroidaceae | *Bacteroides* | *fragilis* |
| 63 | Bacteroidetes | Bacteroidia | Bacteroidaceae | *Bacteroides* | *fragilis* |
| 64 | Bacteroidetes | Bacteroidia | Bacteroidaceae | *Bacteroides* | *fragilis* |
| 65 | Bacteroidetes | Bacteroidia | Bacteroidaceae | *Bacteroides* | *fragilis* |
| 66 | Bacteroidetes | Bacteroidia | Bacteroidaceae | *Bacteroides* | *fragilis* |
| 67 | Bacteroidetes | Bacteroidia | Bacteroidaceae | *Bacteroides* | *fragilis* |
| 68 | Bacteroidetes | Bacteroidia | Bacteroidaceae | *Bacteroides* | *fragilis* |
| 69 | Bacteroidetes | Bacteroidia | Bacteroidaceae | *Bacteroides* | *fragilis* |
| 70 | Bacteroidetes | Bacteroidia | Bacteroidaceae | *Bacteroides* | *fragilis* |
| 71 | Bacteroidetes | Bacteroidia | Bacteroidaceae | *Bacteroides* | *fragilis* |
| 72 | Bacteroidetes | Bacteroidia | Bacteroidaceae | *Bacteroides* | *fragilis* |
| 73 | Bacteroidetes | Bacteroidia | Bacteroidaceae | *Bacteroides* | *intestinalis* |
| 74 | Bacteroidetes | Bacteroidia | Bacteroidaceae | *Bacteroides* | *stercoris* |
| 75 | Bacteroidetes | Bacteroidia | Bacteroidaceae | *Bacteroides* | *stercoris* |

TABLE 5-continued

Taxonomy Information for All Isolate Samples 1-251

| Isolate Number | Phylum | Class | Family | Genus | Species |
|---|---|---|---|---|---|
| 76 | Bacteroidetes | Bacteroidia | Bacteroidaceae | *Bacteroides* | *stercoris* |
| 77 | Bacteroidetes | Bacteroidia | Bacteroidaceae | *Bacteroides* | *stercoris* |
| 78 | Bacteroidetes | Bacteroidia | Bacteroidaceae | *Bacteroides* | *stercoris* |
| 79 | Bacteroidetes | Bacteroidia | Bacteroidaceae | *Bacteroides* | *stercoris* |
| 80 | Bacteroidetes | Bacteroidia | Bacteroidaceae | *Bacteroides* | *stercoris* |
| 81 | Bacteroidetes | Bacteroidia | Bacteroidaceae | *Bacteroides* | *stercoris* |
| 82 | Bacteroidetes | Bacteroidia | Bacteroidaceae | *Bacteroides* | *thetaiotaomicron* |
| 83 | Bacteroidetes | Bacteroidia | Bacteroidaceae | *Bacteroides* | *thetaiotaomicron* |
| 84 | Bacteroidetes | Bacteroidia | Bacteroidaceae | *Bacteroides* | *thetaiotaomicron* |
| 85 | Bacteroidetes | Bacteroidia | Bacteroidaceae | *Bacteroides* | *thetaiotaomicron* |
| 86 | Bacteroidetes | Bacteroidia | Bacteroidaceae | *Bacteroides* | *thetaiotaomicron* |
| 87 | Bacteroidetes | Bacteroidia | Bacteroidaceae | *Bacteroides* | *thetaiotaomicron* |
| 88 | Bacteroidetes | Bacteroidia | Bacteroidaceae | *Bacteroides* | *thetaiotaomicron* |
| 89 | Bacteroidetes | Bacteroidia | Bacteroidaceae | *Bacteroides* | *thetaiotaomicron* |
| 90 | Bacteroidetes | Bacteroidia | Bacteroidaceae | *Bacteroides* | *thetaiotaomicron* |
| 91 | Bacteroidetes | Bacteroidia | Bacteroidaceae | *Bacteroides* | *thetaiotaomicron* |
| 92 | Bacteroidetes | Bacteroidia | Bacteroidaceae | *Bacteroides* | *uniformis* |
| 93 | Bacteroidetes | Bacteroidia | Bacteroidaceae | *Bacteroides* | *uniformis* |
| 94 | Bacteroidetes | Bacteroidia | Bacteroidaceae | *Bacteroides* | *uniformis* |
| 95 | Bacteroidetes | Bacteroidia | Bacteroidaceae | *Bacteroides* | *vulgatus* |
| 96 | Bacteroidetes | Bacteroidia | Bacteroidaceae | *Bacteroides* | *vulgatus* |
| 97 | Bacteroidetes | Bacteroidia | Bacteroidaceae | *Bacteroides* | *vulgatus* |
| 98 | Bacteroidetes | Bacteroidia | Bacteroidaceae | *Bacteroides* | *vulgatus* |
| 99 | Bacteroidetes | Bacteroidia | Bacteroidaceae | *Bacteroides* | *vulgatus* |
| 100 | Bacteroidetes | Bacteroidia | Bacteroidaceae | *Bacteroides* | *vulgatus* |
| 101 | Bacteroidetes | Bacteroidia | Bacteroidaceae | *Bacteroides* | *vulgatus* |
| 102 | Bacteroidetes | Bacteroidia | Bacteroidaceae | *Bacteroides* | *vulgatus* |
| 103 | Bacteroidetes | Bacteroidia | Bacteroidaceae | *Bacteroides* | *vulgatus* |
| 104 | Bacteroidetes | Bacteroidia | Bacteroidaceae | *Bacteroides* | *vulgatus* |
| 105 | Bacteroidetes | Bacteroidia | Bacteroidaceae | *Bacteroides* | *vulgatus* |
| 106 | Bacteroidetes | Bacteroidia | Bacteroidaceae | *Bacteroides* | *vulgatus* |
| 107 | Bacteroidetes | Bacteroidia | Bacteroidaceae | *Bacteroides* | *vulgatus* |
| 108 | Bacteroidetes | Bacteroidia | Bacteroidaceae | *Bacteroides* | *vulgatus* |
| 109 | Bacteroidetes | Bacteroidia | Bacteroidaceae | *Bacteroides* | *xylanisolvens* |
| 110 | Bacteroidetes | Bacteroidia | Bacteroidaceae | *Bacteroides* | *xylanisolvens* |
| 111 | Actinobacteria | Actinobacteria | Bifidobacteriaceae | *Bifidobacterium* | *faecale* |
| 112 | Actinobacteria | Actinobacteria | Bifidobacteriaceae | *Bifidobacterium* | *faecale* |
| 113 | Actinobacteria | Actinobacteria | Bifidobacteriaceae | *Bifidobacterium* | *longum* |
| 114 | Actinobacteria | Actinobacteria | Bifidobacteriaceae | *Bifidobacterium* | *stercoris* |
| 115 | Actinobacteria | Actinobacteria | Bifidobacteriaceae | *Bifidobacterium* | *stercoris* |
| 116 | Firmicutes | Clostridia | Lachnospiracea | *Blautia* | *faecis* |
| 117 | Firmicutes | Clostridia | Lachnospiracea | *Blautia* | *faecis* |
| 118 | Firmicutes | Clostridia | Lachnospiracea | *Blautia* | *gnavus* |
| 119 | Firmicutes | Clostridia | Lachnospiracea | *Blautia* | *luti* |
| 120 | Firmicutes | Clostridia | Lachnospiracea | *Blautia* | *obeum* |
| 121 | Firmicutes | Clostridia | Lachnospiracea | *Blautia* | *obeum* |
| 122 | Firmicutes | Clostridia | Lachnospiracea | *Blautia* | *obeum* |
| 123 | Firmicutes | Clostridia | Lachnospiracea | *Blautia* | *obeum* |
| 124 | Firmicutes | Clostridia | Lachnospiracea | *Blautia* | *obeum* |
| 125 | Firmicutes | Clostridia | Lachnospiracea | *Blautia* | *obeum* |
| 126 | Firmicutes | Clostridia | Lachnospiracea | *Blautia* | *producta* |
| 127 | Firmicutes | Clostridia | Lachnospiracea | *Blautia* | *producta* |
| 128 | Firmicutes | Clostridia | Lachnospiracea | *Blautia* | *producta* |
| 129 | Firmicutes | Clostridia | Lachnospiracea | *Blautia* | *producta* |
| 130 | Firmicutes | Clostridia | Lachnospiracea | *Blautia* | *producta* |
| 131 | Firmicutes | Clostridia | Lachnospiracea | *Blautia* | *producta* |
| 132 | Firmicutes | Clostridia | Lachnospiracea | *Blautia* | *producta* |
| 133 | Firmicutes | Clostridia | Lachnospiracea | *Blautia* | *producta* |
| 134 | Firmicutes | Clostridia | Lachnospiracea | *Blautia* | *producta* |
| 135 | Firmicutes | Clostridia | Lachnospiracea | *Blautia* | *producta* |
| 136 | Firmicutes | Clostridia | Lachnospiracea | *Blautia* | *stercoris* |
| 137 | Firmicutes | Clostridia | Lachnospiracea | *Blautia* | *stercoris* |
| 138 | Firmicutes | Clostridia | Lachnospiracea | *Blautia* | *torques* |
| 139 | Firmicutes | Clostridia | Lachnospiracea | *Blautia* | *wexlerae* |
| 140 | Firmicutes | Clostridia | Lachnospiracea | *Blautia* | *wexlerae* |
| 141 | Firmicutes | Clostridia | Lachnospiracea | *Blautia* | *wexlerae* |
| 142 | Firmicutes | Clostridia | Lachnospiracea | *Blautia* | *wexlerae* |
| 143 | Firmicutes | Clostridia | Lachnospiracea | *Blautia* | *wexlerae* |
| 144 | Firmicutes | Clostridia | Lachnospiracea | *Blautia* | *wexlerae* |
| 145 | Firmicutes | Clostridia | Lachnospiracea | *Blautia* | *wexlerae* |
| 146 | Actinobacteria | Coriobacteriia | Coriobacteriaceae | *Collinsella* | *aerofaciens* |
| 147 | Firmicutes | Clostridia | Lachnospiracea | *Coprococcus* | *comes* |
| 148 | Firmicutes | Clostridia | Lachnospiracea | *Coprococcus* | *comes* |
| 149 | Firmicutes | Clostridia | Lachnospiracea | *Coprococcus* | *comes* |
| 150 | Firmicutes | Clostridia | Lachnospiracea | *Coprococcus* | *comes* |

TABLE 5-continued

Taxonomy Information for All Isolate Samples 1-251

| Isolate Number | Phylum | Class | Family | Genus | Species |
|---|---|---|---|---|---|
| 151 | Firmicutes | Clostridia | Lachnospiracea | *Coprococcus* | *comes* |
| 152 | Firmicutes | Clostridia | Lachnospiracea | *Coprococcus* | *comes* |
| 153 | Firmicutes | Clostridia | Lachnospiracea | *Coprococcus* | *comes* |
| 154 | Firmicutes | Clostridia | Lachnospiracea | *Coprococcus* | *eutactus* |
| 155 | Firmicutes | Clostridia | Lachnospiracea | *Dorea* | *formicigenerans* |
| 156 | Firmicutes | Clostridia | Lachnospiracea | *Dorea* | *formicigenerans* |
| 157 | Firmicutes | Clostridia | Lachnospiracea | *Dorea* | *formicigenerans* |
| 158 | Firmicutes | Clostridia | Lachnospiracea | *Dorea* | *longicatena* |
| 159 | Firmicutes | Clostridia | Lachnospiracea | *Dorea* | *longicatena* |
| 160 | Firmicutes | Clostridia | Lachnospiracea | *Dorea* | *longicatena* |
| 161 | Firmicutes | Clostridia | Lachnospiraceae | *Eisenbergiella* | *massiliensis* |
| 162 | Firmicutes | Erysipelotrichia | Erysipelotrichaceae | *Erysipelatoclostridium* | *ramosum* |
| 163 | Firmicutes | Erysipelotrichia | Erysipelotrichaceae | *Erysipelatoclostridium* | *ramosum* |
| 164 | Firmicutes | Erysipelotrichia | Erysipelotrichaceae | *Erysipelatoclostridium* | *ramosum* |
| 165 | Firmicutes | Erysipelotrichia | Erysipelotrichaceae | *Erysipelatoclostridium* | *ramosum* |
| 166 | Firmicutes | Erysipelotrichia | Erysipelotrichaceae | *Erysipelatoclostridium* | *ramosum* |
| 167 | Firmicutes | Erysipelotrichia | Erysipelotrichaceae | *Erysipelatoclostridium* | *ramosum* |
| 168 | Firmicutes | Erysipelotrichia | Erysipelotrichaceae | *Erysipelatoclostridium* | *ramosum* |
| 169 | Proteobacteria | Gammaproteobacteria | Enterobacteriaceae | *Escherichia* | *fergusonii* |
| 170 | Proteobacteria | Gammaproteobacteria | Enterobacteriaceae | *Escherichia* | *fergusonii* |
| 171 | Proteobacteria | Gammaproteobacteria | Enterobacteriaceae | *Escherichia* | *fergusonii* |
| 172 | Proteobacteria | Gammaproteobacteria | Enterobacteriaceae | *Escherichia* | *fergusonii* |
| 173 | Proteobacteria | Gammaproteobacteria | Enterobacteriaceae | *Escherichia* | *fergusonii* |
| 174 | Proteobacteria | Gammaproteobacteria | Enterobacteriaceae | *Escherichia* | *fergusonii* |
| 175 | Proteobacteria | Gammaproteobacteria | Enterobacteriaceae | *Escherichia* | *fergusonii* |
| 176 | Proteobacteria | Gammaproteobacteria | Enterobacteriaceae | *Escherichia* | *fergusonii* |
| 177 | Proteobacteria | Gammaproteobacteria | Enterobacteriaceae | *Escherichia* | *fergusonii* |
| 178 | Proteobacteria | Gammaproteobacteria | Enterobacteriaceae | *Escherichia* | *fergusonii* |
| 179 | Proteobacteria | Gammaproteobacteria | Enterobacteriaceae | *Escherichia* | *fergusonii* |
| 180 | Proteobacteria | Gammaproteobacteria | Enterobacteriaceae | *Escherichia* | *fergusonii* |
| 181 | Proteobacteria | Gammaproteobacteria | Enterobacteriaceae | *Escherichia* | *fergusonii* |
| 182 | Firmicutes | Clostridia | Eubacteriaceae | *Eubacterium* | *hallii* |
| 183 | Firmicutes | Clostridia | Eubacteriaceae | *Eubacterium* | *ventriosum* |
| 184 | Firmicutes | Clostridia | Ruminococcaceae | *Faecalibacterium* | *prausnitzii* |
| 185 | Firmicutes | Clostridia | Ruminococcaceae | *Faecalibacterium* | *prausnitzii* |
| 186 | Firmicutes | Clostridia | Ruminococcaceae | *Faecalibacterium* | *prausnitzii* |
| 187 | Firmicutes | Clostridia | Ruminococcaceae | *Faecalibacterium* | *prausnitzii* |
| 188 | Firmicutes | Clostridia | Ruminococcaceae | *Faecalibacterium* | *prausnitzii* |
| 189 | Firmicutes | Clostridia | Ruminococcaceae | *Faecalibacterium* | *prausnitzii* |
| 190 | Firmicutes | Clostridia | Ruminococcaceae | *Faecalibacterium* | *prausnitzii* |
| 191 | Firmicutes | Clostridia | Ruminococcaceae | *Faecalibacterium* | *prausnitzii* |
| 192 | Firmicutes | Clostridia | Ruminococcaceae | *Faecalibacterium* | *prausnitzii* |
| 193 | Firmicutes | Clostridia | Ruminococcaceae | *Faecalibacterium* | *prausnitzii* |
| 194 | Firmicutes | Clostridia | Ruminococcaceae | *Faecalibacterium* | *prausnitzii* |
| 195 | Firmicutes | Clostridia | Ruminococcaceae | *Faecalibacterium* | *prausnitzii* |
| 196 | Firmicutes | Clostridia | Ruminococcaceae | *Faecalibacterium* | *prausnitzii* |
| 197 | Firmicutes | Clostridia | Ruminococcaceae | *Faecalibacterium* | *prausnitzii* |
| 198 | Firmicutes | Clostridia | Ruminococcaceae | *Faecalibacterium* | *prausnitzii* |
| 199 | Firmicutes | Clostridia | Ruminococcaceae | *Faecalibacterium* | *prausnitzii* |
| 200 | Firmicutes | Erysipelotrichia | Erysipelotrichaceae | *Holdemanella* | *biforme* |
| 201 | Firmicutes | Erysipelotrichia | Erysipelotrichaceae | *Holdemanella* | *biforme* |
| 202 | Firmicutes | Erysipelotrichia | Erysipelotrichaceae | *Holdemanella* | *biforme* |
| 203 | Firmicutes | Clostridia | Clostridiaceae | *Hungatella* | *effluvii* |
| 204 | Firmicutes | Clostridia | Clostridiaceae | *Hungatella* | *hathewayi* |
| 205 | Firmicutes | Clostridia | Lachnospiraceae | *Lachnoclostridium* | *aerotolerans* |
| 206 | Firmicutes | Clostridia | Lachnospiraceae | *Lachnoclostridium* | *aerotolerans* |
| 207 | Firmicutes | Clostridia | Lachnospiraceae | *Lachnoclostridium* | *aldenense* |
| 208 | Firmicutes | Clostridia | Lachnospiraceae | *Lachnoclostridium* | *asparagiforme* |
| 209 | Firmicutes | Clostridia | Lachnospiraceae | *Lachnoclostridium* | *bolteae* |
| 210 | Firmicutes | Clostridia | Lachnospiraceae | *Lachnoclostridium* | *lavalense* |
| 211 | Firmicutes | Clostridia | Lachnospiraceae | *Lachnoclostridium* | *symbiosum* |
| 212 | Firmicutes | Clostridia | Lachnospiracea | *Lachnospira* | *pectinoschiza* |
| 213 | Firmicutes | Bacilli | Lactobacillaceae | *Lactobacillus* | *coleohominis* |
| 214 | Firmicutes | Bacilli | Lactobacillaceae | *Lactobacillus* | *crispatus* |
| 215 | Firmicutes | Bacilli | Lactobacillaceae | *Lactobacillus* | *crispatus* |
| 216 | Firmicutes | Bacilli | Lactobacillaceae | *Lactobacillus* | *crispatus* |
| 217 | Firmicutes | Bacilli | Lactobacillaceae | *Lactobacillus* | *gasseri* |
| 218 | Firmicutes | Bacilli | Lactobacillaceae | *Lactobacillus* | *jensenii* |
| 219 | Firmicutes | Bacilli | Lactobacillaceae | *Lactobacillus* | *jensenii* |
| 220 | Firmicutes | Bacilli | Lactobacillaceae | *Lactobacillus* | *jensenii* |
| 221 | Firmicutes | Bacilli | Lactobacillaceae | *Lactobacillus* | *jensenii* |
| 222 | Firmicutes | Bacilli | Lactobacillaceae | *Lactobacillus* | *jensenii* |
| 223 | Firmicutes | Bacilli | Lactobacillaceae | *Lactobacillus* | *johnsonii* |
| 224 | Firmicutes | Bacilli | Lactobacillaceae | *Lactobacillus* | *johnsonii* |
| 225 | Firmicutes | Bacilli | Lactobacillaceae | *Lactobacillus* | *johnsonii* |

TABLE 5-continued

Taxonomy Information for All Isolate Samples 1-251

| Isolate Number | Phylum | Class | Family | Genus | Species |
|---|---|---|---|---|---|
| 226 | Firmicutes | Bacilli | Lactobacillaceae | *Lactobacillus* | *johnsonii* |
| 227 | Firmicutes | Clostridia | Clostridiaceae | *Lactonifactor* | *longoviformis* |
| 228 | Firmicutes | Erysipelotrichia | Erysipelotrichaceae | *Longibaculum* | *muris* |
| 229 | Firmicutes | Erysipelotrichia | Erysipelotrichaceae | *Longibaculum* | *muris* |
| 230 | Firmicutes | Erysipelotrichia | Erysipelotrichaceae | *Longibaculum* | *muris* |
| 231 | Firmicutes | Erysipelotrichia | Erysipelotrichaceae | *Longibaculum* | *muris* |
| 232 | Bacteroidetes | Bacteroidia | Muribaculaceae | *Muribaculum* | *intestinale* |
| 233 | Firmicutes | Clostridia | Oscillospiraceae | *Oscillibacter* | *ruminantium* |
| 234 | Firmicutes | Clostridia | Oscillospiraceae | *Oscillibacter* | *ruminantium* |
| 235 | Firmicutes | Clostridia | Oscillospiraceae | *Oscillibacter* | *ruminantium* |
| 236 | Firmicutes | Clostridia | Oscillospiraceae | *Oscillibacter* | *ruminantium* |
| 237 | Bacteroidetes | Bacteroidia | Tannerellaceae | *Parabacteroides* | *distasonis* |
| 238 | Bacteroidetes | Bacteroidia | Tannerellaceae | *Parabacteroides* | *merdae* |
| 239 | Bacteroidetes | Bacteroidia | Tannerellaceae | *Parabacteroides* | *merdae* |
| 240 | Bacteroidetes | Bacteroidia | Tannerellaceae | *Parabacteroides* | *merdae* |
| 241 | Bacteroidetes | Bacteroidia | Tannerellaceae | *Parabacteroides* | *merdae* |
| 242 | Bacteroidetes | Bacteroidia | Tannerellaceae | *Parabacteroides* | *merdae* |
| 243 | Actinobacteria | Actinobacteria | Propionibacteriaceae | *Cutibacterium* | *acnes* |
| 244 | Firmicutes | Clostridia | Lachnospiracea | *Roseburia* | *inulinivorans* |
| 245 | Firmicutes | Clostridia | Lachnospiracea | *Roseburia* | *inulinivorans* |
| 246 | Firmicutes | Clostridia | Lachnospiracea | *Roseburia* | *inulinivorans* |
| 247 | Firmicutes | Clostridia | Ruminococcaceae | *Ruminococcus* | *bromii* |
| 248 | Proteobacteria | Gammaproteobacteria | Enterobacteriaceae | *Shigella* | *flexneri* |
| 249 | Firmicutes | Bacilli | Staphylococcaceae | *Staphylococcus* | *epidermidis* |
| 250 | Firmicutes | Bacilli | Staphylococcaceae | *Staphylococcus* | *warneri* |
| 251 | Proteobacteria | Betaproteobacteria | Sutterellaceae | *Sutterella* | *wadsworthensis* |

Example 5

Characterization of 25 Isolated Bacterial Strains

This example lists examples of isolated strains from Table 3 that have been assigned a strain designation, and which have been characterized for short chain fatty acid (SCFA) production, antibiotic resistance, and/or analyzed by whole genome sequencing.

Table 6 below shows 25 examples of isolate samples, including their genus and species, which were characterized for short chain fatty acid production, antibiotic resistance, and/or by whole genome sequencing.

TABLE 6

Isolate Characterization

| Isolate Number | Genus | Species | Strain Designation | Short Chain Fatty Acid Production Analysis | Antibiotic Resistance Analysis | Whole Genome Seq. |
|---|---|---|---|---|---|---|
| 1 | *Akkermansia* | *muciniphila* | *A. muciniphila* ST7 | | Y | Y |
| 2 | *Akkermansia* | *muciniphila* | *A. muciniphila* ST6 | | | Y |
| 4 | *Akkermansia* | *muciniphila* | *A. muciniphila* ST5 | | | Y |
| 5 | *Akkermansia* | *muciniphila* | *A. muciniphila* ST1 (Am1) | | | Y |
| 11 | *Akkermansia* | *muciniphila* | *A. muciniphila* ST15 (Am5) | Y | | Y |
| 18 | *Akkermansia* | *muciniphila* | *A. muciniphila* ST22 (Am6) | Y | | |
| 28 | *Akkermansia* | *muciniphila* | *A. muciniphila* ST38 (Am4) | | | Y |
| 31 | *Akkermansia* | *muciniphila* | *A. muciniphila* ST43 (Am2) | Y | | Y |
| 33 | *Akkermansia* | *muciniphila* | *A. muciniphila* ST46 (Am3) | Y | | Y |
| 39 | *Akkermansia* | *muciniphila* | *A. muciniphila* ST58 (Am7) | Y | | |
| 111 | *Bifidobacterium* | *adolescentis* | *B. adolescentis* ST15 (Bs10) | | | Y |
| 113 | *Bifidobacterium* | *longum* | *B. longum* ST27 (Bl9) | | | Y |
| 126 | *Blautia* | *producta* | *B. producta* ST4 (Bp8) | | | Y |
| 147 | *Coprococcus* | *comes* | *C. comes* ST3 (Cc11) | | | Y |
| 184 | *Faecalibacterium* | *prausnitzii* | *F. prausnitzii* ST23 (Fp13) | Y | | Y |
| 188 | *Faecalibacterium* | *prausnitzii* | *F. prausnitzii* ST27 (Fp14) | Y | | Y |
| 192 | *Faecalibacterium* | *prausnitzii* | *F. prausnitzii* ST38 (Fp12) | Y | Y | Y |
| 195 | *Faecalibacterium* | *prausnitzii* | *F. prausnitzii* ST58 (Fp15) | Y | | Y |
| 199 | *Faecalibacterium* | *prausnitzii* | *F. prausnitzii* ST74 (Fp16) | Y | | Y |
| 211 | *Lachnoclostridium* | *symbiosum* | *L. symbiosum* ST40 (Bp7) | | | Y |
| 214 | *Lactobacillus* | *crispatus* | *L. crispatus* ST100 (Lj20) | | Y | Y |
| 221 | *Lactobacillus* | *jensenii* | *L. jensenii* ST10 (Lc18) | | | Y |
| 223 | *Lactobacillus* | *johnsonii* | *L. johnsonii* ST8 (Lg19) | | | Y |
| 225 | *Lactobacillus* | *johnsonii* | *L. johnsonii* ST74 (Lj 17) | | | Y |
| 247 | *Ruminococcus* | *bromii* | *R. bromii* ST42 (Rb21) | | | Y |

Example 6

Species Listing for all Isolate Samples (Strains) 1-251

This example lists the isolates described herein by their species, and further provides information regarding their strain, phylum, and genus. As mentioned and described above, the isolates belong to the kingdom of bacteria.

Table 7 below shows that the 251 isolated bacterial colonies belong to 64 different species. *Municiphila* is the most abundant species among all isolated colonies with 36 total isolate numbers. Additional species with isolate numbers >10 are *prausnitzii, fergusonii, vulgatus,* and *fragilis.*

TABLE 7

Species Listing for All Isolate Samples (Strains) 1-251

| Number | Strain | Number of Isolates | Phylum | Genus | Species |
|---|---|---|---|---|---|
| 1 | *Akkermansia muciniphila* | 36 | Verrucomicrobia | *Akkermansia* | *muciniphila* |
| 2 | *Anaerostipes hadrus* | 1 | Firmicutes | *Anaerostipes* | *hadrus* |
| 3 | *Anaerotignum lactatifermentans* | 1 | Firmicutes | *Anaerotignum* | *lactatifermentans* |
| 4 | *Bacteroides caccae* | 2 | Bacteroidetes | *Bacteroides* | *caccae* |
| 5 | *Bacteroides dorei* | 3 | Bacteroidetes | *Bacteroides* | *dorei* |
| 6 | *Bacteroides faecis* | 9 | Bacteroidetes | *Bacteroides* | *faecis* |
| 7 | *Bacteroides finegoldii* | 2 | Bacteroidetes | *Bacteroides* | *finegoldii* |
| 8 | *Bacteroides fragilis* | 14 | Bacteroidetes | *Bacteroides* | *fragilis* |
| 9 | *Bacteroides intestinalis* | 1 | Bacteroidetes | *Bacteroides* | *intestinalis* |
| 10 | *Bacteroides stercoris* | 8 | Bacteroidetes | *Bacteroides* | *stercoris* |
| 11 | *Bacteroides thetaiotaomicron* | 10 | Bacteroidetes | *Bacteroides* | *thetaiotaomicron* |
| 12 | *Bacteroides uniformis* | 3 | Bacteroidetes | *Bacteroides* | *uniformis* |
| 13 | *Bacteroides vulgatus* | 14 | Bacteroidetes | *Bacteroides* | *vulgatus* |
| 14 | *Bacteroides xylanisolvens* | 2 | Bacteroidetes | *Bacteroides* | *xylanisolvens* |
| 15 | *Bifidobacterium faecale* | 2 | Actinobacteria | *Bifidobacterium* | *faecale* |
| 16 | *Bifidobacterium longum* | 1 | Actinobacteria | *Bifidobacterium* | *longum* |
| 17 | *Bifidobacterium stercoris* | 2 | Actinobacteria | *Bifidobacterium* | *stercoris* |
| 18 | *Blautia faecis* | 2 | Firmicutes | *Blautia* | *faecis* |
| 19 | *Blautia gnavus* | 1 | Firmicutes | *Blautia* | *gnavus* |
| 20 | *Blautia luti* | 1 | Firmicutes | *Blautia* | *luti* |
| 21 | *Blautia obeum* | 6 | Firmicutes | *Blautia* | *obeum* |
| 22 | *Blautia producta* | 10 | Firmicutes | *Blautia* | *producta* |
| 23 | *Blautia stercoris* | 2 | Firmicutes | *Blautia* | *stercoris* |
| 24 | *Blautia torques* | 1 | Firmicutes | *Blautia* | *torques* |
| 25 | *Blautia wexlerae* | 7 | Firmicutes | *Blautia* | *wexlerae* |
| 26 | *Collinsella aerofaciens* | 1 | Actinobacteria | *Collinsella* | *aerofaciens* |
| 27 | *Coprococcus comes* | 8 | Firmicutes | *Coprococcus* | *comes* |
| 28 | *Coprococcus eutactus* | 1 | Firmicutes | *Coprococcus* | *eutactus* |
| 29 | *Dorea formicigenerans* | 3 | Firmicutes | *Dorea* | *formicigenerans* |
| 30 | *Dorea longicatena* | 1 | Firmicutes | *Dorea* | *longicatena* |
| 31 | *Eisenbergiella massiliensis* | 1 | Firmicutes | *Eisenbergiella* | *massiliensis* |
| 32 | *Erysipelatoclosfridium ramosum* | 7 | Firmicutes | *Erysipelatoclostridium* | *ramosum* |
| 33 | *Escherichia fergusonii* | 13 | Proteobacteria | *Escherichia* | *fergusonii* |
| 34 | *Eubacterium hallii* | 1 | Firmicutes | *Eubacterium* | *hallii* |
| 35 | *Eubacterium ventriosum* | 1 | Firmicutes | *Eubacterium* | *venfriosum* |
| 36 | *Faecalibacterium prausnitzii* | 16 | Firmicutes | *Faecalibacterium* | *prausnitzii* |
| 37 | *Holdemanella biforme* | 3 | Firmicutes | *Holdemanella* | *biforme* |
| 38 | *Hungatella effluvii* | 1 | Firmicutes | *Hungatella* | *effluvii* |
| 39 | *Hungatella hathewayi* | 1 | Firmicutes | *Hungatella* | *hathewayi* |
| 40 | *Lachnoclostridium aerotolerans* | 2 | Firmicutes | *Lachnoclostridium* | *aerotolerans* |
| 41 | *Lachnoclostridium aldenense* | 1 | Firmicutes | *Lachnoclostridium* | *aldenense* |
| 42 | *Lachnoclostridium asparagiforme* | 1 | Firmicutes | *Lachnoclostridium* | *asparagiforme* |
| 43 | *Lachnoclostridium bolteae* | 1 | Firmicutes | *Lachnoclostridium* | *bolteae* |
| 44 | *Lachnoclostridium lavalense* | 1 | Firmicutes | *Lachnoclostridium* | *lavalense* |
| 45 | *Lachnoclostridium symbiosum* | 1 | Firmicutes | *Lachnoclostridium* | *symbiosum* |

TABLE 7-continued

Species Listing for All Isolate Samples (Strains) 1-251

| Number | Strain | Number of Isolates | Phylum | Genus | Species |
|---|---|---|---|---|---|
| 46 | *Lachnospira pectinoschiza* | 1 | Firmicutes | *Lachnospira* | *pectinoschiza* |
| 47 | *Lactobacillus coleohominis* | 1 | Firmicutes | *Lactobacillus* | *coleohominis* |
| 48 | *Lactobacillus crispatus* | 3 | Firmicutes | *Lactobacillus* | *crispatus* |
| 49 | *Lactobacillus gasseri* | 1 | Firmicutes | *Lactobacillus* | *gasseri* |
| 50 | *Lactobacillus jensenii* | 5 | Firmicutes | *Lactobacillus* | *jensenii* |
| 51 | *Lactobacillus johnsonii* | 4 | Firmicutes | *Lactobacillus* | *johnsonii* |
| 52 | *Lactonifactor longoviformis* | 1 | Firmicutes | *Lactonifactor* | *longoviformis* |
| 53 | *Longibaculum muris* | 4 | Firmicutes | *Longibaculum* | *muris* |
| 54 | *Muribaculum intestinale* | 1 | Bacteroidetes | *Muribaculum* | *intestinale* |
| 55 | *Oscillibacter ruminantium* | 4 | Firmicutes | *Oscillibacter* | *ruminantium* |
| 56 | *Parabacteroides distasonis* | 1 | Bacteroidetes | *Parabacteroides* | *distasonis* |
| 57 | *Parabacteroides merdae* | 5 | Bacteroidetes | *Parabacteroides* | *merdae* |
| 58 | *Propionibacterium acnes* | 1 | Actinobacteria | *Cutibacterium* | *acnes* |
| 59 | *Roseburia inulinivorans* | 3 | Firmicutes | *roseburia* | *inulinivorans* |
| 60 | *Ruminococcus bromii* | 1 | Firmicutes | *Ruminococcus* | *bromii* |
| 61 | *Shigella flexneri* | 1 | Proteobacteria | *Shigella* | *flexneri* |
| 62 | *Staphylococcus epidermidis* | 1 | Firmicutes | *Staphylococcus* | *epidermidis* |
| 63 | *Staphylococcus warneri* | 1 | Firmicutes | *Staphylococcus* | *warneri* |
| 64 | *Sutterella wadsworthensis* | 1 | Proteobacteria | *Sutterella* | *wadsworthensis* |

Example 7

The Microbial Consortium TC3 Reduces Immune Activation in Mouse Model

This example shows that the three-member microbial consortium (e.g., TC3) consisting of *Lactobacillus johnsonii*, *Faecalibacterium prausnitzii*, and *Akkermansia muciniphila* effectively reduced immune activation demonstrated in an allergic sensitization mouse model and as depicted by FIG. 1A-FIG. 1L. The bacterial strains *Lactobacillus johnsonii*, *Faecalibacterium prausnitzii*, and *Akkermansia muciniphila* of the TC3 microbial consortium used for this study were provided by the American Type Culture Collection (ATCC).

In order to investigate the protective effects of the oral TC3 supplementation the cockroach allergen (CRA) murine model was used. C57BL/6 mice (7-8 weeks old) were intratracheally sensitized (Day 1-3) and subsequently challenged for one week with cockroach allergen (CRA and TC3 cohorts only). The mice of the CRA and TC3 cohorts were concurrently supplemented with phosphate buffered saline (PBS, negative vehicle control for CRA cohorts) or with the microbial consortium TC3 (TC3 cohort). In the first week supplementation was performed daily, followed by supplementation twice a week for the remaining two weeks. All supplementations were performed by oral gavage using bacteria resuspended in 100 µl of PBS. At the conclusion of the study, mice were euthanized, and various tissues (lung, spleen, ileum) were collected for ex vivo analyses.

Three independent studies in non-treated (NT) mice, cockroach allergen (CRA) treated mice, and mice treated with CRA and an oral supplementation containing a microbial consortium (TC3) were performed. The plasma concentration values (as ng/mL or pg/mL) of IgE, CRA-specific IgE and histamine were then measured in all cohorts (FIG. 1A-FIG. 1C) using ELISA. Further, the absolute concentration values (in pg/mL, FIG. 1D-FIG. 1E) and the fold change (FIG. 1G-FIG. 1H) of the inflammatory cytokines IL-4 and IL-13 in lung tissue were measured by performing ELISA and qPCR, respectively.

In addition, the abundance of regulatory T cells (FIG. 1I), type 2 helper T cells (FIG. 1J), eosinophils (FIG. 1K), and neutrophils (FIG. 1L) in lung tissues in all three study arms was measured using flow cytometry (fluorescence-assisted cell sorting).

Using standard t-test, significant reductions in circulating IgE and inflammatory cytokines were observed in cohorts treated with the microbial consortium TC3 when compared to cohorts that were exposed to only CRA. Further, oral supplementation with the TC3 consortium increased the amount of anti-inflammatory, regulatory T cells, and reduced the amount of inflammatory type 2 helper T cell populations in lung tissue.

Example 8

The Use of Isolates 1-251 in an Allergic Sensitization Mouse Model

This example shows the use of any of the isolated bacteria strains 1-251 listed in Table 3 for oral supplementation to effectively reduce the immune activation in an allergic sensitization mouse model.

The cockroach allergen (CRA) murine model as described above (EXAMPLE 6) is used to investigate the protective effects of the isolates 1-251 listed in Table 3 in a microbial consortium administered as an oral supplementation.

Figure 2F:
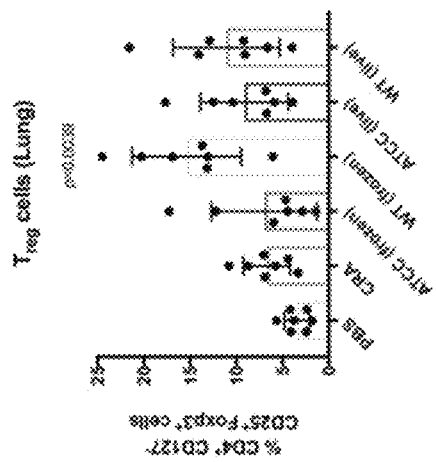
FIG. 2F shows the relative percentage of $T_H2$ cells ($CD3^+$, $CD4^+$, $IL-4^+$, $GATA-3^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2G:
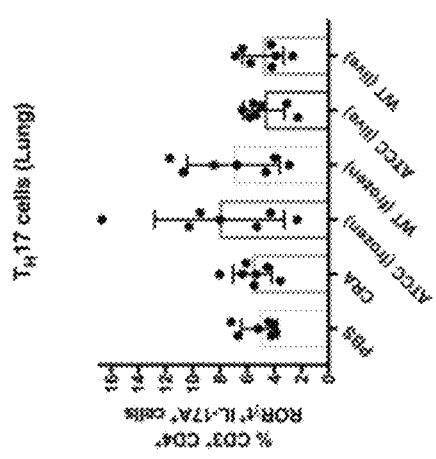
FIG. 2G shows the relative percentage of type 17 T helper ($T_H17$) cells ($CD3^+$, $CD4^+$, $ROR\gamma t^+$, $IL-17A^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2H:
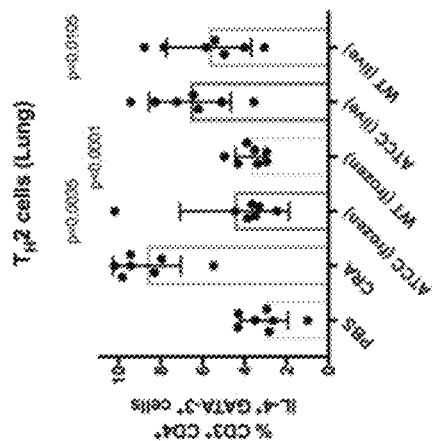
FIG. 2H shows the relative percentage of $T_{reg}$ cells ($CD4^+$, $CD127^-$, $CD25^+$, $Foxp3^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2I:
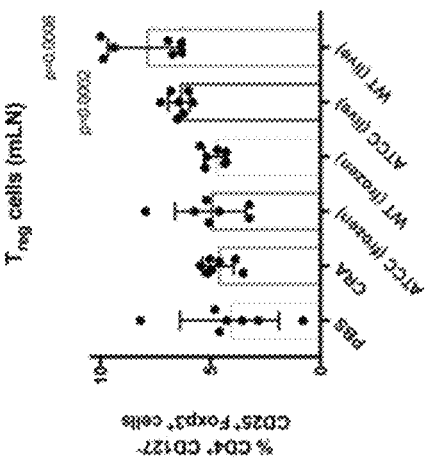
FIG. 2I shows the relative percentage of CRA-specific type $T_2H$ cells ($CD3^+$, $CD4^+$, $IL-4^+$, $GATA-3^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2J:
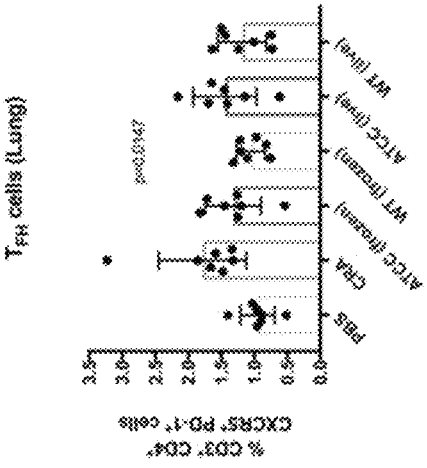
FIG. 2J shows the relative percentage of follicular B helper T ($T_{FH}$) cells ($CD3^+$, $CD4^+$, $CXCR5^+$, $PD-1^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2K:
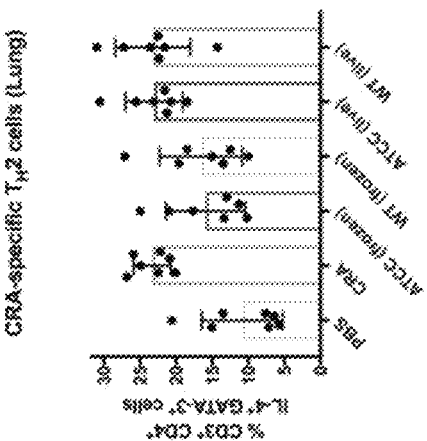
FIG. 2K shows the relative percentage of $T_{reg}$ cells ($CD4^+$, $CD127^-$, $CD25^+$, $Foxp3^+$ cells) in medullary lymph node (mLN) tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2N:
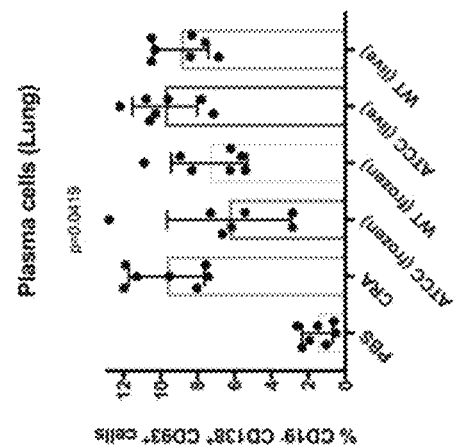
FIG. 2N shows the relative percentage of plasma cells ($CD19^-$, $CD138^+$, $CD93^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2M:
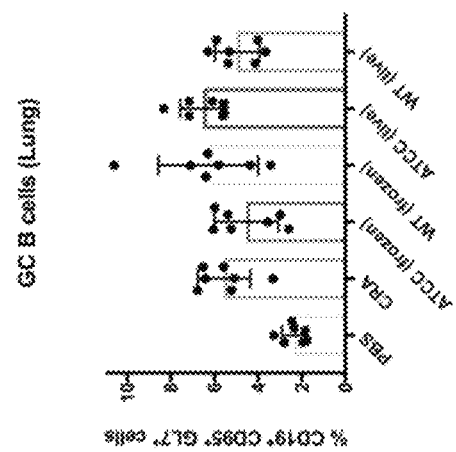
FIG. 2M shows the relative percentage of germinal center (GC) B cells ($CD19^+$, $CD95^+$, $GL7^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2L:
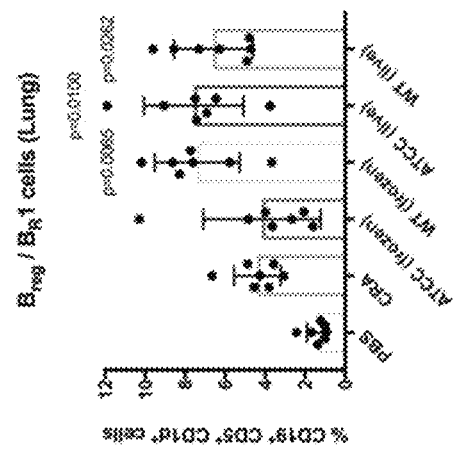
FIG. 2L shows the ratio of B regulatory ($B_{reg}$) cells to B regulatory 1 ($B_R1$) cells ($CD19^+$, $CD5^+$, $CD1d^+$ cells) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2Q:
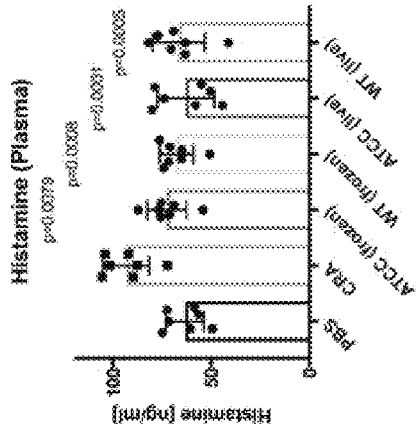
FIG. 2Q shows the histamine concentration values (in ng/mL) in mouse plasma obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2P:
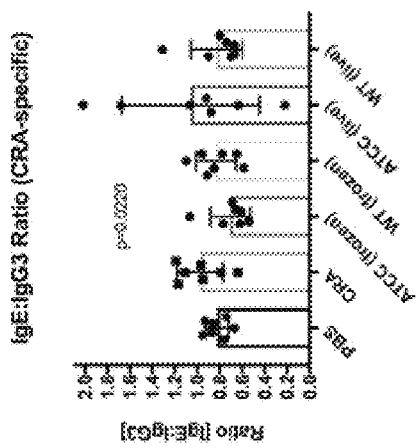
FIG. 2P shows the concentration ratio of CRA-specific IgE to CRA-specific IgG3 in mouse plasma obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2S:
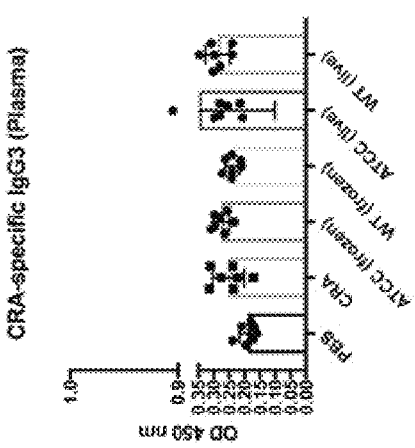
FIG. 2S shows the concentration values of CRA-specific IgG3 (determined by measuring the optical density at 450 nm) in mouse plasma obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2O:
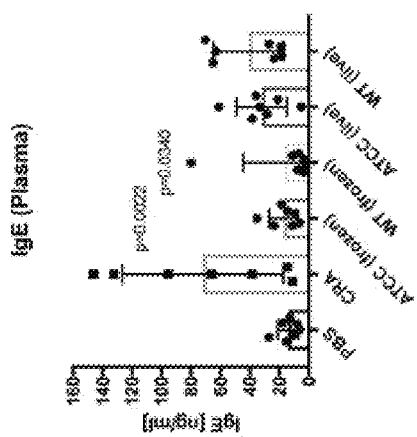
FIG. 2O shows the IgE concentration (in ng/mL) values in mouse plasma obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2R:
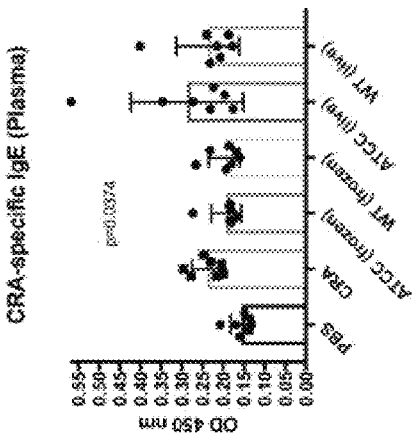
FIG. 2R shows the concentration values of CRA-specific IgE (determined by measuring the optical density at 450 nm) in mouse plasma obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2U:
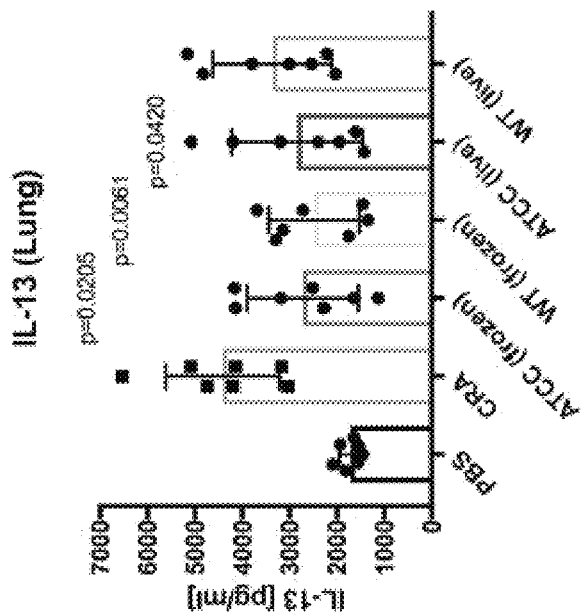
FIG. 2U shows the concentration values of IL-13 (in pg/mL) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.
Figure 2T:
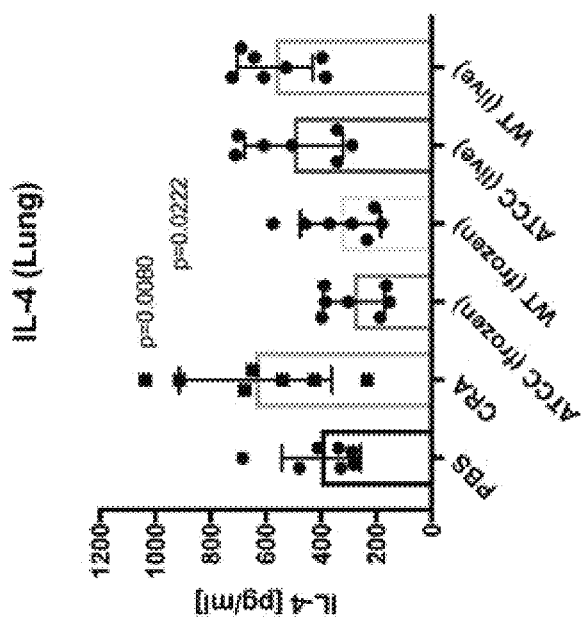
FIG. 2T shows the concentration values of IL-4 (in pg/mL) in lung tissue obtained from six mice cohorts treated with either PBS, CRA, TC3 (ATCC, frozen), TC3 (WT, frozen), TC3 (ATCC, live), or TC3 (WT, live), in accordance with the present disclosure.

The isolated bacterial strains *Lactobacillus johnsonii, Faecalibacterium prausnitzii,* and *Akkermansia muciniphila* from Table 3 (labeled with wild-type, WT, in FIG. 2A-FIG. 2U) show the same reduction in immune activation in the allergic sensitization (CRA) murine model when compared to strains that are provided by the vendor ATCC (FIG. 2A-FIG. 2U).

Example 9

Determination of Strain Properties and Characteristics for *A. muciniphila* ST7 (AM-ST7)

This example shows the determination of strain properties and characteristics for *A. muciniphila* ST7 (or AM-ST7).

*Akkermansia muciniphila* ST7 used in this example was isolated from the stool of a healthy human.

Whole Genome Sequencing and Comparative Analysis

Figure 3:
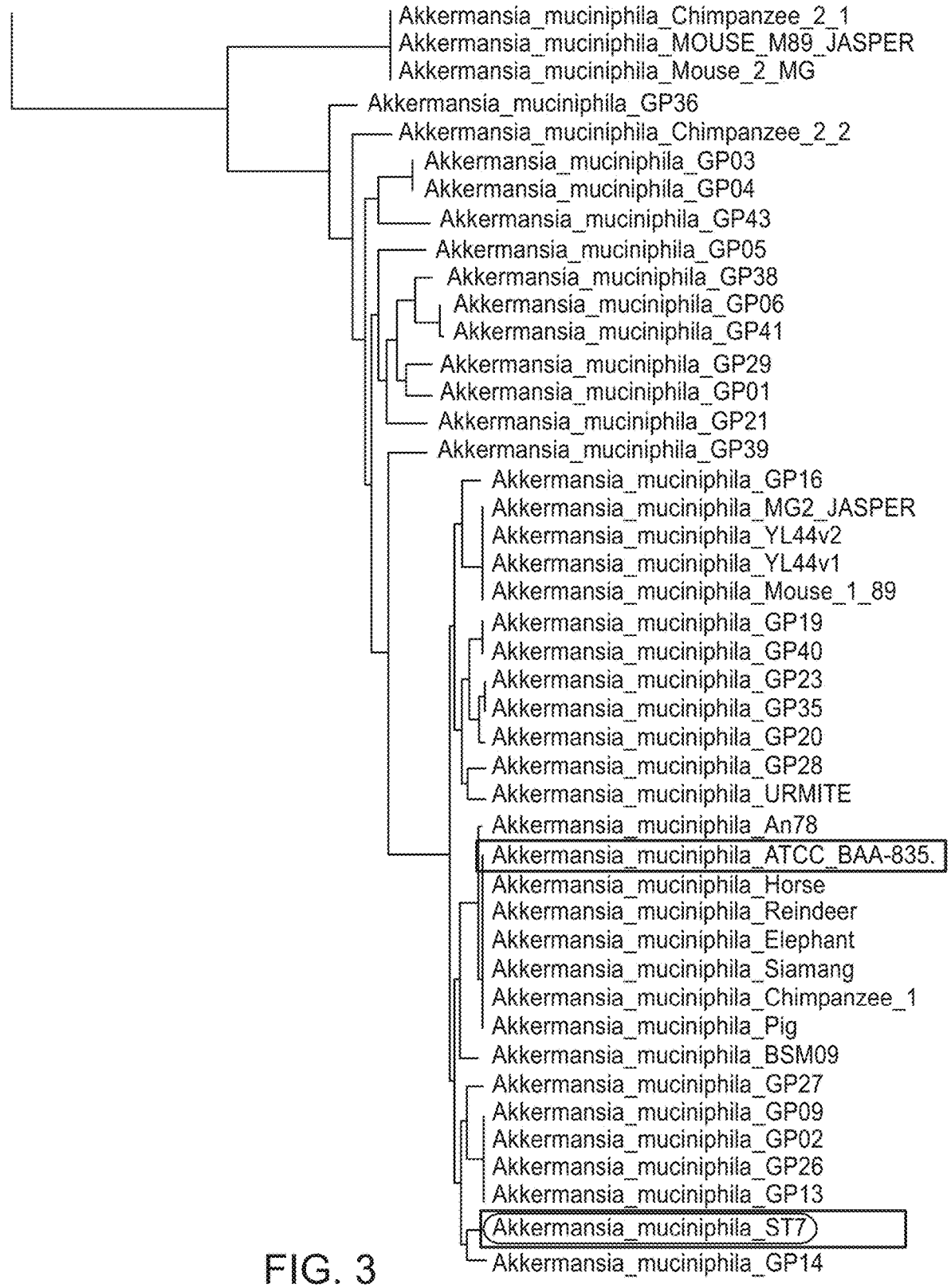
FIG. 3 shows a phylogenetic tree generated using whole genome comparison of *A. muciniphila* strains. AM-ST7 is framed in black.

The genome of *Akkermansia muciniphila* ST7 was sequenced and analyzed. To achieve this, DNA was extracted from AM-ST7 and next-generation DNA sequencing and genome assembly was performed. The AM-ST7 genome library was sequenced using an Ion-Torrent Sequencer, sequence data was assembled using the SPAdes Assembler, and reads were aligned to the reference genome using Harvest. The AM-ST7 genome was sequenced to an average depth of 469× coverage, allowing for high confidence SNP calls for comparison with the type strain *A. muciniphila* BAA-835. To that end, genome scaffolds were multiply-aligned with a fast core-genome multi-aligner (Parsnp v1.2) against the reference of the representative bacterial genome (reference *Akkermansia muciniphila* ATCC BAA-835). The alignment was then used to create phylogenetic trees to compare and identify the closest related strains to the bacterial genome of AM-ST7 using Glade clusters (FIG. 3). As expected due to the conserved nature of *A. muciniphila,* AM-ST7 clusters closely with BAA-835.

Figure 4:
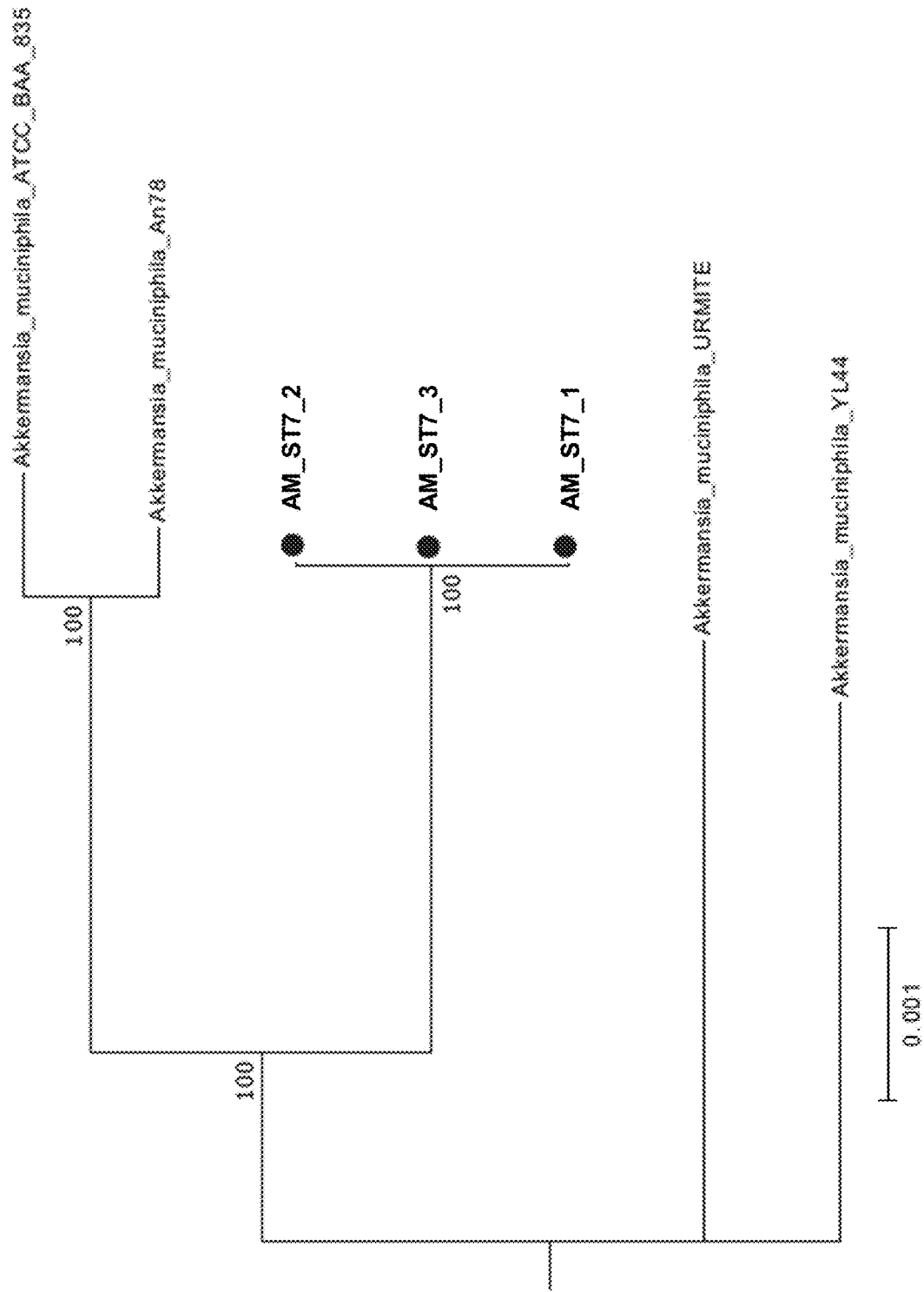
FIG. 4 shows a single nucleotide polymorphism (SNP) tree comparing the three *A. muciniphila* strains AM-ST7_1, AM-ST7_2, and AM-ST7_3 that are genetic variants of AM-ST7 with other *A. muciniphila* strains. The data shows that the three AM-ST7 variants are closely related.
Figure 5:
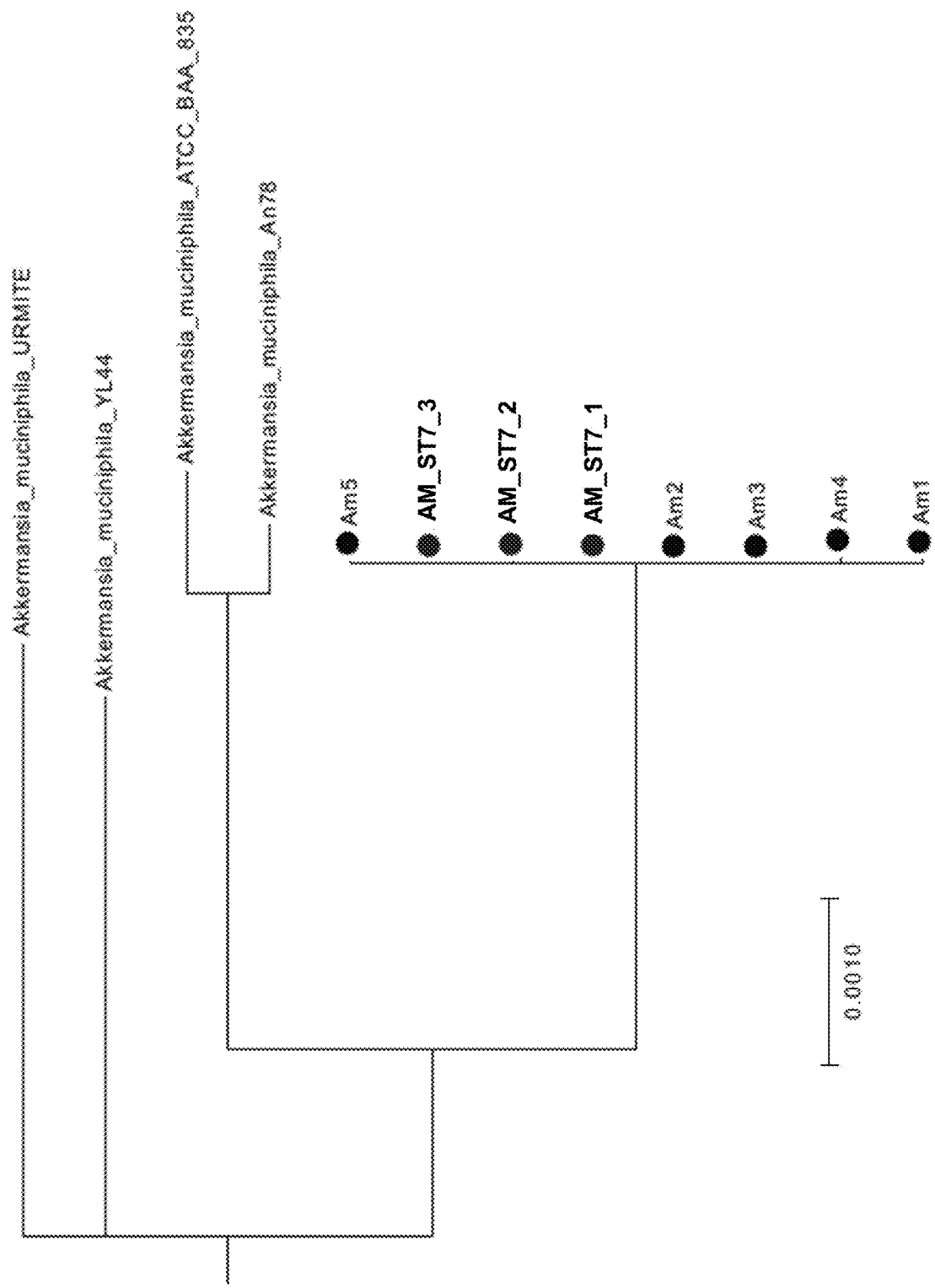
FIG. 5 shows a single nucleotide polymorphism (SNP) tree comparing the three *A. muciniphila* strains AM-ST7_1, AM-ST7_2, and AM-ST7_3 that are genetic variants of AM-ST7 with other *A. muciniphila* strains. The data shows that the three AM-ST7 variants are closely related.
Figure 6:
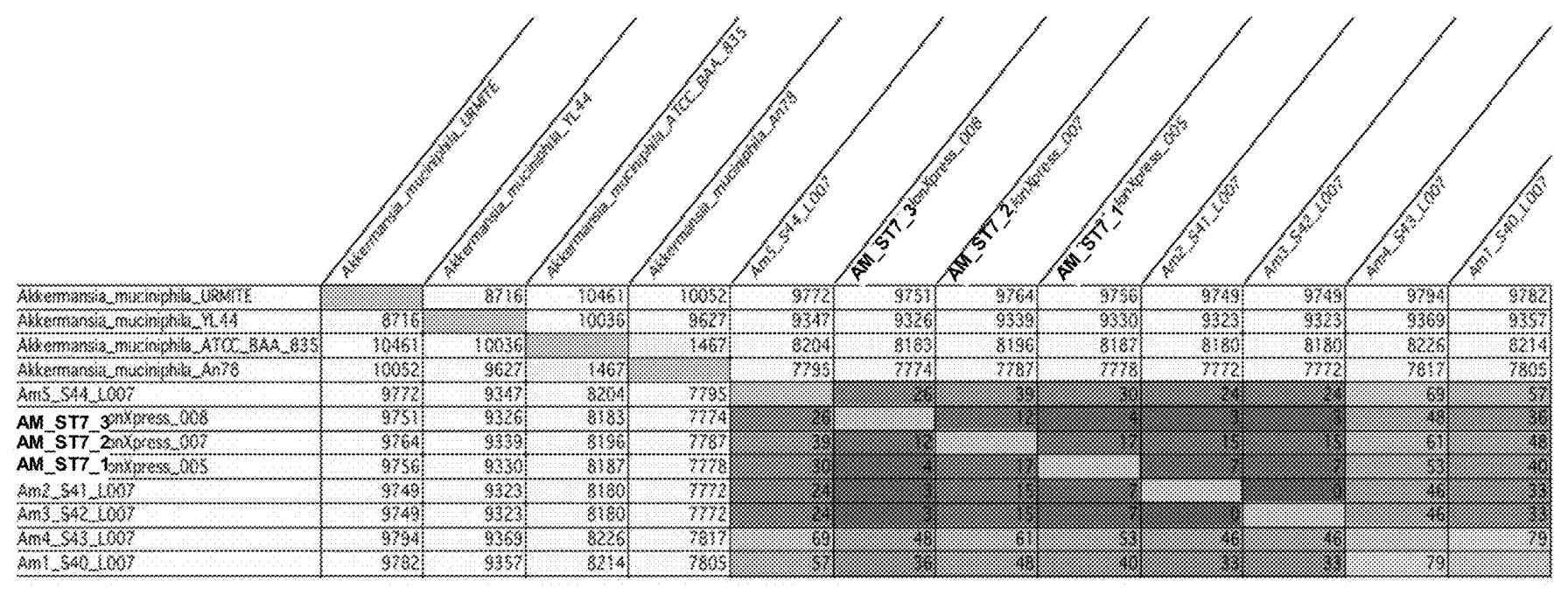

A comparative genomic analysis between AM-ST7 and the type strain *A. muciniphila* BAA-835 was also performed (FIG. 4-FIG. 5). The *A. muciniphila* ST7 genome shares 94% nucleotide identity with *A. muciniphila* BAA-835, with U.S. Pat. Nos. 2,751,252 and 2,664,102 total nucleotides and 55.5% and 55.8% GC content, respectively. The genomic analysis revealed 220 vs. 218 subsystems and 2,815 vs. 2,577 coding regions in *A. muciniphila* ST7 and *A. muciniphila* BAA-835, respectively. Rapid Annotation Subsystem Technology (RAST) was leveraged for predictive functional analysis and gene annotation. This analysis showed that the *A. muciniphila* ST7 genome contains the same major functional categories as *A. muciniphila* BAA-835, with a small number of differing genes. Without being bound by any theory, these difference may correspond with functional (e.g., therapeutic) differences specific to AM-ST7 (FIG. 6).

Antibiotic Resistance, Virulence Factors, and Viruses

In addition to providing high-resolution microbial identification, high performance data mining algorithms and highly curated dynamic comparator databases (e.g., GenBook®) were used to inspect the genome for the presence of virulence, antibiotic resistance, and viral genetic components. GenBook® is a highly curated, proprietary genomic database, comprising 150,000+ bacteria, viruses, fungi and protists genomes and gene sequences. To process the sequence data, a high-performance data mining K-mer based algorithm that rapidly disambiguates hundreds of millions of short reads of a metagenomic sample into the discrete microorganisms engendering the particular sequences was used. The pipeline had two separable comparators. The first consisted of a pre-computation phase and a per-sample computation. The input to the pre-computation phase was a reference microbial database, and its output was a whole genome phylogeny tree, together with sets of fixed length k-mer fingerprints (biomarkers) that were uniquely identified with distinct nodes of the tree. The second per-sample, computational phase searched the hundreds of millions of short sequence reads against the fingerprint sets in minutes. The resulting statistics were analyzed to give fine-grain composition and relative abundance estimates at all nodes of the tree. Enhanced discriminatory power was achieved by running the comparators in sequence. The first comparator found reads in which there is an exact match with an n-mer uniquely identified with a set of reference strains; the second comparator then statistically scored the entire read against the reference to verify that the read was indeed uniquely identified with that set. Similarly, the sample resistome and virulome, the collection of antibiotic resistance and virulence genes in the sample, was identified using the CosmosID, Inc. bioinformatics software package to query the unassembled sequence reads against the CosmosID curated antibiotic resistance and virulence gene databases. This analysis of the AM-ST7 genome found that it does not harbor antibiotic resistance cassettes or pathogenicity islands (virulence factors). Additionally, this analysis found that AM-ST7 does not harbor mammalian viruses.

Antibiotic susceptibility was then determined by standard Kirby-Bauer disk diffusion testing. AM-ST7 was susceptible to the following antibiotics (cm=zone of inhibition): azithromycin (2.5 cm), amoxicillin/clavulanic acid (4 cm), vancomycin (1.5 cm), tetracycline (3 cm), bacitracin (2 cm), and levofloxacin (1.2 cm).

Batch Characterization

All AM-ST7 drug substance batches produced underwent the following characterization to confirm identity.

Figure 7:
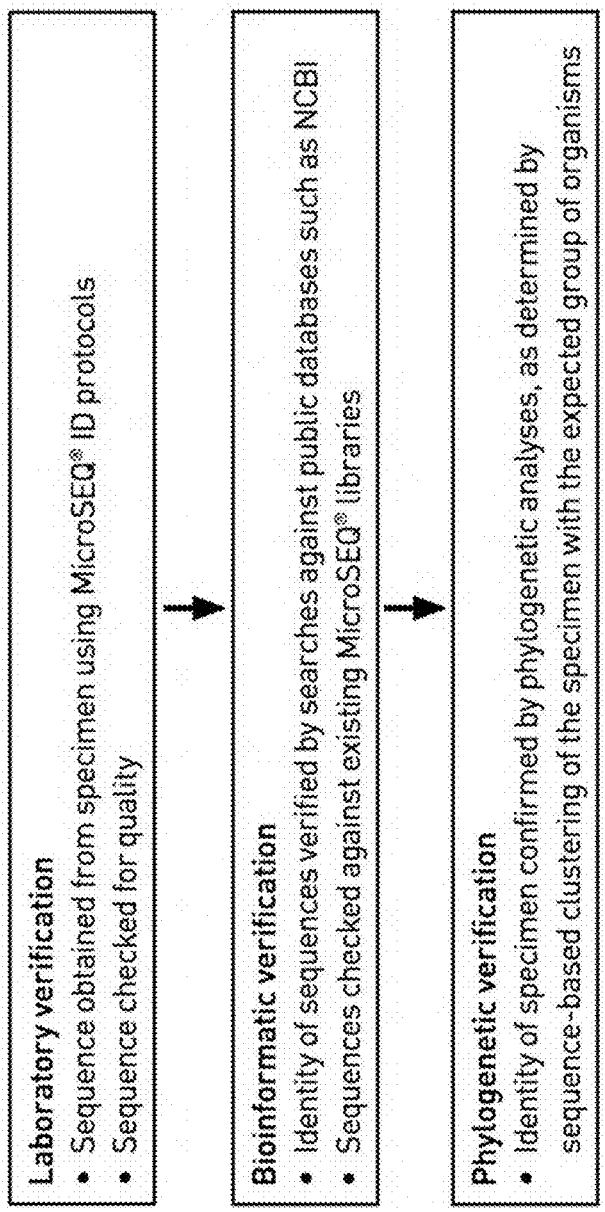
FIG. 7 shows a general outline of a MicroSEQ ID protocol.

Full-Length 16S rRNA Gene Sequencing. The identity of each batch of AM-ST7 cells was confirmed using the genotypic microbial identification service including the MicroSEQ Rapid Microbial Identification System (Applied Biosystems) for genotypic identification of unknown bacterial samples using 16S ribosomal RNA gene sequencing (FIG. 7). The 16S ribosomal RNA gene has been used to identify bacterial isolates, and this method amplifies, sequences, and analyzes the full 1,500 base pairs of the 16S rRNA gene, including several hypervariable regions with unique DNA sequences that can be used to confirm the identification of bacterial species and determine phylogenetic relatedness of bacterial samples. To acquire the species level identification of, the sample was processed according internal standard operating procedures, and the resulting quality control values, bacterial species identification, and percent identity scores.

Macroscopic Colony Morphology Analysis. The identification of the cells in each AM-ST7 drug substance batch was evaluated using standard operating procedures for microbiological evaluations of *A. muciniphila* under cGMP. This procedure includes macroscopic colony morphology analysis of the drug substance. Briefly, a representative aliquot of the drug substance was cultured on mucin agar under anaerobic conditions. The colony morphology of the resulting cells was visually evaluated to determine if the cells fall within known specifications for AM-ST7 colony morphology. The colony morphology characteristics evaluated include colony shape, colony margin (edge), colony elevation, colony size, colony texture, appearance, pigmentation, and optical property.

Microscopic Cell Morphology Analysis. The identification of the cells in each AM-ST7 drug substance batch was evaluated using standard operating procedure for microbiological evaluations of *A. muciniphila* under cGMP. This procedure included microscopic cell morphology analysis of the drug substance. To perform microscopic analysis of the cell morphologies present in each culture, a 10 μL loop of concentrated cell stock was streaked onto a glass slide. The cells were then heat fixed and Gram stained using standard procedures. After Gram staining, a coverslip was added and the slide was viewed using a 1000× oil immersion objective. Slides were inspected to determine if the drug substance cells meet known cell morphology and gram-stain characteristics of AM-ST7.

This data demonstrates various properties of the strain *Akkermansia muciniphila* ST7 (AM-ST7) that can be used in a therapeutic composition as described herein for the prevention and treatment of diseases and conditions (e.g., dysbiosis, inflammation, etc.).

Example 10

Determination of Strain Properties and Characteristics for *Faecalibacterium prausnitzii* ST38 (or FP-ST38)

This example shows the determination of strain properties and characteristics for *Faecalibacterium prausnitzii* ST38 (or FP-ST38). *Faecalibacterium prausnitzii* ST38 (FP-ST38) used in this example was isolated from the stool of a healthy human.

Whole Genome Sequencing and Comparative Analysis

Figure 8:
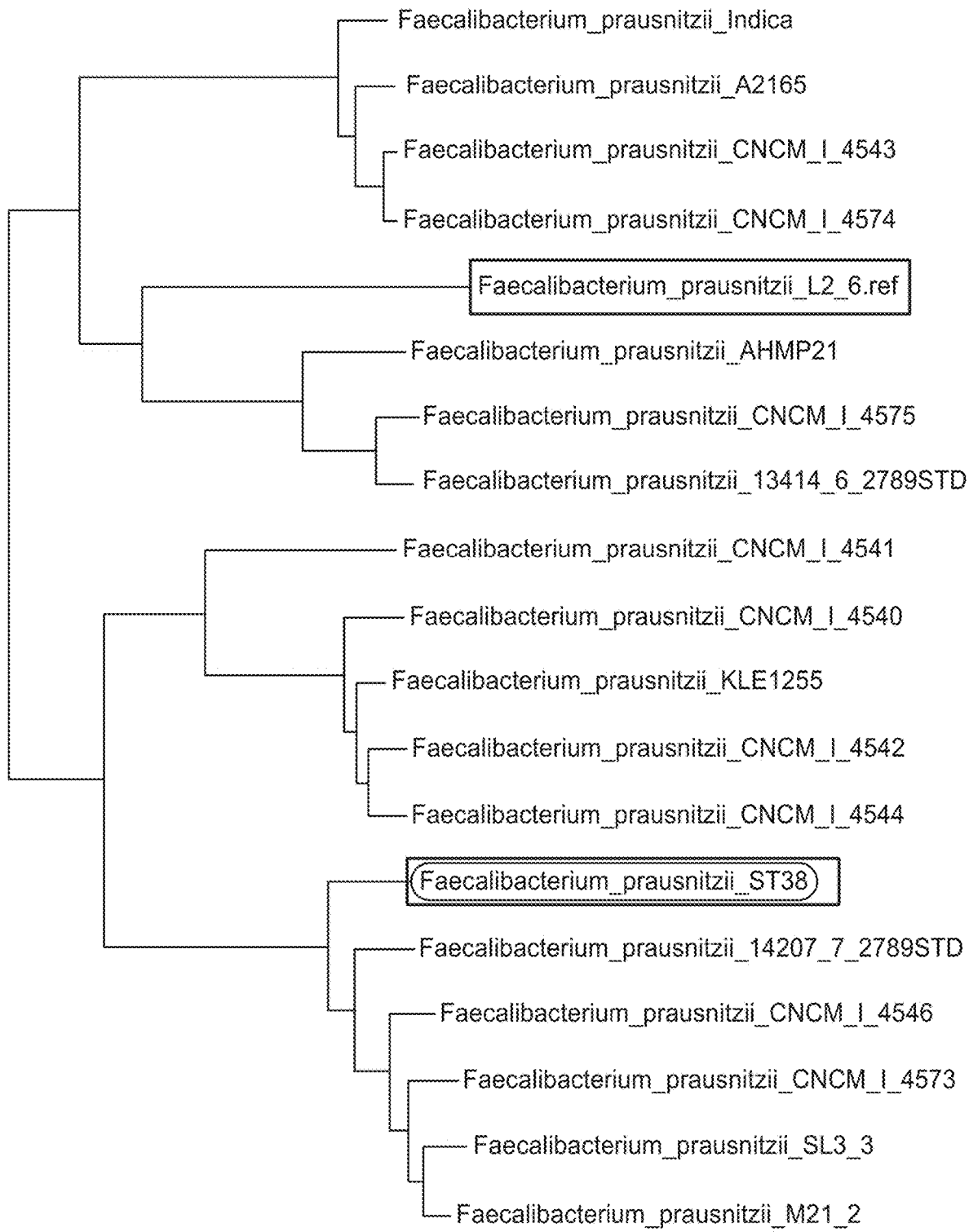
FIG. 8 and FIG. 9 show phylogenetic trees generated using whole genome comparison of *Faecalibacterium prausnitzii* strains. *Faecalibacterium prausnitzii* ST38 is framed in black.
Figure 9:
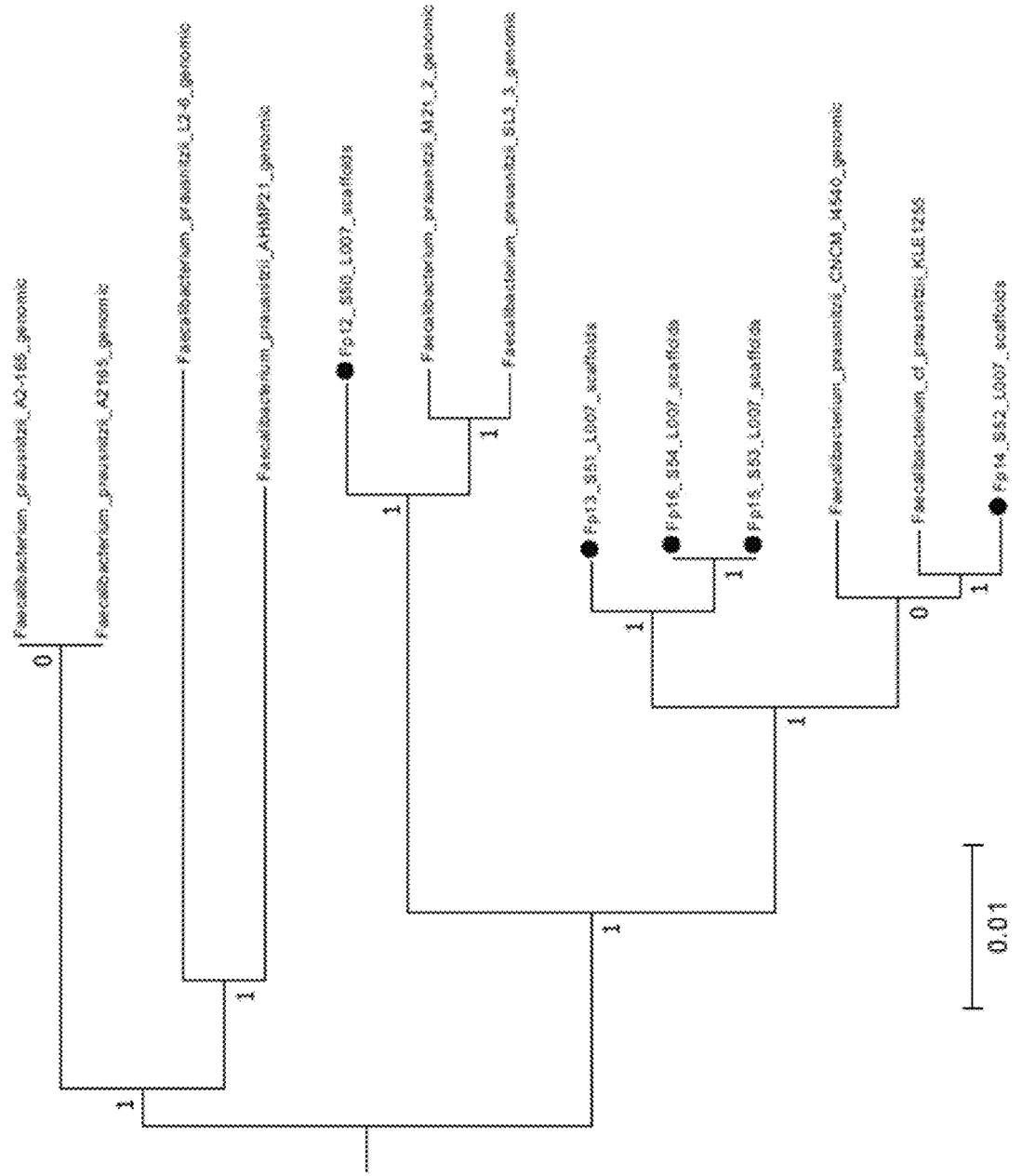

The genome of *Faecalibacterium prausnitzii* ST38 has been sequenced and analyzed as described above in EXAMPLE 8. The multi-alignment was used to create phylogenetic trees to compare and identify the closest related strains to our bacterial genome using Glade clusters. Notably, FP-ST38 clusters in a distinct Glade from that of the reference strain (FIG. 8-FIG. 9).

Antibiotic Resistance, Virulence Factors, and Viruses

The genome of this strain was inspected for the presence of virulence, antibiotic resistance, and viral genetic components as described above in EXAMPLE 8. The analysis of the FP-ST38 genome found that it does not harbor antibiotic resistance cassettes or pathogenicity islands (virulence factors). Additionally, the above analysis found that FP-ST38 does not harbor mammalian viruses.

Antibiotic susceptibility was determined by standard Kirby-Bauer disk diffusion testing. FP-ST38 is susceptible to the following antibiotics (cm=zone of inhibition): amoxicillin/clavulanic acid (2.5 cm), ceftriaxone (2 cm), tetracycline (5 cm), amikacin (2 cm), and bacitracin (3.4 cm).

Batch Characterization

All FP-ST38 drug substance batches produced underwent the same characterization procedure as described above in EXAMPLE 8.

Generally, batch characterization was conducted as described above in EXAMPLE 8.

This data demonstrates various properties of the strain *Faecalibacterium prausnitzii* ST38 (or FP-ST38) that can be used in a therapeutic composition as described herein for the prevention and treatment of diseases and conditions (e.g., dysbiosis, inflammation, etc.).

Example 11

Determination of Strain Properties and Characteristics for *Lactobacillus crispatus* ST100 (LC-ST-100)

This example shows the determination of strain properties and characteristics for *Lactobacillus crispatus* ST100 (LC-ST100). *Lactobacillus crispatus* ST100 (LC-ST100) was isolated from a vaginal swab from a healthy human adult female.

Whole Genome Sequencing and Comparative Analysis

Figure 10:
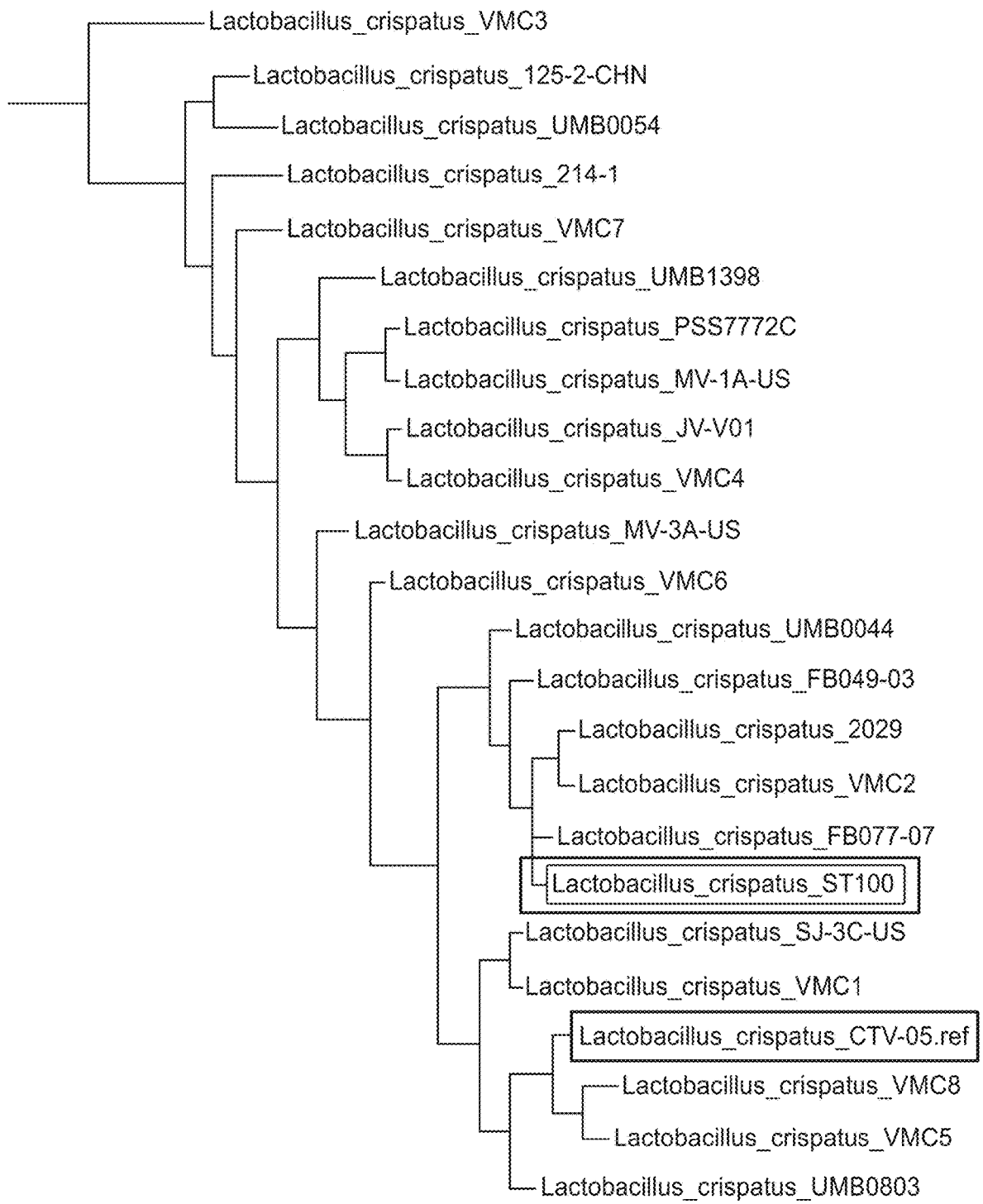
FIG. 10 and FIG. 11 show phylogenetic trees generated using whole genome comparison of *Lactobacillus crispatus* strains. *Lactobacillus crispatus* ST100 (LC-ST100) is framed in black.
Figure 11:
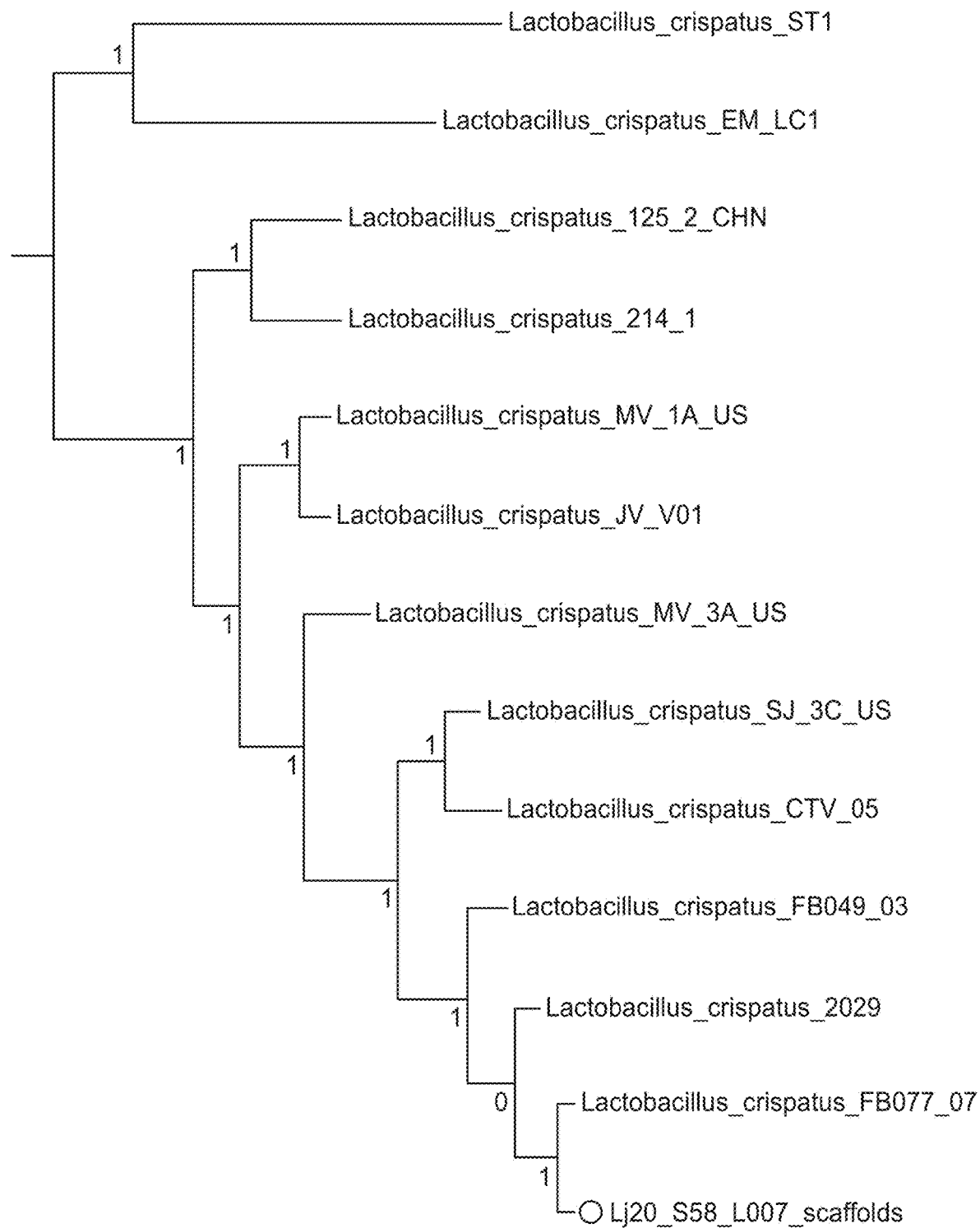

The genome of *Lactobacillus crispatus* ST100 (LC-ST100) has been sequenced and analyzed as described above in EXAMPLE 8. The multi-alignment was used to create phylogenetic trees to compare and identify the closest related strains to our bacterial genome using Glade clusters. Notably, LC-ST100 clusters in a distinct Glade from that of the reference strain (FIG. 10-FIG. 11).

Comparative analysis of the LC-ST100 genome to the related strain *L. crispatus* CTV-05, which has been safely used as a vaginal suppository in human clinical trials, was also performed. The genome of LC-ST100 shares 78% nucleotide identity with CTV-05, revealing similar genome sizes (U.S. Pat. Nos. 2,465,006 and 2,299,477 respectively) and GC content (38.8% and 37.1%, respectively). Comparison of the predictive functional capacity for both strains using RAST—Rapid Annotation Subsystem Technology suggests significant overlap between the two strains with 96-88% overlap at the category, subcategory, and subsystems levels. Interestingly, LC-ST100 harbors additional genes related to nitrogen metabolism and aromatic compound metabolism when compared to strain CTV-05. The sponsor is continuing in their efforts to characterize the unique genomic attributes of LC-ST100, in addition to metabolic and phenotypic differences.

Antibiotic Resistance, Virulence Factors, and Viruses

The genome of this strain was inspected for the presence of virulence, antibiotic resistance, and viral genetic components as described above in EXAMPLE 8. The above analysis of the LC-ST100 genome found that it does not harbor antibiotic resistance cassettes or pathogenicity islands (virulence factors). Additionally, the above analysis found that LC-ST100 does not harbor mammalian viruses.

Antibiotic susceptibility was determined by standard Kirby-Bauer disk diffusion testing. LC-ST100 is susceptible to the following antibiotics (cm=zone of inhibition): azithromycin (3.5 cm), amoxicillin/clavulanic acid (5 cm), clindamycin (4 cm), vancomycin (3.8 cm), ceftriaxone (3.5 cm), tetracycline (4.2 cm), ampicillin (4 cm), bacitracin (2.5 cm).

Batch Characterization

All LC-ST100 drug substance batches produced underwent the same characterization procedure as described above in EXAMPLE 8.

Generally, batch characterization was conducted as described above in EXAMPLE 8.

This data demonstrates various properties of the strain *Lactobacillus crispatus* ST100 (LC-ST100) that can be used in a therapeutic composition as described herein for the prevention and treatment of diseases and conditions (e.g., dysbiosis, inflammation, etc.).

Example 12

Chemical Analysis of the Three Strains *A. muciniphila* ST7, *Faecalibacterium prausnitzii* ST38, and *Lactobacillus crispatus* ST100

This example shows the chemical and metabolic analysis of the strains *A. muciniphila* ST7, *Faecalibacterium prausnitzii* ST38, and *Lactobacillus crispatus* ST100. First, chemical profiles of the spent media and cells of three strains *A. muciniphila* ST7, *Faecalibacterium prausnitzii* ST38, and *Lactobacillus crispatus* ST100 in comparison to their respective naïve media were analyzed. Samples were analyzed using liquid chromatography coupled with mass spectrometry (LC/MS) profiling with a focus on mid-polar compounds. Second, the quantitation of small chain fatty acids (SCFA) in these samples was conducted using gas chromatography coupled with mass spectrometry (GC/MS). Third, the biological activity of these three strains against *Candida* sp. and *Rhodotorula* sp. was tested in-vitro.

Materials and Methods

Generally, all samples were provided in lyophilized from. Subsets of each sample were suspended in solvent for analysis by LC/MS and GC/MS. Following these analyses, further subsets of each sample were extracted and fractionated (to enrich the medium polar range). Fractions were analyzed by LC/MS. Cell extracts were analyzed in a bioassay against *Candida* sp. and *Rhodotorula* sp. in a disk diffusion assay at 3 concentrations.

Table 8 below described the samples tested in this example.

TABLE 8

Sample Descriptions

| Sample | Description |
|---|---|
| 1 | *Lactobacillus crispatus* lyophilized cells |
| 2 | *Lactobacillus crispatus* lyophilized spent media |
| 3 | *Lactobacillus crispatus* lyophilized naïve media |
| 4 | *Akkermansia muciniphila* lyophilized cells |
| 5 | *Akkermansia muciniphila* lyophilized spent media |
| 6 | *Akkermansia muciniphila* lyophilized naïve media |
| 7 | *Faecalibacterium prausnitzii* lyophilized cells |
| 8 | *Faecalibacterium prausnitzii* lyophilized spent media |
| 9 | *Faecalibacterium prausnitzii* lyophilized naïve media |

Analytical Preparation and Direct Profiling. Samples for LC/MS profiling were generated by transferring 30 mg of the sample material into a 4 mL glass vial followed by addition of either 500 µL Methanol and 500 µL water or 1 mL of DMSO. The samples were then sonicated for up to 10 min and non-dissolved particles were removed be centrifugation followed by filtration.

Preparative Cell Extraction. Lyophilized cells were extracted prior to fractionation/bio assay to remove cell wall debris. The cells were adjusted to a final concentration of 50 mg/mL (Table 9) and sonicated for 15 min followed by vortexing for 2 min and a second sonication step of 15 min. Afterwards, 10 mL of the suspension were transferred to another vial an centrifuged at 10,000 RCF for 5 min. The supernatant was transferred to a new vial.

TABLE 9

Sample Amounts and Extraction Volumes

| Sample | Amount [mg] | 90% Methanol (aq.) [mL] | Final concentration [mg/mL] |
|---|---|---|---|
| 1 | 584 | 11.67 | 50 |
| 4 | 631 | 12.62 | 50 |
| 7 | 610 | 12.2 | 50 |

Disk diffusion test. Disk diffusion tests for antimicrobial activity were prepared according to DIN 58940-3 (DIN-Taschenbuch 222, 5. Edition) using the strains 00549fBCD000864 (*Rho. glutinis*, test strain #1) DSM 70821 and 00539fDSM011226 (*Ca. glabrata*, test strain #2) DSM 11226. For the in vitro testing of the biological activity for the three therapeutic strains *A. muciniphila* ST7, *Faecalibacterium prausnitzii* ST38, and *Lactobacillus crispatus* ST100, 73.4 mg Cycloheximid were dissolved in 7.34 mL 90% MeOH (aq.) solution resulting in a 10 mg/mL solution. 3 pieces of aluminum foil (10×10 cm) were sterilized using UV light for 30 min. Four sterile filterdiscs were placed on each piece of foil. The dilutions 1-3 (15 µL) were pipetted to the first three filterdisc. The fourth filterdisc was prepared with 10 µl of cycloheximid solution. All spots were allowed to dry completely.

The test strains were diluted to 1.000.000 cfu/mL using saline solution. Agar plates were prepared using modified YNB-Agar. The test strain solution (400 µL) was pipetted to the center of the plate and distributed homogenously using a sterile Grigalski-spatula. After approximately 5 min the filterdiscs were placed on the plate which was closed with parafilm directly and incubated for 24 h at 25° C. After 24 h the zone of inhibition was measured and recorded in Table 10 below.

TABLE 10

Disk Diffusion Assay Results

| Test strain | Sample (see Table 6) | V [µL]/ disc | µg/disc or µg extracted/ disc | Diameter inhibition zone* [mm] Sample | Diameter inhibition zone* [mm] Pos. Control** |
|---|---|---|---|---|---|
| 2 | 2 | 30 | 1500 | 6 | 11 |
| 2 | 5 | 30 | 1500 | 6 | 11 |
| 2 | 8 | 30 | 1500 | 6 | 11 |
| 2 | 9 | 30 | 1500 | 6 | 10 |
| 2 | 3 | 30 | 1500 | 6 | 10 |
| 2 | 6 | 30 | 1500 | 6 | 10 |
| 2 | 1 | 30 | *3000* | 6 | 9 |
| 2 | 4 | 30 | *3000* | 6 | 9 |
| 2 | 7 | 30 | *3000* | 6 | 9 |
| 2 | 2 | 10 | 500 | 6 | 11 |
| 2 | 5 | 10 | 500 | 6 | 11 |
| 2 | 8 | 10 | 500 | 6 | 11 |
| 2 | 9 | 10 | 500 | 6 | 10 |
| 2 | 3 | 10 | 500 | 6 | 10 |
| 2 | 6 | 10 | 500 | 6 | 10 |
| 2 | 1 | 10 | *1000* | 6 | 9 |
| 2 | 4 | 10 | *1000* | 6 | 9 |
| 2 | 7 | 10 | *1000* | 6 | 9 |
| 1 | 2 | 30 | 1500 | 6 | 14 |
| 1 | 5 | 30 | 1500 | 6 | 14 |
| 1 | 8 | 30 | 1500 | 6 | 14 |
| 1 | 9 | 30 | 1500 | 6 | 13 |
| 1 | 3 | 30 | 1500 | 6 | 13 |
| 1 | 6 | 30 | 1500 | 6 | 13 |
| 1 | 1 | 30 | *3000* | 6 | 13 |
| 1 | 4 | 30 | *3000* | 6 | 13 |
| 1 | 7 | 30 | *3000* | 6 | 13 |

TABLE 10-continued

Disk Diffusion Assay Results

| Test strain | Sample (see Table 6) | V [μL]/ disc | μg/disc or μg extracted/ disc | Diameter inhibition zone* [mm] Sample | Diameter inhibition zone* [mm] Pos. Control** |
|---|---|---|---|---|---|
| 1 | 2 | 10 | 500 | 6 | 14 |
| 1 | 5 | 10 | 500 | 6 | 14 |
| 1 | 8 | 10 | 500 | 6 | 14 |
| 1 | 9 | 10 | 500 | 6 | 13 |
| 1 | 3 | 10 | 500 | 6 | 13 |
| 1 | 6 | 10 | 500 | 6 | 13 |
| 1 | 1 | 10 | *1000* | 6 | 13 |
| 1 | 4 | 10 | *1000* | 6 | 13 |
| 1 | 7 | 10 | *1000* | 6 | 13 |

*Disk diameter = 6 mm
**Positive control = 2 μg Cycloheximide/disc

Sample fractionation. Naïve and spent media samples were fractionated directly using 2 g of sample. Approximately 500 mg of lyophilized cells were extracted as described herein and fractionated. The material was adsorbed on celite (14 g) and fractionated using a Polygoprep 60 μm 125×15 mm column, generating 18 fractions.

Quantitation of SCFAs. Samples were dissolved in 1 mL of ultrapure water, followed by centrifugation. The supernatants were collected and transferred to a GC vial. For quality control, a mixed pooled sample (QC sample) was created by taking a small aliquot from each sample. This sample was analyzed at regular intervals throughout the sequence. Matrix effects were tested for quantified compounds by spiking the QC sample in a minimum of two levels. The small chain fatty acids (SCFAs) method is a GC-MS method specially designed for short-chain fatty acids using a high polarity column. Samples were acidified with hydrochloric acid.

Tables 11-13 below show fractions generated from the three strains *A. muciniphila* ST7, *Faecalibacterium prausnitzii* ST38, and *Lactobacillus crispatus* ST100, respectively.

TABLE 11

Fractions Generated from *Lactobacillus crispatus*

| spent medium | amount [mg] | naïve medium | amount [mg] | cell extract | amount [mg] |
|---|---|---|---|---|---|
| C-3030-A | 925.0 | C-3031-A | 1789.5 | C-3043-A | 25.4 |
| C-3030-B | 1095.6 | C-3031-B | 603.4 | C-3043-B | 12.0 |
| C-3030-C | 81.5 | C-3031-C | 61.4 | C-3043-C | 6.3 |
| C-3030-D | 38.2 | C-3031-D | 35.5 | C-3043-D | 4.3 |
| C-3030-E | 83.9 | C-3031-E | 122.6 | C-3043-E | 8.1 |
| C-3030-F | 66.8 | C-3031-F | 38.3 | C-3043-F | 3.6 |
| C-3030-G | 19.9 | C-3031-G | 14.2 | C-3043-G | 3.5 |
| C-3030-H | 10.3 | C-3031-H | 8.1 | C-3043-H | 5.2 |
| C-3030-I | 6.0 | C-3031-I | 4.4 | C-3043-I | 3.9 |
| C-3030-K | 4.7 | C-3031-K | 3.1 | C-3043-K | 3.3 |
| C-3030-L | 5.7 | C-3031-L | 2.5 | C-3043-L | 5.8 |
| C-3030-M | 12.6 | C-3031-M | 1.9 | C-3043-M | 5.1 |
| C-3030-N | 6.7 | C-3031-N | 1.7 | C-3043-N | 1.4 |
| C-3030-O | 4.4 | C-3031-O | 1.5 | C-3043-O | 2.5 |
| C-3030-P | 2.6 | C-3031-P | 1.0 | C-3043-P | 1.7 |
| C-3030-R | 1.2 | C-3031-R | 1.2 | C-3043-R | 3.8 |
| C-3030-S | 0.0 | C-3031-S | 1.0 | C-3043-S | 0.9 |
| C-3030-T | 0.4 | C-3031-T | 0.2 | C-3043-T | 2.4 |

TABLE 12

Fractions Generated from *Akkermansia muciniphila*

| spent medium | amount [mg] | naïve medium | amount [mg] | cell extract | amount [mg] |
|---|---|---|---|---|---|
| C-3032-A | 1060.7 | C-3033-A | 1390.8 | C-3044-A | 27.0 |
| C-3032-B | 375.1 | C-3033-B | 685.4 | C-3044-B | 8.4 |
| C-3032-C | 58.8 | C-3033-C | 82.3 | C-3044-C | 3.9 |
| C-3032-D | 29.2 | C-3033-D | 43.2 | C-3044-D | 3.1 |
| C-3032-E | 126.2 | C-3033-E | 152.2 | C-3044-E | 5.8 |
| C-3032-F | 48.6 | C-3033-F | 33.4 | C-3044-F | 2.2 |
| C-3032-G | 23.8 | C-3033-G | 10.5 | C-3044-G | 3.1 |
| C-3032-H | 5.9 | C-3033-H | 7.9 | C-3044-H | 1.8 |
| C-3032-I | 2.3 | C-3033-I | 2.8 | C-3044-I | 1.9 |
| C-3032-K | 1.6 | C-3033-K | 2.0 | C-3044-K | 2.6 |
| C-3032-L | 1.0 | C-3033-L | 1.8 | C-3044-L | 1.9 |
| C-3032-M | 1.5 | C-3033-M | 1.7 | C-3044-M | 2.1 |
| C-3032-N | 0.7 | C-3033-N | 1.6 | C-3044-N | 2.3 |
| C-3032-O | 0.5 | C-3033-O | 1.4 | C-3044-O | 3.1 |
| C-3032-P | 0.4 | C-3033-P | 1.0 | C-3044-P | 3.2 |
| C-3032-R | 0.5 | C-3033-R | 0.7 | C-3044-R | 3.1 |
| C-3032-S | 0.4 | C-3033-S | 0.8 | C-3044-S | 1.4 |
| C-3032-T | 0.2 | C-3033-T | 0.3 | C-3044-T | 0.5 |

TABLE 13

Fractions Generated from *Faecalibacterium prausnitzii*

| spent medium | amount [mg] | naïve medium | amount [mg] | cell extract | amount [mg] |
|---|---|---|---|---|---|
| C-3034-A | 1316.8 | C-3035-A | 1529.2 | C-3045-A | 17.2 |
| C-3034-B | 830.2 | C-3035-B | 579.1 | C-3045-B | 10.6 |
| C-3034-C | 90.0 | C-3035-C | 81.8 | C-3045-C | 3.2 |
| C-3034-D | 48.9 | C-3035-D | 52.5 | C-3045-D | 4.6 |
| C-3034-E | 169.8 | C-3035-E | 175.3 | C-3045-E | 3.8 |
| C-3034-F | 51.4 | C-3035-F | 35.7 | C-3045-F | 2.5 |
| C-3034-G | 14.5 | C-3035-G | 11.7 | C-3045-G | 0.9 |
| C-3034-H | 7.3 | C-3035-H | 5.9 | C-3045-H | 1.3 |
| C-3034-I | 3.4 | C-3035-I | 1.8 | C-3045-I | 1.5 |
| C-3034-K | 2.6 | C-3035-K | 0.8 | C-3045-K | 1.0 |
| C-3034-L | 2.4 | C-3035-L | 0.7 | C-3045-L | 1.6 |
| C-3034-M | 2.2 | C-3035-M | 2.0 | C-3045-M | 3.8 |
| C-3034-N | 1.5 | C-3035-N | 1.9 | C-3045-N | 3.5 |
| C-3034-O | 1.9 | C-3035-O | 1.4 | C-3045-O | 6.1 |
| C-3034-P | 0.3 | C-3035-P | 1.2 | C-3045-P | 1.8 |
| C-3034-R | 1.3 | C-3035-R | 1.0 | C-3045-R | 0.5 |
| C-3034-S | 0.4 | C-3035-S | 0.8 | C-3045-S | 0.9 |
| C-3034-T | 0.4 | C-3035-T | 0.6 | C-3045-T | 0.6 |

LC/MS Analysis Results

Figure 12:
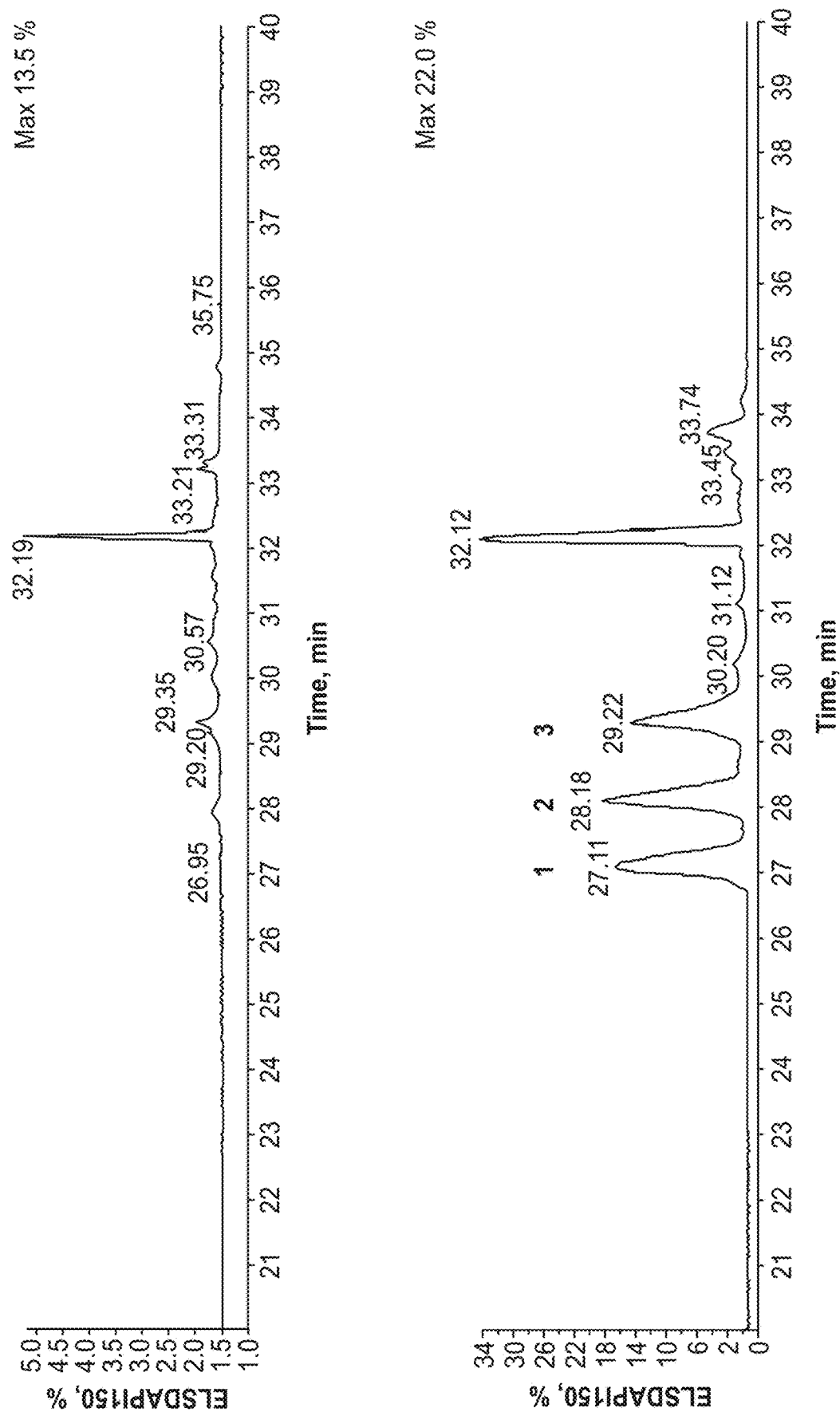
FIG. 12 shows a snapshot of the ELSD chromatogram of fraction M of *A. muciniphila* naïve medium (top) and *A. muciniphila* cell extract (bottom), with signal peaks corresponding to compounds 1-3 (which chemical structures are shown in FIG. 13).

LC/MS profiling of the analytical preparations of 9 samples showed no significant signals in the medium polar range (approx. 5-30 min.). To further address this finding, samples were subjected to a preparative extraction and RP-HPLC fractionation to see if any enrichment of the medium polar range may be achieved (Tables 11-13). After subtracting the profile of the naïve medium, one fraction, fraction C-3044M, derived from *Akkermansia muciniphila* cells, showed significant peaks of interest (FIG. 12).

The MS data suggested these compounds to be phosphatidylcholine precursors and/or phosphatidylcholine-like compounds (compounds 1-3) with chemical structures shown in FIG. 13. This data confirms that *Akkermansia muciniphila* produces significant quantities of anti-inflammatory compounds, including phosphatidylcholines and derivatives thereof, resulting, at least in part, in the therapeutic properties of *Akkermansia muciniphila*-containing microbial consortia described herein.

GC/MS Analysis Results

GC/MS analysis of the samples screened for ten SCFAs as described below in Table 14. Acetic acid was detected in all samples. Formic acid was detected in *A. muciniphila* and *F. prausnitzii*. Propanoic acid was detected in *F. prausnitzii*, and 2-methyl-propanoic acid was detected in *L. crispatus*. Butanoic acid was detected in the cells and spent media of *F. prausnitzii* (and not the naïve media) confirming that *F. prausnitzii* produces butyrate.

pounds with biological activity, including anti-inflammatory activity, and thus may, at least in part, explain the therapeutic properties of the microbial consortia of the present disclosure.

TABLE 14

Quantification of SCFAs*

|  | Acetic acid | Formic acid | Propanoic acid | 2-methyl-propanoic acid | Butanoic acid | 3-methyl-butanoic acid | Pentanoic acid | 4-methyl-pentanoic acid | Hexanoic acid | Heptanoic acid |
|---|---|---|---|---|---|---|---|---|---|---|
| Descriptive power | 38.0 | 52.4 | 52.6 | 3.3 | 30.5 | ND | ND | ND | ND | ND |
| Rel. Precision (%) | 2 | 4 | 2 | 8 | 6 | ND | ND | ND | ND | ND |
| Absolute Precision | 8 | 4 | 0.5 | 0.1 | 4 | ND | ND | ND | ND | ND |
| LOD | 4 | 5 | 1.3 | 0.4 | 3 | 0.3 | 0.4 | 0.5 | 0.3 | 0.6 |
| Sample | µmol/g | µmol/g | µmol/g | µmol/g | µmol/g | µmol/g | µmol/g | µmol/g | µmol/g | µmol/g |
| 1 | 125 | <LOD | <LOD | <LOD | <LOD | <LOD | <LOD | <LOD | <LOD | <LOD |
| 1 | 113 | <LOD | <LOD | <LOD | <LOD | <LOD | <LOD | <LOD | <LOD | <LOD |
| 2 | 523 | <LOD | <LOD | 0.7 | <LOD | <LOD | <LOD | <LOD | <LOD | <LOD |
| 2 | 499 | <LOD | 1.4 | 0.5 | 4.3 | <LOD | <LOD | <LOD | <LOD | <LOD |
| 3 | 1029 | 6 | <LOD | 1.5 | <LOD | <LOD | <LOD | <LOD | <LOD | <LOD |
| 4 | 26 | <LOD | <LOD | <LOD | <LOD | <LOD | <LOD | <LOD | <LOD | <LOD |
| 4 | 27 | <LOD | <LOD | <LOD | <LOD | <LOD | <LOD | <LOD | <LOD | <LOD |
| 5 | 181 | 10 | <LOD | <LOD | <LOD | <LOD | <LOD | <LOD | <LOD | <LOD |
| 5 | 174 | 10 | <LOD | <LOD | <LOD | <LOD | <LOD | <LOD | <LOD | <LOD |
| 6 | 57 | 7 | <LOD | 0.5 | <LOD | <LOD | <LOD | <LOD | <LOD | <LOD |
| 7 | 98 | 52 | 13 | <LOD | 100 | <LOD | <LOD | <LOD | <LOD | <LOD |
| 7 | 86 | 36 | 9.4 | <LOD | 68 | <LOD | <LOD | <LOD | <LOD | <LOD |
| 8 | 678 | 571 | 76 | <LOD | 369 | <LOD | <LOD | <LOD | <LOD | <LOD |
| 8 | 685 | 537 | 75 | 0.5 | 355 | <LOD | <LOD | <LOD | <LOD | <LOD |
| 9 | 803 | 13 | 45 | 0.8 | <LOD | <LOD | <LOD | <LOD | <LOD | <LOD |

* Cells and spent media were analyzed in duplicate and compared to the naïve medium.
Naïve media is denoted by grey highlighting.
The Descriptive Power is calculated as the ratio between the standard deviation within experimental samples and the standard deviation within the QC samples.
Variables with a ratio higher than 2.5 are most likely to describe variation related to the experimental design.
<LOD denotes that measurement was below limit of detection.

Antimicrobial Testing Results

The screening of naive media, spent media, and cell extracts of all three strains against *Ca. glabrata* and *Rho. glutinis* resulted in no observed anti-microbial activity against these strains (Table A2).

The data of this study demonstrate that the herein analyzed samples obtained from bacteria of microbial consortia primarily comprised of compounds in the polar region. Fractionation of the samples allowed for an analysis of the medium polarity range independently. The data further show that three phosphatidylcholine derivatives (compounds 1-3, FIG. 13) were identified as products of *Akkermansia muciniphila*. An additional compound with a molecular weight of 386 Da was also detected. Analysis of the small chin fatty acid (SCFA) content confirmed that *F. prausnitzii* produces butanoic acid, while acetic acid, formic acid, propanoic acid, and 2-methyl-propanoic acid, may be detected differentially across the three strains. Additionally, a test for antimicrobial activity against *Candida* sp. and *Rhodotorula* sp. was negative.

Particularly the production of the three phosphatidylcholine derivatives 1-3 (FIG. 13) is an indication that *Akkermansia muciniphila* (and other strains of the consortia described herein) produces significant amounts of com- Example 13

Analysis of Antibiotic Resistance of *Akkermansia muciniphila* and *Faecalibacterium prausnitzii* Strains This example shows the analysis of antibiotic resistance of the strains *A. muciniphila* ST7, *F. prausnitzii* ST38, or *L. crispatus* ST100. Antibiotic resistance in this example was determined using the broth solution method.

Antibiotic resistance in this example was determined using the broth solution method. This procedure involved preparing two-fold dilutions of antibiotics (e.g., 1, 2, 4, 8, and 16 µg/mL) in a liquid growth medium dispensed in test tubes. The antibiotic-containing tubes were inoculated with a standardized bacterial suspension of about $1-5 \times 10^5$ CFU/mL. Following overnight incubation at 37° C., the tubes were examined for visible bacterial growth as evidenced by turbidity. The lowest concentration of antibiotic that prevented growth represented the minimal inhibitory concentration (MIC).

FIG. 14 shows the antibiotics tested and the results obtained from antibiotic resistance experiment. *A. muciniphila* ST7 appeared to be susceptible to azithromycin, clinadmycin, and tetracycline. *F. prausnitzii* ST38 appeared to be susceptible to amikacin, azithromycin, clinadmycin, tetracycline, and vacomycin. *L. crispatus* ST100 appeared to be susceptible to ampicillin, azithromycin, clinadmycin, tetracycline, and vacomycin.

Example 14

Analysis of Short-Chain Fatty Acid Production in Culture Supernatants of *Akkermansia muciniphila* and *Faecalibacterium prausnitzii* Strains This example shows the analysis of short-chain fatty acid (SCFA) production in brain heart infusion (BHI) culture and chopped meat carbohydrate (CMC) culture supernatants of *Akkermansia muciniphila* (FIG. 15A) and *Faecalibacterium prausnitzii* strains (FIG. 15B-FIG. 15D), respectively.

Quantification of short chain fatty acids in culture media was performed by liquid chromatograph-mass spectrometry (LC-MS/MS). Culture media samples were spiked with stable labelled internal standards followed by protein precipitation with an organic solvent. After centrifugation to pellet protein precipitate, the supernatant was derivatized. The reaction mixture was diluted, and an aliquot was injected onto an LC-MS system comprising an Agilent 1290/AB Sciex QTrap 5500 LC MS/MS system equipped with a C18 reversed phase UHPLC column. The mass spectrometer was operated in negative mode using electrospray ionization (ESI). The peak area of the target analyte ions was measured against the area of the corresponding internal standard ion peaks. Quantitation was performed using a weighted linear least squares regression analysis generated from calibration standards prepared prior to each run. LC-MS/MS raw data were collected and processed using AB SCIEX software Analyst 1.6.2. Data reduction and analysis was performed using Microsoft Excel 2016, and the results of this study are shown in FIG. 15A-FIG. 15C.

Figures 15A, 15B, 15C:
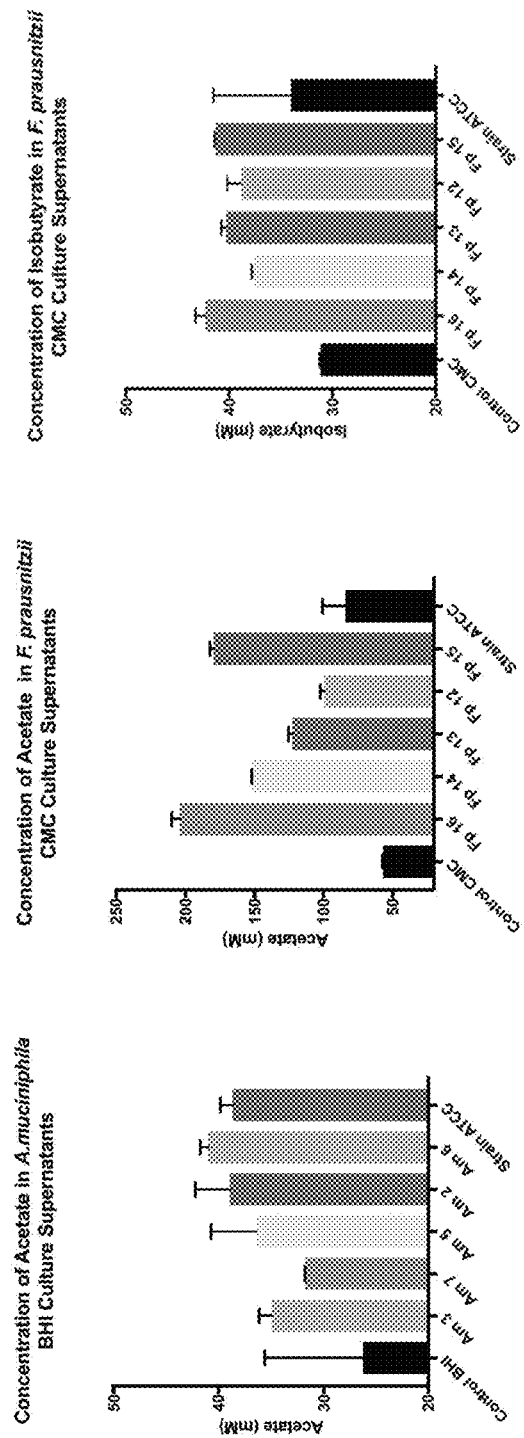
FIG. 15A shows that the *A. muciniphila* strains AM 2, AM 3, AM 5, AM 6, and AM 7 produced comparable amounts of acetate than the ATCC reference strain, with AM 3 and AM 7 on the lower end.
FIG. 15B shows that the *F. prausnitzii* strains FP 12, FP 13, FP 14, FP 15, and FP 16 produced higher amounts of acetate than the ATCC reference strain. Surprisingly, the strains FP 15 and FP 16 produced more than twice the amount of acetate compared to the ATCC reference strain.
FIG. 15C shows that the *F. prausnitzii* strains FP 12, FP 13, FP 14, FP 15, and FP 16 produce significantly higher amounts of isobutyrate compared to the ATCC reference strain or the CMC media control.

FIG. 15A shows that the *A. muciniphila* strains AM 2, AM 3, AM 5, AM 6, and AM 7 produced comparable amounts of acetate than the ATCC reference strain, with AM 3 and AM 7 on the lower end.

FIG. 15B shows that the *F. prausnitzii* strains FP 12, FP 13, FP 14, FP 15, and FP 16 produced higher amounts of acetate than the ATCC reference strain. Surprisingly, the strains FP 15 and FP 16 produced more than twice the amount of acetate compared to the ATCC reference strain.

FIG. 15C shows that the *F. prausnitzii* strains FP 12, FP 13, FP 14, FP 15, and FP 16 produce significantly higher amounts of isobutyrate compared to the ATCC reference strain or the CMC media control.

These findings demonstrate that the *A. muciniphila* and *F. prausnitzii* isolates described herein can be superior at the production of short chain fatty acids such as acetate and isobutyrate compared to conventional strains of these species.

Example 15

Therapeutic Consortia Produce Beneficial Metabolites

This example demonstrates that the therapeutic consortia of the present disclosure produce various metabolites (e.g., fatty acids such as SCFAs, lipids such as phospholipids, etc.) that can have beneficial (e.g., therapeutic and/or preventative) properties.

The supernatant of a cell culture comprising a consortium comprising the strains *A. muciniphila* ST7, *F. prausnitzii* ST38 and *L. crispatus* ST100 is analyzed for metabolites as described above in EXAMPLE 12 and EXAMPLE 14. Analysis of the supernatant shows that the consortium produces significant amounts of fatty acids and lipids (e.g., phospholipids, including phosphatidylcholines and derivatives thereof).

The consortium comprising the strains *A. muciniphila* ST7, *F. prausnitzii* ST38 and *L. crispatus* ST100 is administered to animals suffering from an inflammatory disease induced in a cockroach allergen (CRA) murine model. The mouse model was used as described in EXAMPLE 6. The animals receiving the therapeutic consortium show significantly reduced inflammation compared to control animals. Analysis of inflammatory markers shows a reduction in pro-inflammatory markers (e.g., IL-4, IL-13, $T_H2$ cells, etc.).

Ex vivo analysis of tissue samples (e.g., blood samples) demonstrate a correlation between the production of beneficial metabolites by the therapeutic consortium and the reduction in inflammation. This data demonstrates that a production of specific molecules such as fatty acids, lipids, and/or phospholipids by a therapeutic consortium as described herein can reduce inflammation in a subject.

Example 16

*Akkermansia muciniphila* Produces Beneficial Metabolites

This example demonstrates that *Akkermansia muciniphila* (e.g., the strain *A. muciniphila* ST7) produces various metabolites (e.g., fatty acids such as SCFAs, lipids such as phospholipids, etc.) that can have beneficial (e.g., therapeutic and/or preventative) properties.

The supernatant of a cell culture comprising *Akkermansia muciniphila* is analyzed for metabolites as described above in EXAMPLE 12 and EXAMPLE 14. Analysis of the supernatant shows that *Akkermansia muciniphila* produces significant amounts of fatty acids and lipids. Particularly, the results show that *Akkermansia muciniphila* produces certain phospholipids including phosphatidylcholine and derivatives thereof (e.g., compounds 1-3 shown in FIG. 13).

A pharmaceutical composition comprising a consortium comprising *Akkermansia muciniphila* is administered to animals suffering from an inflammatory disease induced in a cockroach allergen (CRA) murine model. The mouse model was used as described in EXAMPLE 6. The animals receiving the therapeutic consortium show significantly reduced inflammation compared to control animals. Analysis of tissue samples (e.g., blood samples) show a reduction in inflammation can be correlated with the production of phosphatidylcholine and/or phosphatidylcholine derivatives by *Akkermansia muciniphila*. A control cohort that receives a pharmaceutical composition without *Akkermansia muciniphila* shows significantly reduced amount of phosphatidylcholine and/or phosphatidylcholine derivative and higher levels of inflammation.

This data demonstrates that phosphatidylcholine and/or phosphatidylcholine derivative production of *Akkermansia muciniphila* strains can result in a reduction in inflammation, suggesting that specific metabolic activities of microbial consortia can have therapeutic and/or preventative effects in subjects, e.g., to reduce and/or prevent dysbiosis and/or inflammation.

Example 17

Consortia Producing Phosphatidylcholine-like Compounds Protect Against Allergic Airway Inflammation This example demonstrates that therapeutic microbial consortia comprising *Akkermansia muciniphila* (e.g., the strain *A. muciniphila* ST7) produce phosphatidylcholines and derivatives thereof and protect against allergic airway inflammation in a Cockroach allergen (CRA) sensitization model.

Figure 16:
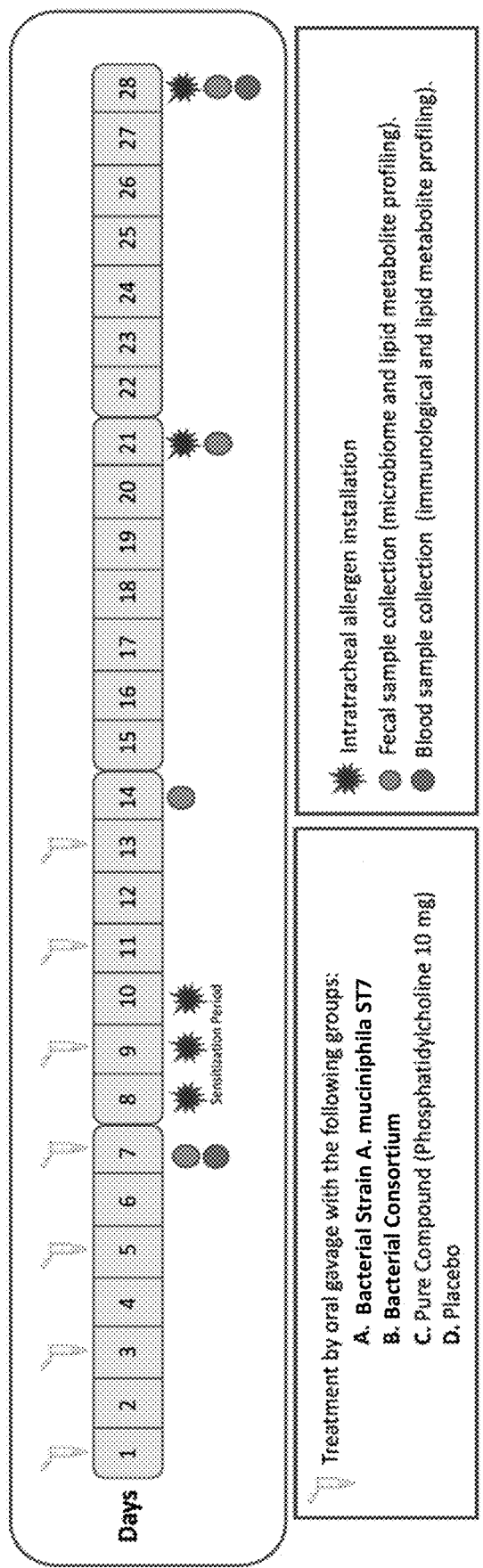
FIG. 16 illustrates an example of a timeline and setup for experimental studies using an allergic airway inflammation mouse model to evaluate the protective effect of phosphatidylcholines or phosphatidylcholine-derived compounds producing intestinal bacterial strains on allergic airway inflammation.

FIG. 16 illustrates an experimental outline that is used to investigate the beneficial, anti-inflammatory properties of the herein described microbial consortia that can produce phosphatidylcholine-like compounds. This 28-day experimental procedure includes 4 cohorts of C57BL/6 mice (7-8 weeks old) that are intratracheally sensitized at days 8, 9, and 10, and subsequently challenged with Cockroach allergen (CRA) at days 21 and 28 of the study. The 4 cohorts (cohorts A-D) are being administered on days 1, 3, 5, 7, 9, 11, and 13 by oral gavage with a suspension comprising either A) the AM-ST7 strain; B) a bacterial consortium comprising AM-ST7, FP-ST38, and LC-ST100, wherein different *Akkermansia muciniphila* (AM) strains can be used, each producing different amounts (e.g., with different rates) of phosphatidylcholine-like compounds (e.g., those depicted in FIG. 13); C) 10 mg of a phosphatidylcholine-derived compounds including [3-[2-aminoethoxy(hydroxy)phosphoryl]oxy-2-hydroxypropyl] tetradecanoate, [3-[2-aminoethoxy(hydroxy)phosphoryl]oxy-2-hydroxypropyl] pentadecanoate, or [3-[2-aminoethoxy(hydroxy)phosphoryl]oxy-2-hydroxypropyl] hexadecanoate, structurally similar derivatives thereof, or those phosphatidylcholine-derived compounds that are shown in FIG. 13; or D) placebo, respectively. Fecal samples for microbiome and lipid metabolite profiling are collected at days 7, 14, 21, and 28. Blood samples for immunological and lipid metabolite profiling are collected at days 7 and 28.

The data demonstrate that mice treated with bacteria capable of producing phosphatidylcholine-like compounds show significantly reduced inflammation. This is found for mice treated with both AM-ST7 and the bacterial consortium comprising AM-ST7 as well as FP-ST38, and LC-ST100. Fecal and blood sample analysis support these data by showing significantly reduced amounts of pro-inflammatory markers and increased amounts of anti-inflammatory compounds. Particularly the amount of produced phosphatidylcholine and/or phosphatidylcholine-like compounds may correlate with a reduction in disease burden.

In sum, this study demonstrates that bacteria producing phosphatidylcholine and/or phosphatidylcholine-like compounds protect against inflammation.

Example 18

Microbial Consortia Producing Phosphatidylcholine-Like Compounds Protect Against Allergic Airway Inflammation This example demonstrates that therapeutic microbial consortia of the present disclosure can alter the metabolism of certain compounds in a subject, resulting in increased therapeutic function of these consortia.

A pharmaceutical composition comprising a consortium comprising an *Akkermansia* sp. *Faecalibacterium* sp., and/or *Lactobacillus* sp. is administered to animals suffering from an inflammatory disease induced in a cockroach allergen (CRA) murine model. The mouse model was used as described in EXAMPLE 6.

The animals receiving the therapeutic consortium show significantly reduced inflammation compared to control animals. Analysis of tissue samples (e.g., blood samples) indicate that animals treated with the therapeutic consortium comprise higher amounts of anti-inflammatory compounds and metabolites such as alpha-linolenic acid, and reduced amounts of pro-inflammatory compounds and metabolites such as arachidonic acid as a metabolite of alpha-linolenic acid.

This data indicates that, in addition to the production of anti-inflammatory compounds, the therapeutic microbial consortia of the present disclosure can also alter the metabolism of certain compounds in a subject, in a way that reduces the ratio of anti-inflammatory compounds or metabolites to pro-inflammatory compounds or metabolites in a subject, resulting in the treatment and/or prevention of a disease or condition in a subject.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein may be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. A pharmaceutical composition, wherein the pharmaceutical composition comprises at least one of *Coprococcus comes* DSM 33176, *Bacteroides faecis* DSM 33177, *Bacteroides thetaiotaomicron* DSM 33178, *Bifidobacterium Longum* DSM 33179, *Blautia producta* DSM 33180, *Faecalibacterium prausnitzii* DSM 33185, *Faecalibacterium prausnitzii* DSM 33186, *Lactobacillus crispatus* DSM 33187, *Dorea longicatena* DSM 33188, *Faecalibacterium prausnitzii* DSM 33190, *Faecalibacterium prausnitzii* DSM 33191, or *Akkermansia muciniphila* DSM 33213, wherein the pharmaceutical composition is formulated as an oral dosage form, and wherein the pharmaceutical composition comprises at least about $10^2$ cfu per strain.

2. The pharmaceutical composition of claim 1, wherein the pharmaceutical composition comprises the *Akkermansia muciniphila* DSM 33213.

3. The pharmaceutical composition of claim 1, wherein the pharmaceutical composition comprises at least one of the *Faecalibacterium prausnitzii* DSM 33185, the *Faecalibacterium prausnitzii* DSM 33186, the *Faecalibacterium prausnitzii* DSM 33190, or the *Faecalibacterium prausnitzii* DSM 33191.

4. The pharmaceutical composition of claim 1, wherein the pharmaceutical composition comprises the *Faecalibacterium prausnitzii* DSM 33185.

5. The pharmaceutical composition of claim 1, wherein the pharmaceutical composition comprises the *Lactobacillus crispatus* DSM 33187.

6. The pharmaceutical composition of claim 1, wherein the pharmaceutical composition comprises at least one of the

*Akkermansia muciniphila* DSM 33213, the *Faecalibacterium prausnitzii* DSM 33185, or the *Lactobacillus crispatus* DSM 33187.

7. The pharmaceutical composition of claim 1, wherein the pharmaceutical composition further comprises a pharmaceutically acceptable excipient.

8. The pharmaceutical composition of claim 7, wherein the pharmaceutically acceptable excipient is configured to consume oxygen.

9. The pharmaceutical composition of claim 1, wherein the pharmaceutical composition is formulated in the form of a drop, a liquid, a frozen liquid, a suspension, an emulsion, or a powder.

10. The pharmaceutical composition of claim 1, wherein the pharmaceutical composition comprises at least about $10^5$ to about $10^8$ cfu per strain.

11. A pharmaceutical composition, wherein the pharmaceutical composition comprises at least two of the *Coprococcus comes* DSM 33176, the *Bacteroides faecis* DSM 33177, the *Bacteroides thetaiotaomicron* DSM 33178, the *Bifidobacterium Longum* DSM 33179, the *Blautia producta* DSM 33180, the *Faecalibacterium prausnitzii* DSM 33185, the *Faecalibacterium prausnitzii* DSM 33186, the *Lactobacillus crispatus* DSM 33187, the *Dorea longicatena* DSM 33188, the *Faecalibacterium prausnitzii* DSM 33190, the *Faecalibacterium prausnitzii* DSM 33191, or the *Akkermansia muciniphila* DSM 33213.

12. The pharmaceutical composition of claim 11, wherein the pharmaceutical composition comprises the *Akkermansia muciniphila* DSM 33213.

13. The pharmaceutical composition of claim 11, wherein the pharmaceutical composition comprises at least one of the *Faecalibacterium prausnitzii* DSM 33185, the *Faecalibacterium prausnitzii* DSM 33186, the *Faecalibacterium prausnitzii* DSM 33190, or the *Faecalibacterium prausnitzii* DSM 33191.

14. The pharmaceutical composition of claim 11, wherein the pharmaceutical composition comprises the *Faecalibacterium prausnitzii* DSM 33185.

15. The pharmaceutical composition of claim 11, wherein the pharmaceutical composition comprises the *Lactobacillus crispatus* DSM 33187.

16. The pharmaceutical composition of claim 11, wherein the pharmaceutical composition comprises at least one of the *Akkermansia muciniphila* DSM 33213, the *Faecalibacterium prausnitzii* DSM 33185, or the *Lactobacillus crispatus* DSM 33187.

17. The pharmaceutical composition of claim 11, wherein the pharmaceutical composition comprises at least two of the *Akkermansia muciniphila* DSM 33213, the *Faecalibacterium prausnitzii* DSM 33185, or the *Lactobacillus crispatus* DSM 33187.

18. The pharmaceutical composition of claim 11, wherein the pharmaceutical composition comprises the *Akkermansia muciniphila* DSM 33213, the *Faecalibacterium prausnitzii* DSM 33185, and the *Lactobacillus crispatus* DSM 33187.

19. The pharmaceutical composition of claim 11, wherein the pharmaceutical composition further comprises a pharmaceutically acceptable excipient.

20. The pharmaceutical composition of claim 19, wherein the pharmaceutically acceptable excipient is configured to consume oxygen.

21. The pharmaceutical composition of claim 11, wherein the pharmaceutical composition is formulated in the form of a drop, a liquid, a frozen liquid, a suspension, an emulsion, or a powder.

22. The pharmaceutical composition of claim 11, wherein the pharmaceutical composition is formulated as an oral dosage form.

23. The pharmaceutical composition of claim 11, wherein the pharmaceutical composition comprises at least about $10^2$ to about $10^{12}$ cfu per strain.

24. The pharmaceutical composition of claim 23, wherein the pharmaceutical composition comprises at least about $10^5$ to about $10^8$ cfu per strain.

25. A method of treating inflammation or an inflammatory disease in a subject in need thereof, comprising administering to the subject an effective amount of a pharmaceutical composition of claim 1.

26. A method of treating inflammation or an inflammatory disease in a subject in need thereof, comprising administering to the subject an effective amount of a pharmaceutical composition of claim 11.

* * * * *

UNITED STATES PATENT AND TRADEMARK OFFICE
CERTIFICATE OF CORRECTION

PATENT NO. : 11,369,644 B2
APPLICATION NO. : 17/067354
DATED : June 28, 2022
INVENTOR(S) : Nikole Kimes et al.

It is certified that error appears in the above-identified patent and that said Letters Patent is hereby corrected as shown below:

In the Claims

In Claim 11, please make the following change:
Replace "at least two of the *Coprococcus comes* DSM 33176, the *Bacteroides faecis* DSM 33177, the *Bacteroides thetaiotaomicron* DSM 33178, the *Bifidobacterium Longum* DSM 33179, the *Blautia producta* DSM 33180, the *Faecalibacterium prausnitzii* DSM 33185, the *Faecalibacterium prausnitzii* DSM 33186, the *Lactobacillus crispatus* DSM 33187, the *Dorea longicatena* DSM 33188, the *Faecalibacterium prausnitzii* DSM 33190, the *Faecalibacterium prausnitzii* DSM 33191, or the *Akkermansia muciniphila* DSM 33213." with --at least two of *Coprococcus comes* DSM 33176, *Bacteroides faecis* DSM 33177, *Bacteroides thetaiotaomicron* DSM 33178, *Bifidobacterium Longum* DSM 33179, *Blautia producta* DSM 33180, *Faecalibacterium prausnitzii* DSM 33185, *Faecalibacterium prausnitzii* DSM 33186, *Lactobacillus crispatus* DSM 33187, *Dorea longicatena* DSM 33188, *Faecalibacterium prausnitzii* DSM 33190, *Faecalibacterium prausnitzii* DSM 33191, or *Akkermansia muciniphila* DSM 33213.--

Signed and Sealed this
Sixth Day of June, 2023

Katherine Kelly Vidal
*Director of the United States Patent and Trademark Office*